United States Patent [19]

Brockway et al.

[11] Patent Number: 4,562,841
[45] Date of Patent: Jan. 7, 1986

[54] PROGRAMMABLE MULTI-MODE CARDIAC PACEMAKER

[75] Inventors: Brian P. Brockway, Minneapolis; Robert D. Dreher, Roseville; Daniel E. Huntwork, White Bear Lake; Brock S. Lindstedt; Douglas C. Morrison, both of St. Paul; Perry A. Mills, Roseville, all of Minn.

[73] Assignee: Cardiac Pacemakers, Inc., St. Paul, Minn.

[21] Appl. No.: 405,711

[22] Filed: Aug. 5, 1982

[51] Int. Cl.⁴ ............................................. A61N 1/36
[52] U.S. Cl. ............................................. 128/419 PG
[58] Field of Search ................... 128/419 PG, 419 PT

[56] References Cited

U.S. PATENT DOCUMENTS

| | | | |
|---|---|---|---|
| 3,662,759 | 5/1972 | Dabolt | 128/419 PG |
| 3,693,626 | 9/1972 | Cole | 128/419 PG |
| 3,718,909 | 2/1973 | Greatbatch | 128/419 PT |
| 4,052,991 | 10/1977 | Zacouto | 128/419 PG |
| 4,290,429 | 9/1981 | Blaser | 128/419 PT |
| 4,305,397 | 12/1981 | Weisbrod et al. | 128/419 PT |

FOREIGN PATENT DOCUMENTS 2026870  2/1980  United Kingdom .......... 128/419 PG

*Primary Examiner*—William E. Kamm
*Attorney, Agent, or Firm*—Orrin M. Haugen; Thomas J. Nikolai; Douglas L. Tschida

[57] ABSTRACT

A programmable cardiac pacemaker that is selectively programmable via a radio frequency communications link into one of a plurality of a single and dual chamber pacing modes. Depending upon the mode selected, an associated plurality of pacing parameters may be programmed, each within a predetermined range of possible magnitudes.

The pacemaker includes a rate smoothing function for preventing the rate interval from changing by more than a predetermined percentage on a cycle-to-cycle basis; and a graceful degradation function for causing the ventricular pacing rate to decay when the atrial rate exceeds a programmed upper rate limit for a predetermined length of time. A graceful degration onset time and rate of decay are also programmable. Additionally, the pacemaker contains a set of pre-programmed alternative pacing parameters for at least one mode and which can be independently reverted to.

The pacemaker control circuitry is organized about a central bus into an I/O controller and a pacing controller. Pacing control is continuous and its I/O communications operate on a prioritized basis. I/O control permits the programming of any register and the interrogation of a variety of analog parameters associated therewith.

27 Claims, 72 Drawing Figures

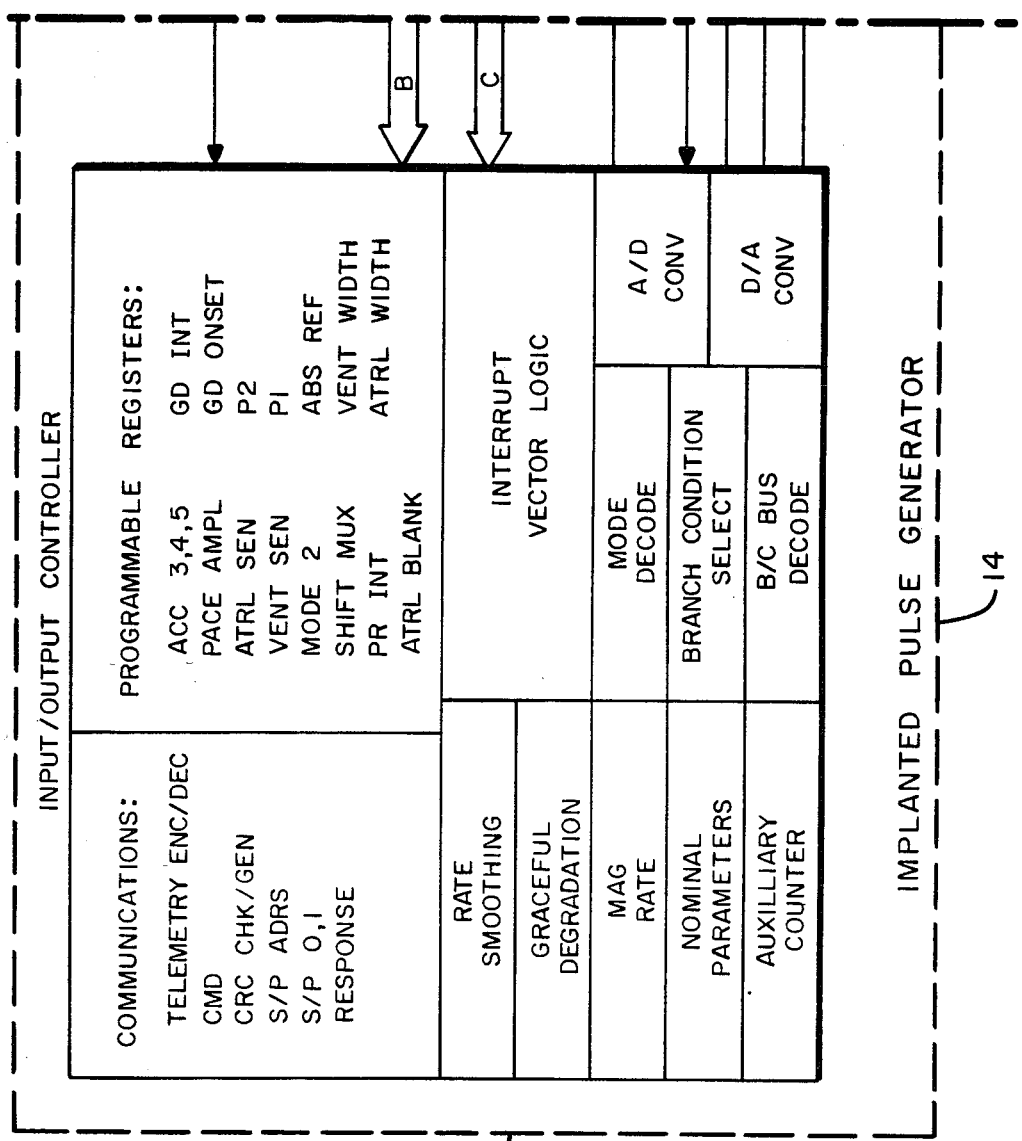
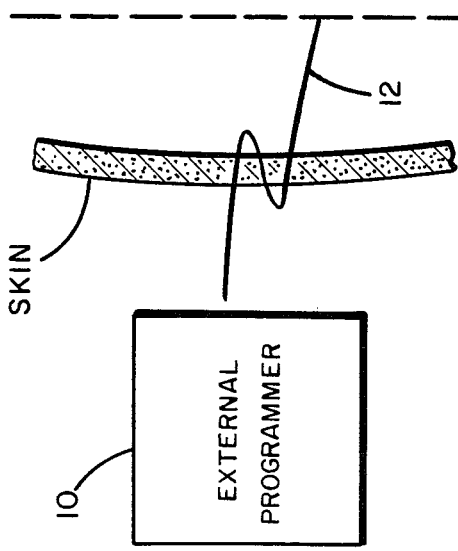
Fig. 1a
Fig. 1b
Fig. 1

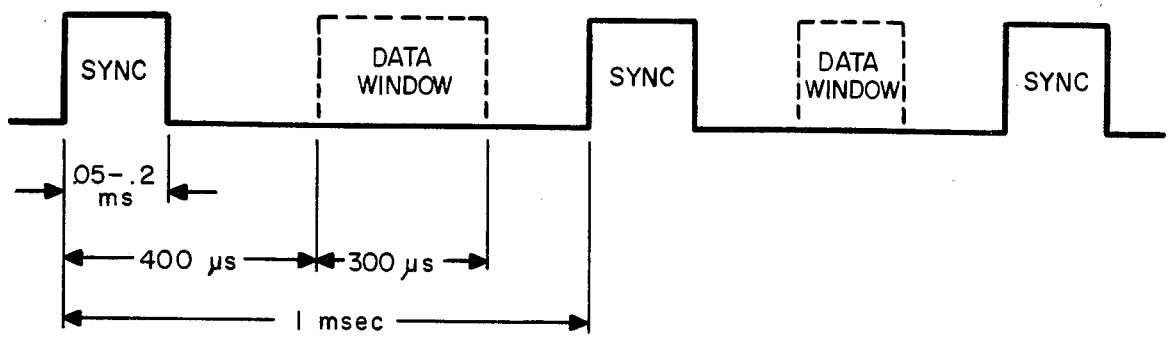
Fig. 2
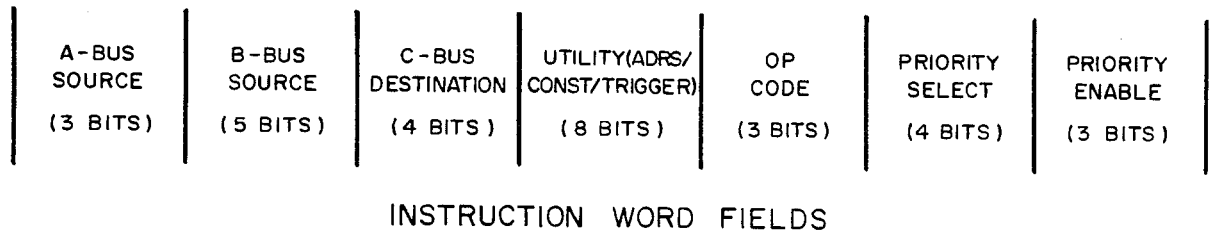
INSTRUCTION WORD FIELDS
Fig. 9
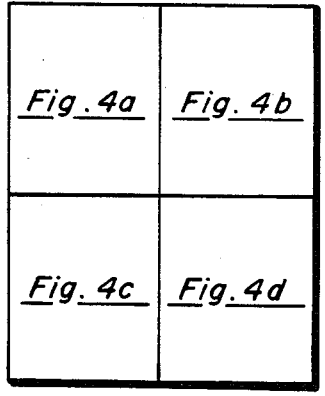
Fig. 4
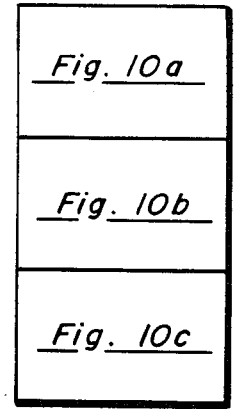
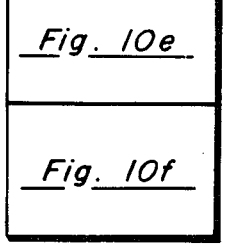
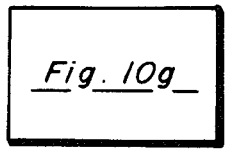
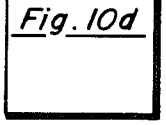
Fig. 10

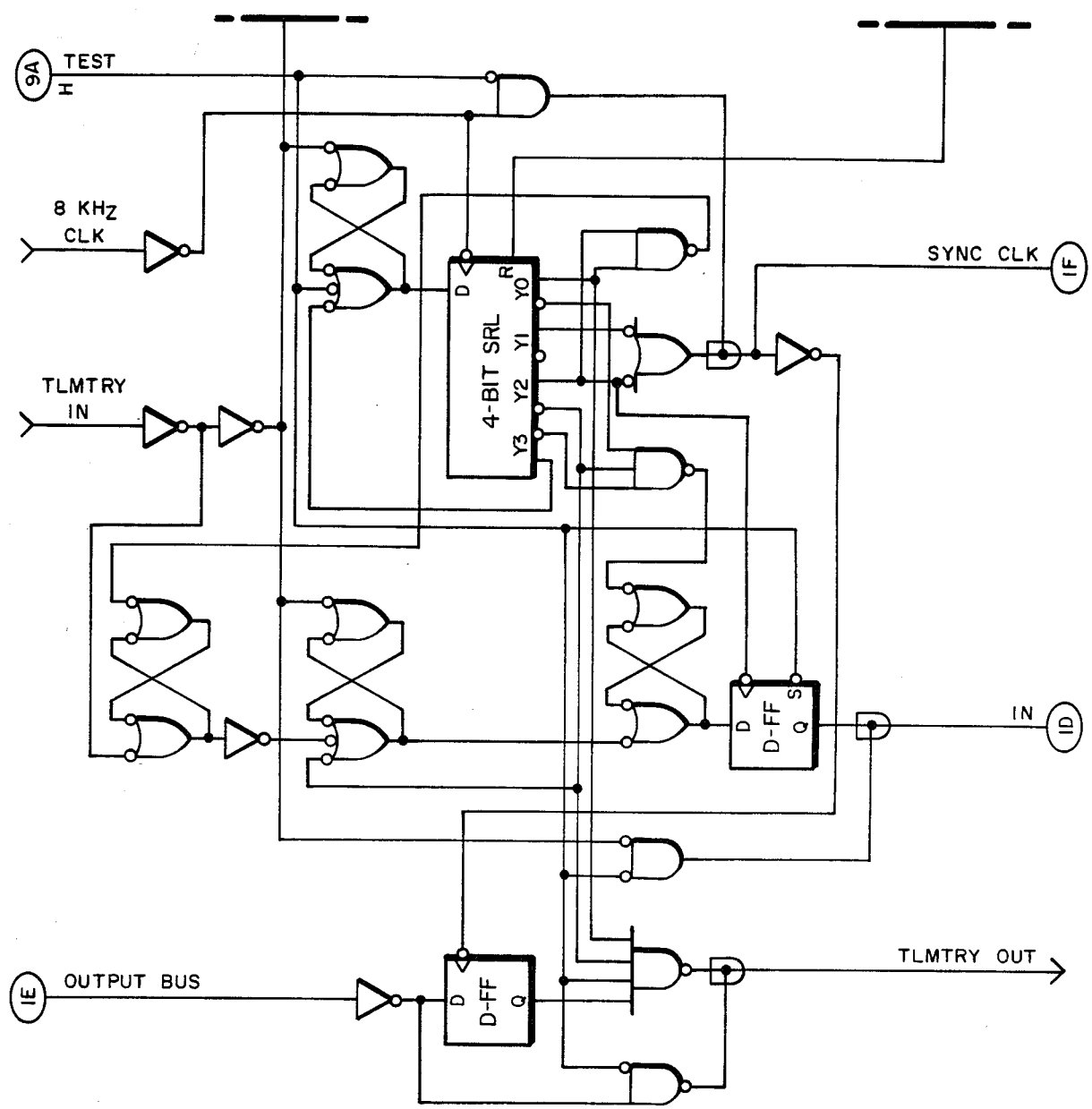

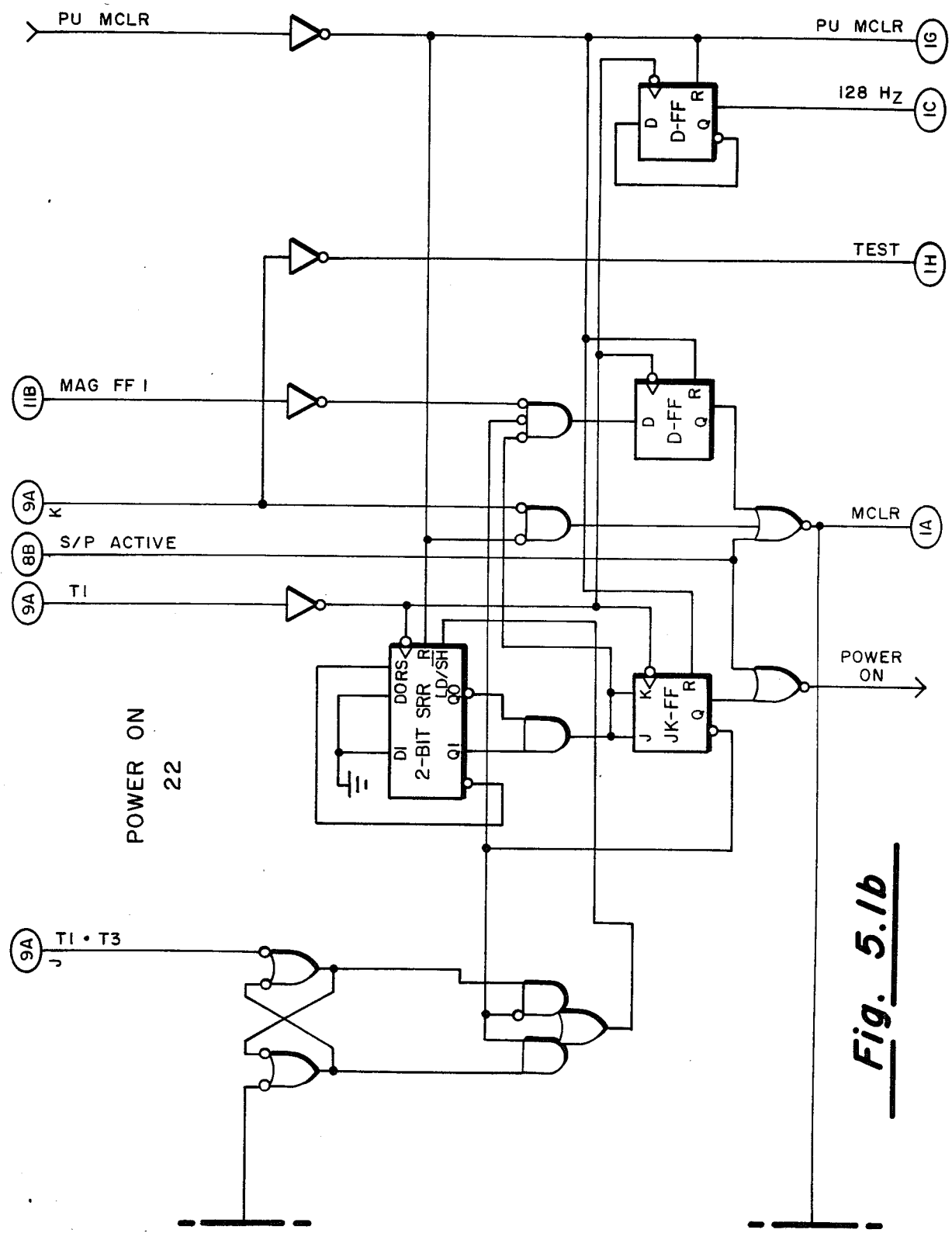
Fig. 5.1b

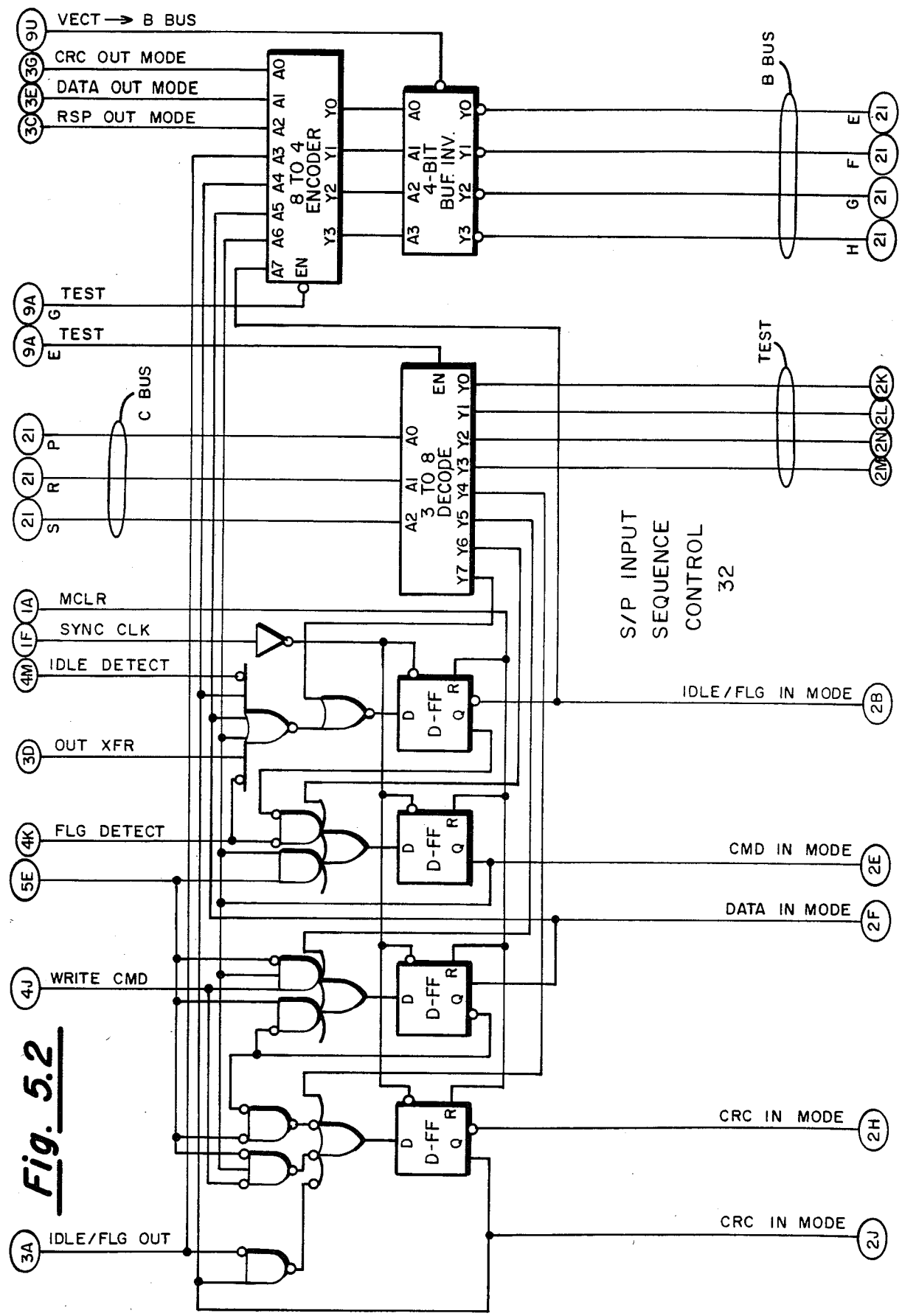
Fig. 5.2

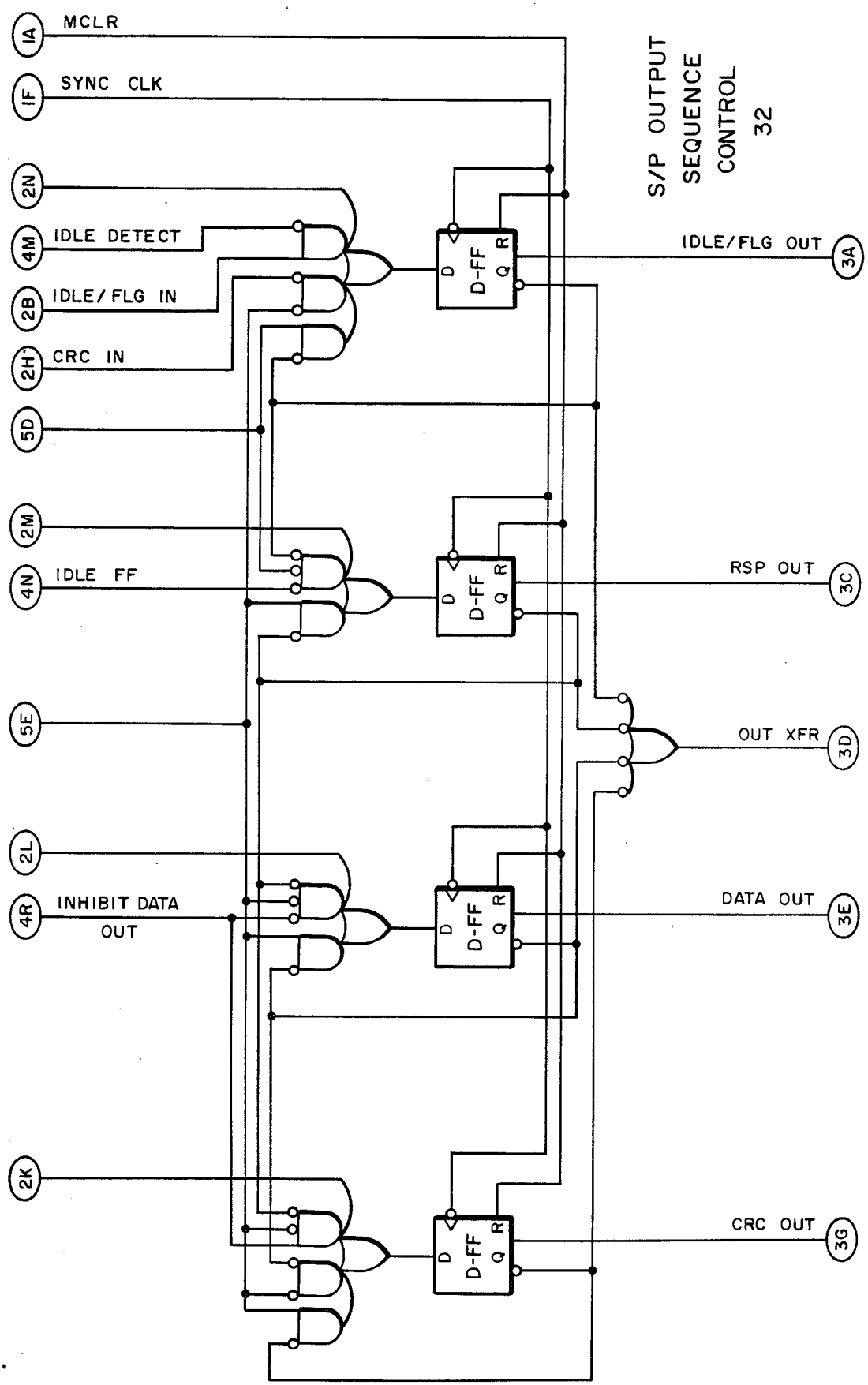
Fig. 5.3

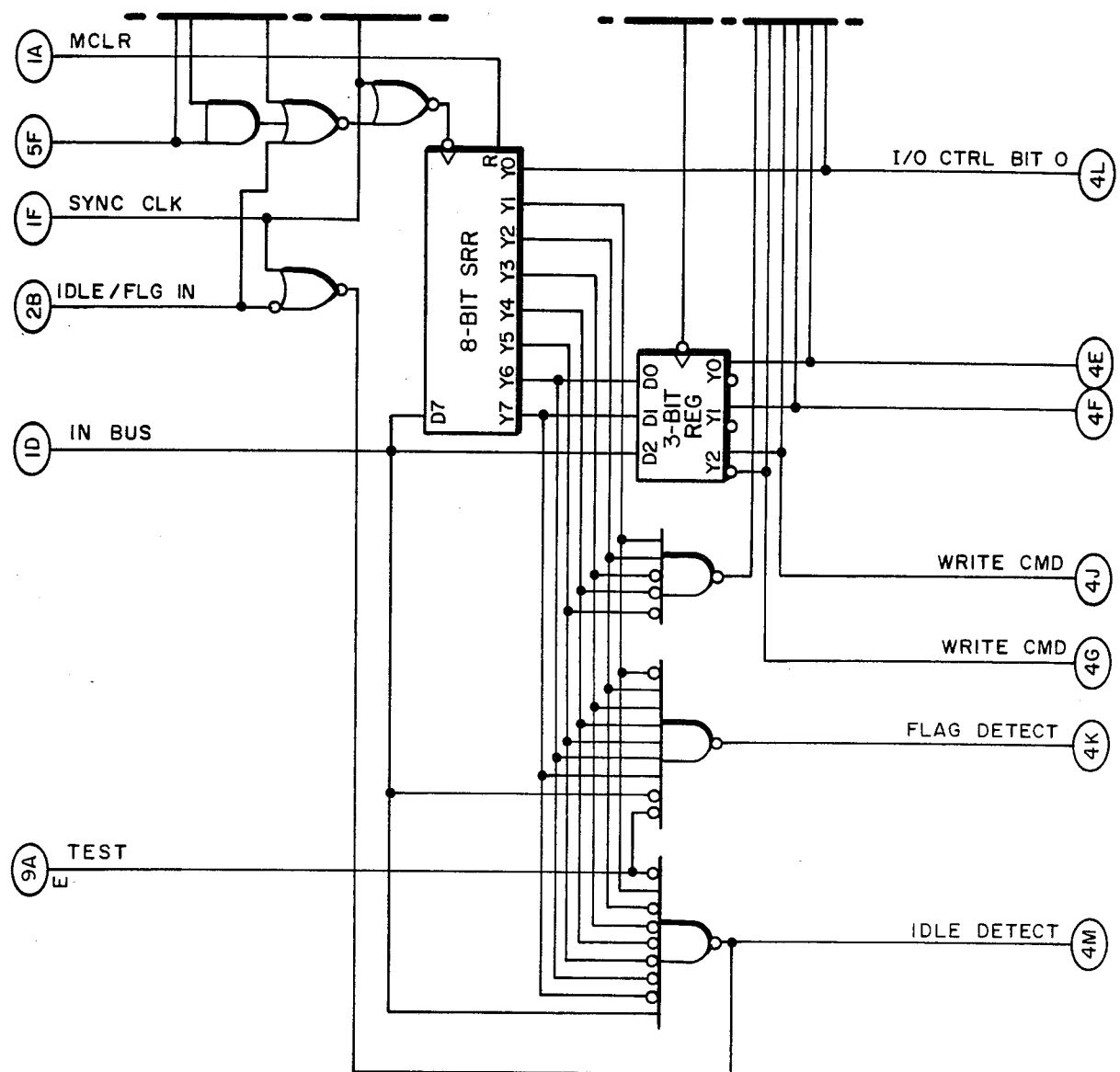
Fig. 5.4
Fig. 5.4a
Fig. 5.4b
COMMAND DECODE 30

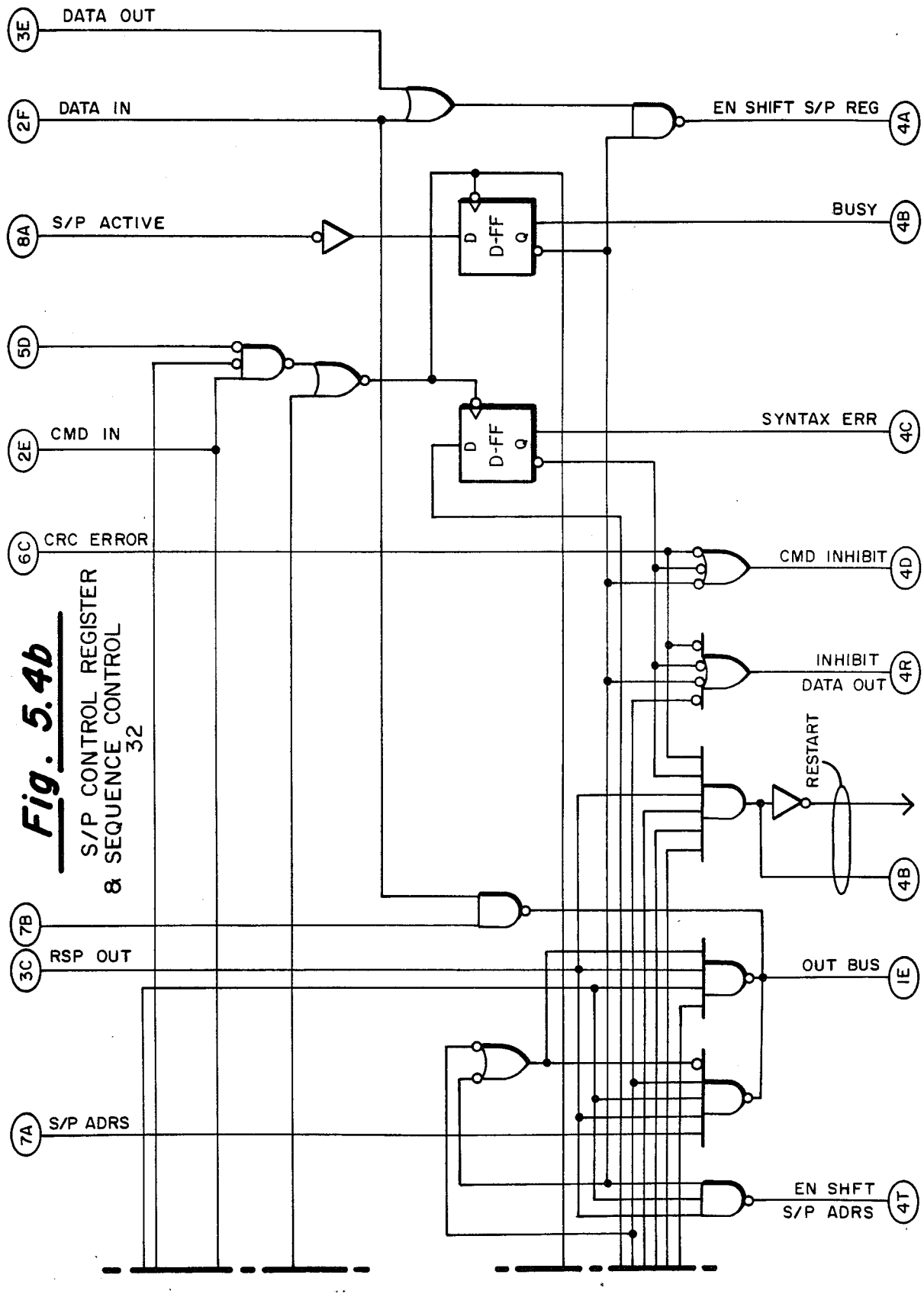

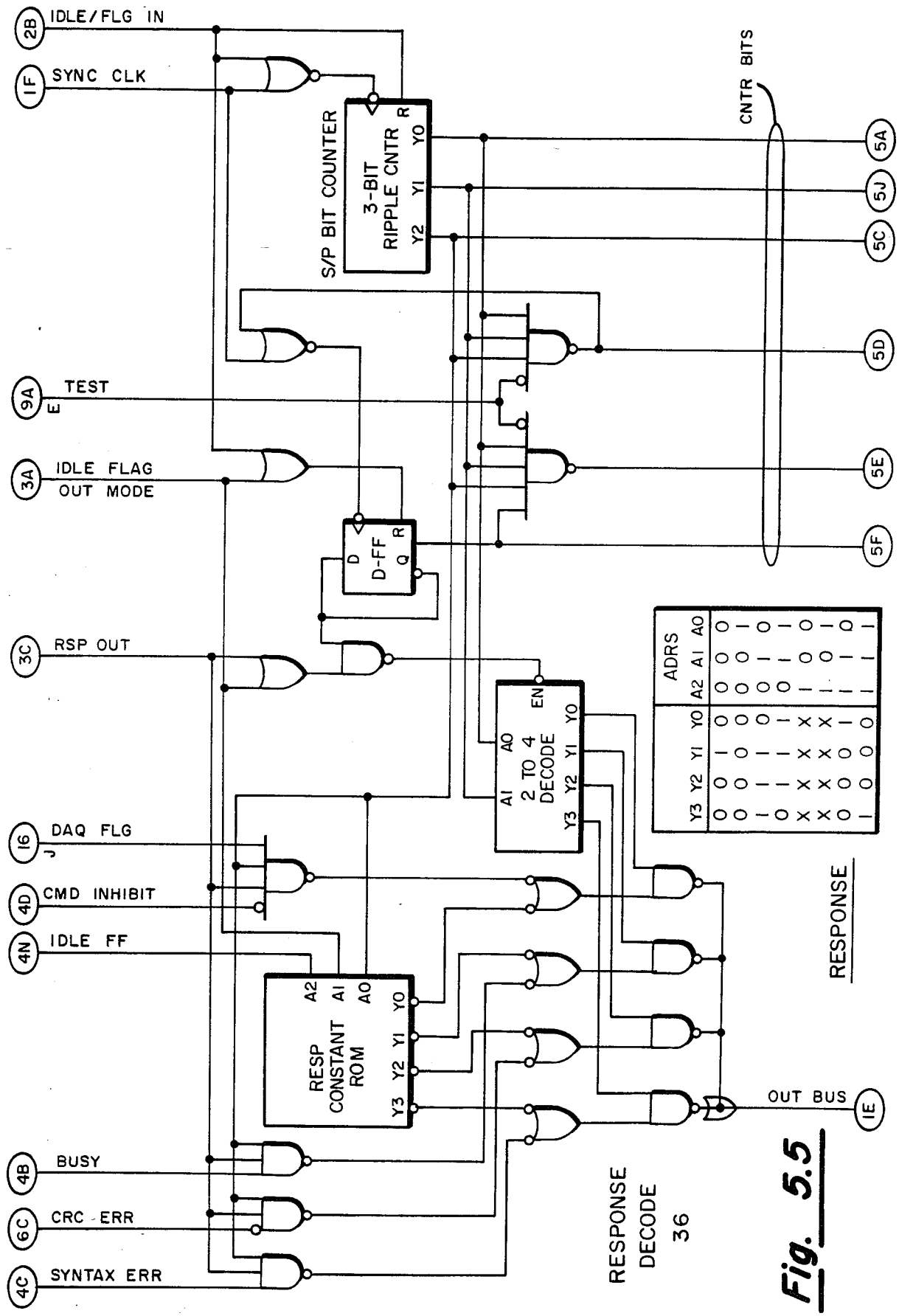
Fig. 5.5

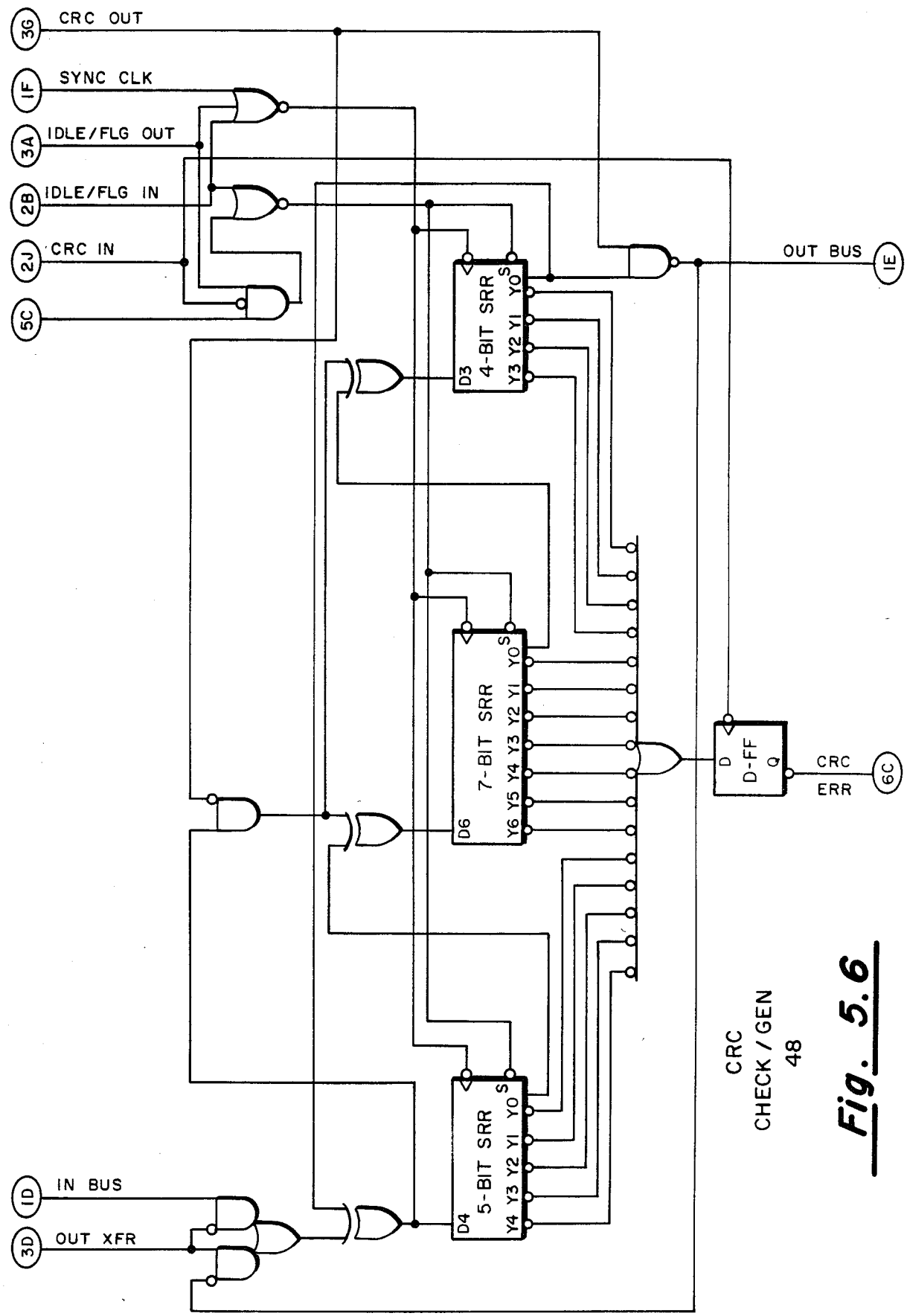
Fig. 5.6

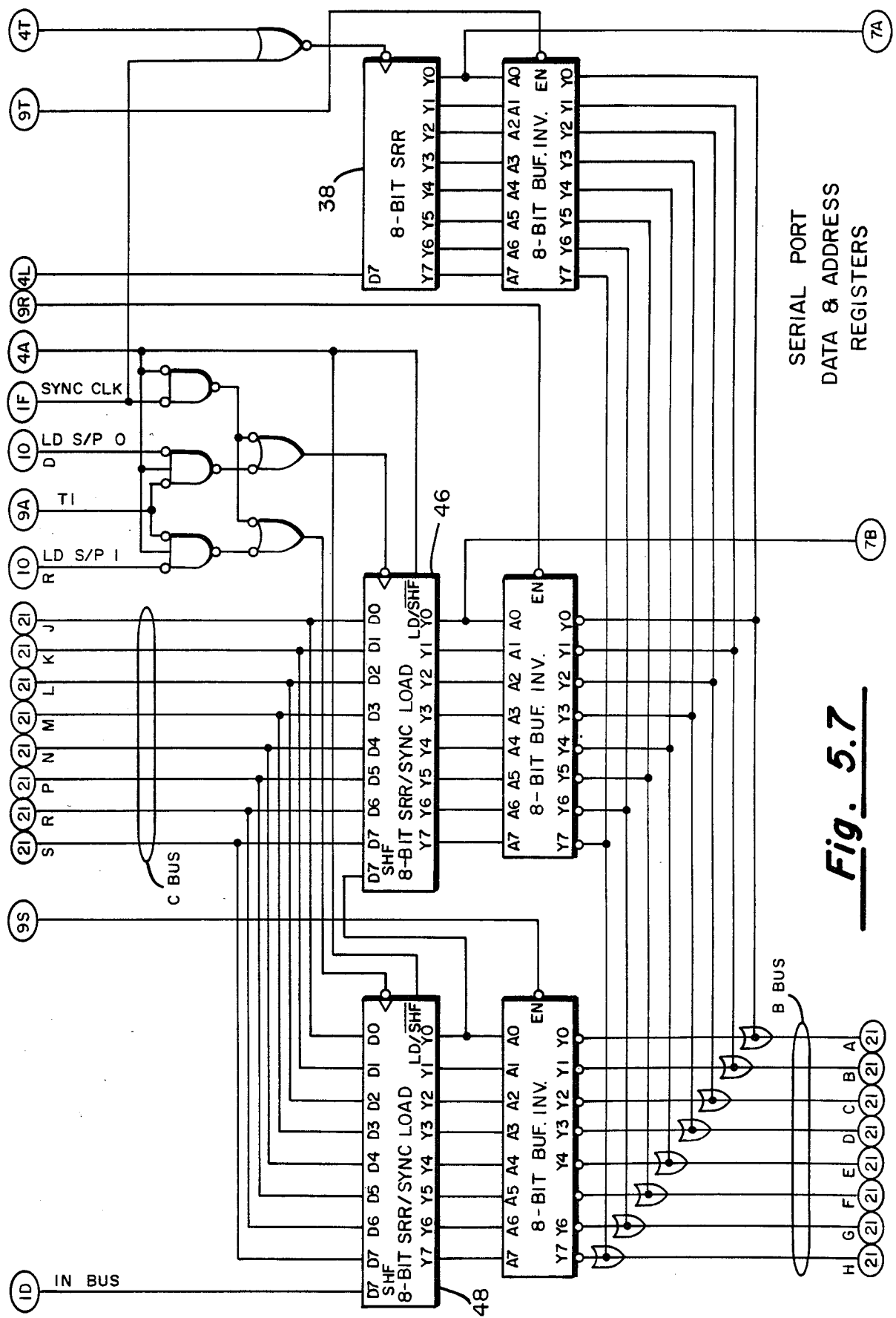
Fig. 5.7

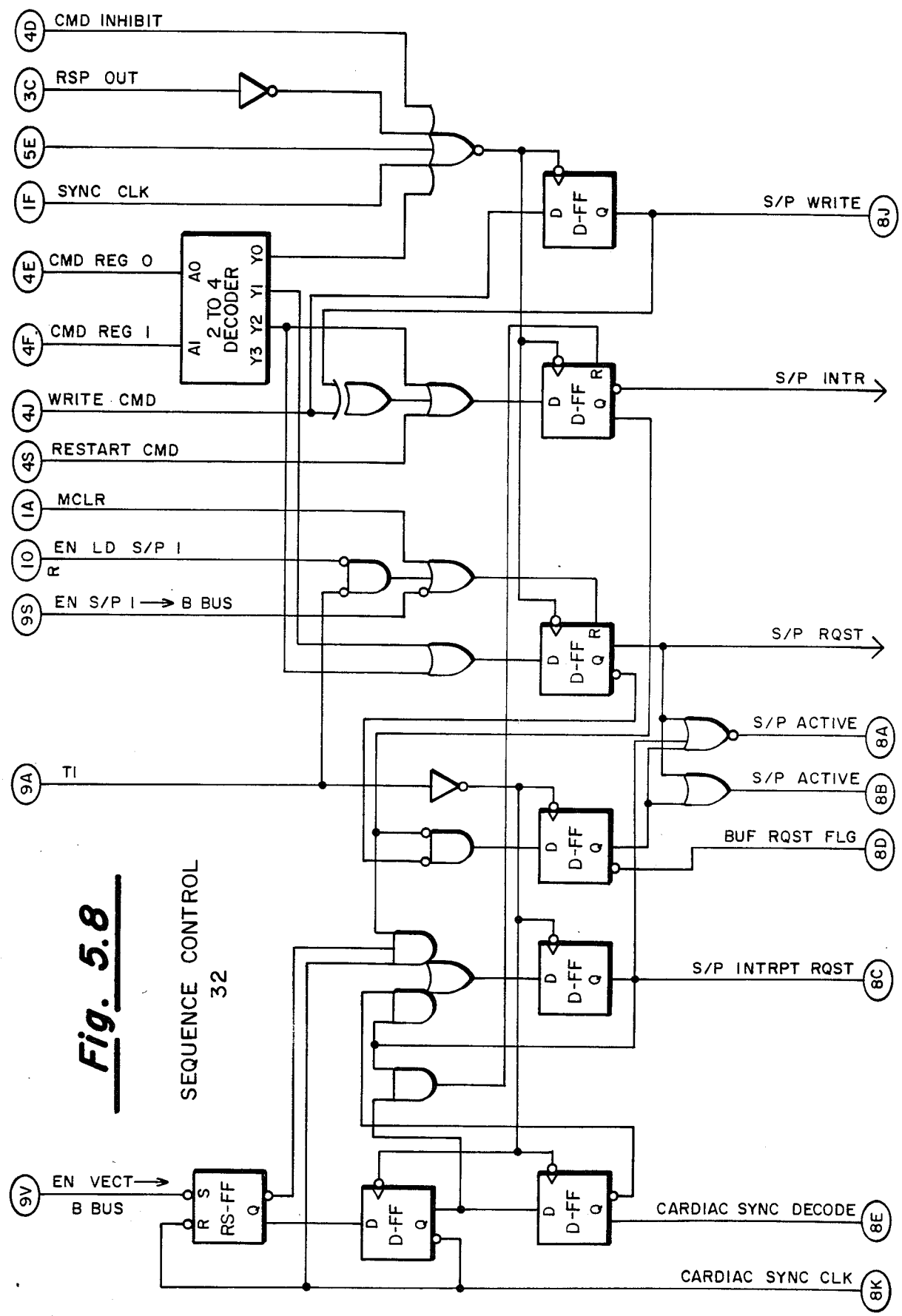
Fig. 5.8 SEQUENCE CONTROL 32

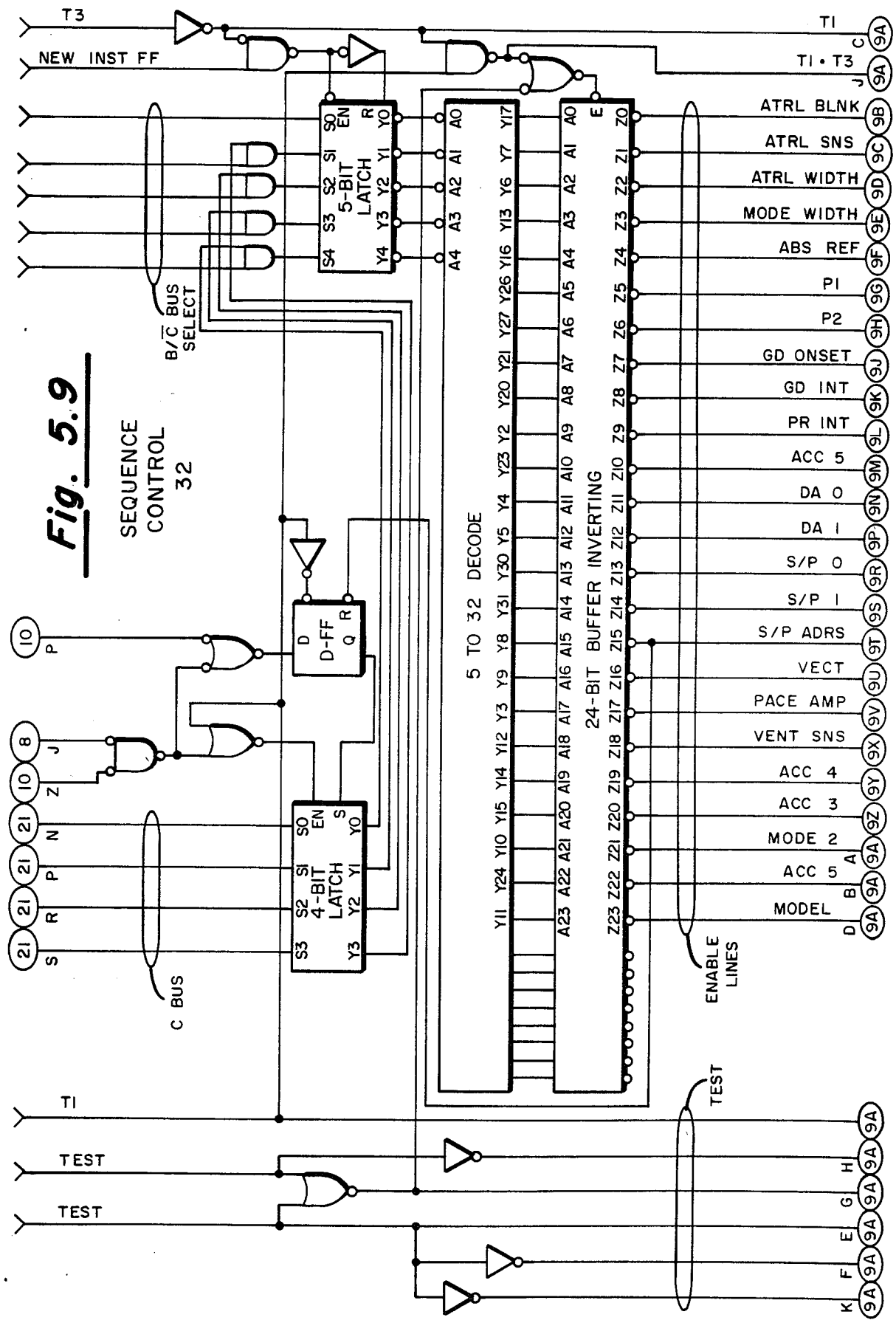
Fig. 5.9 SEQUENCE CONTROL 32

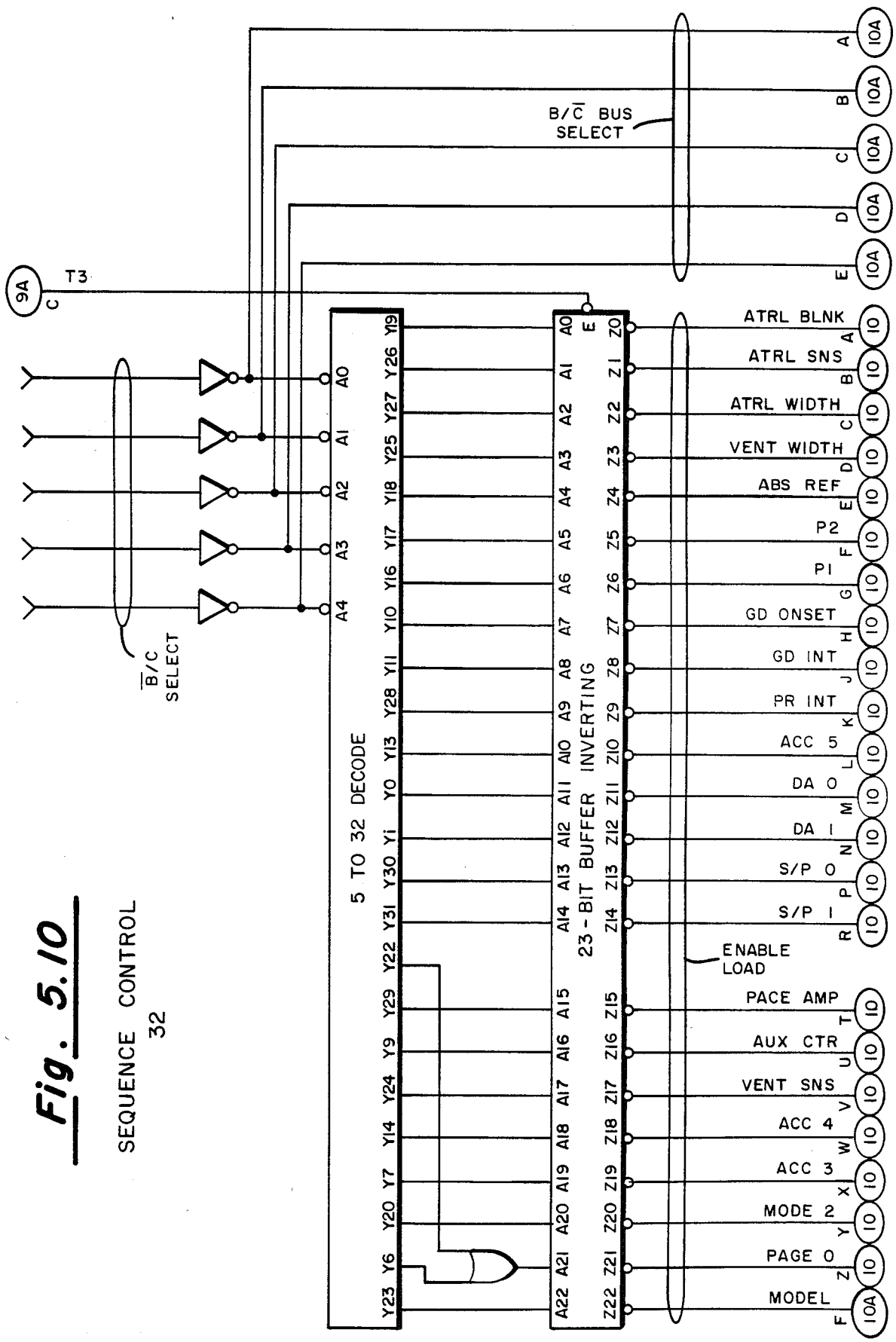
Fig. 5.10 SEQUENCE CONTROL 32

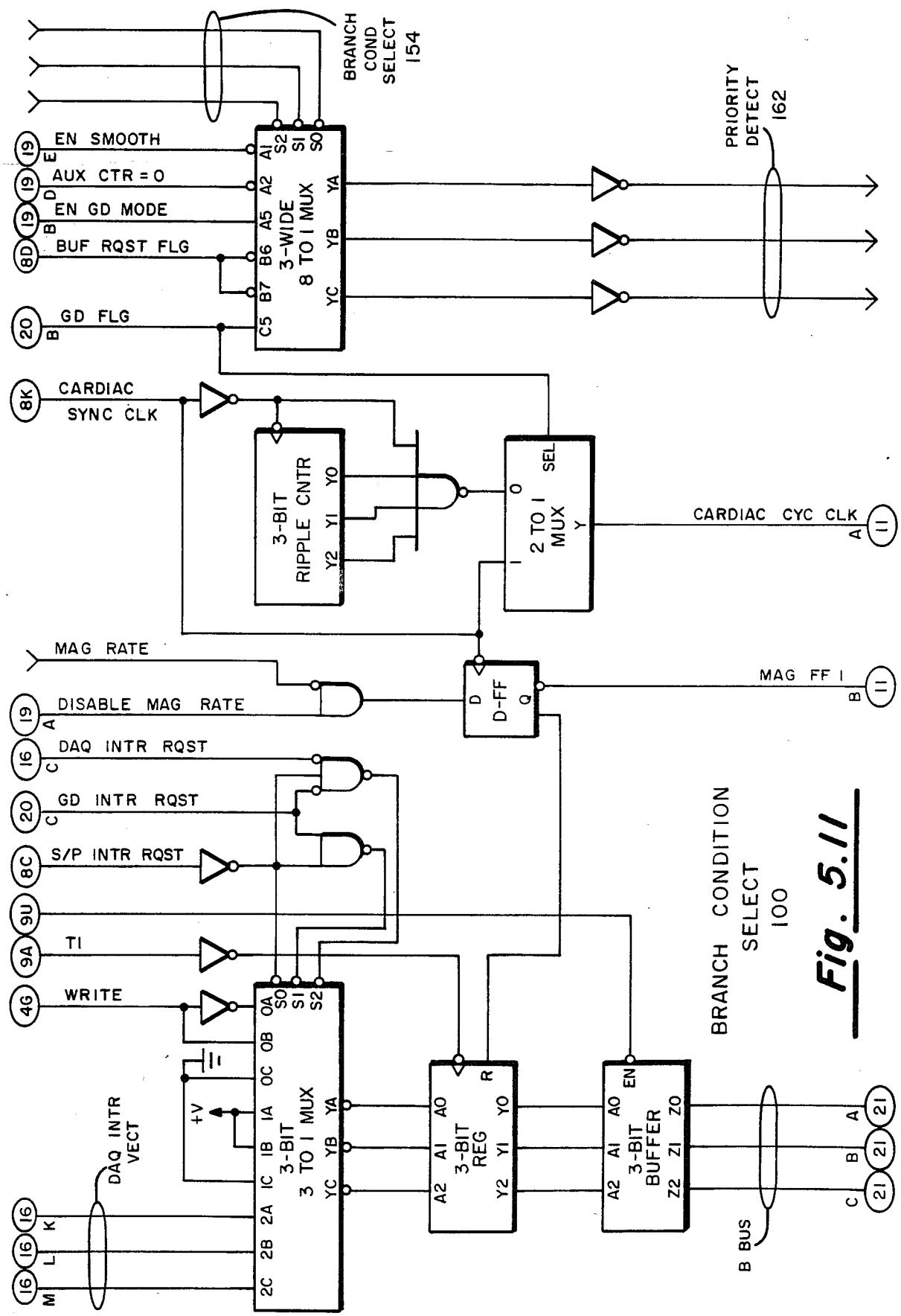
Fig. 5.11

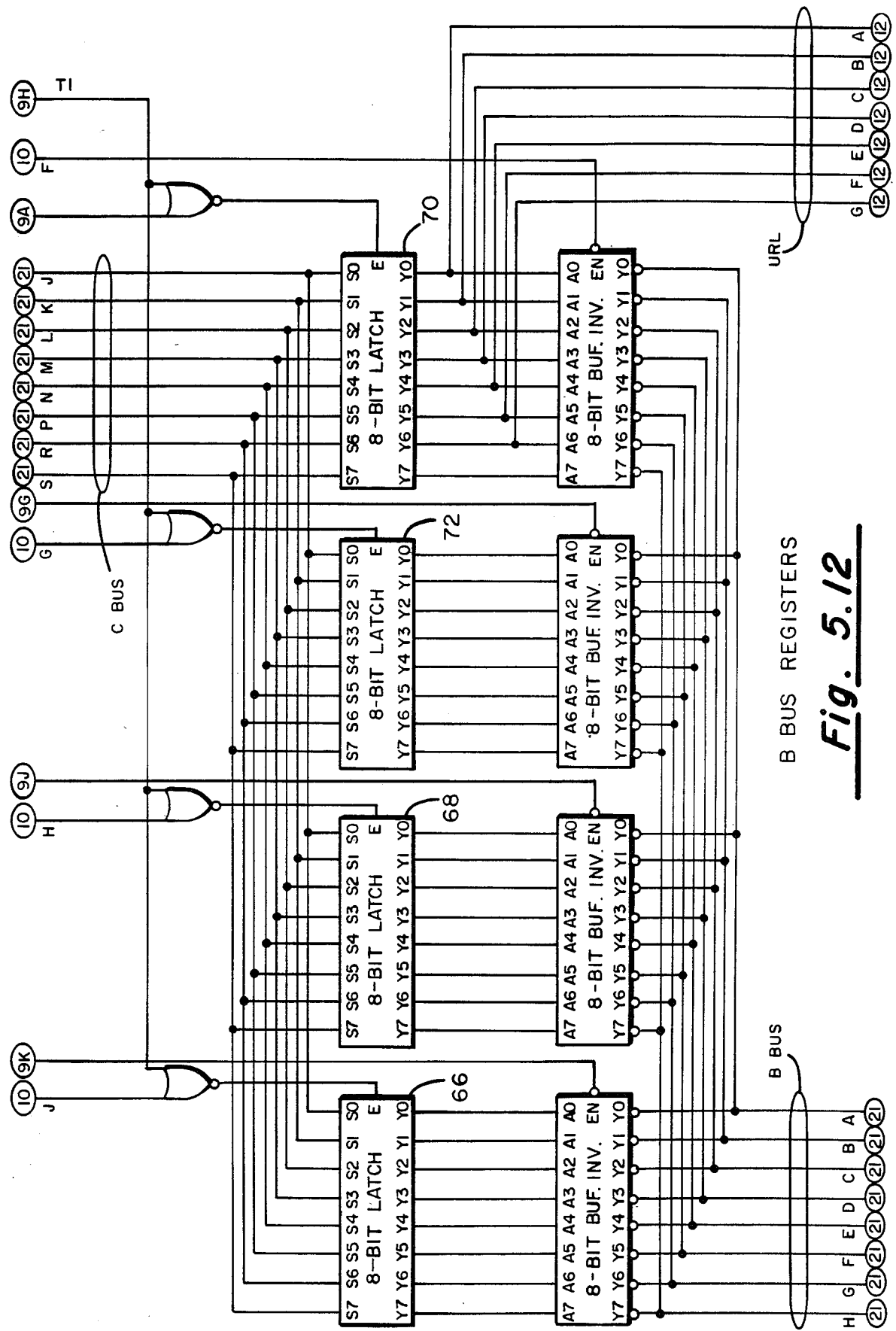
Fig. 5.12  B BUS REGISTERS

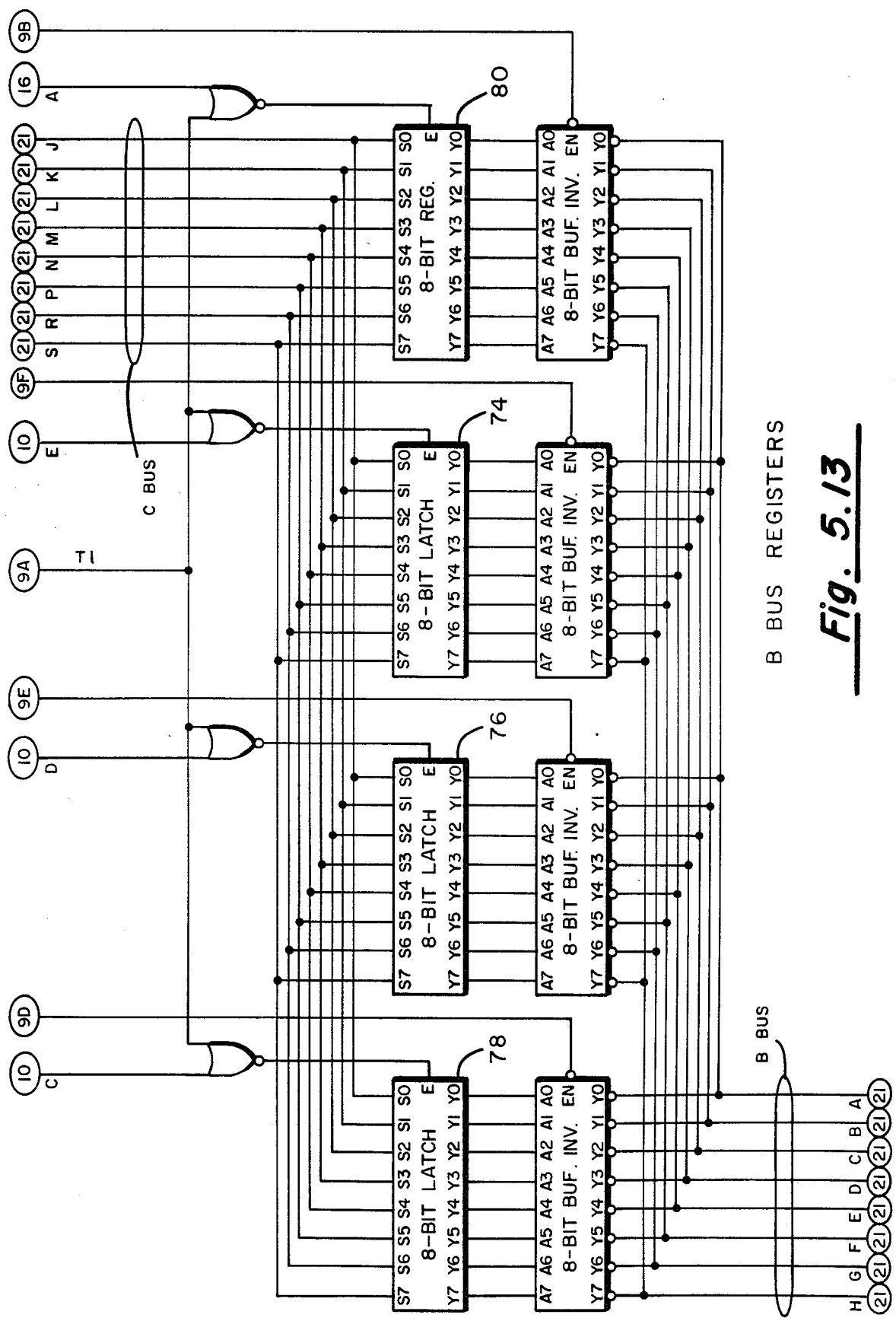

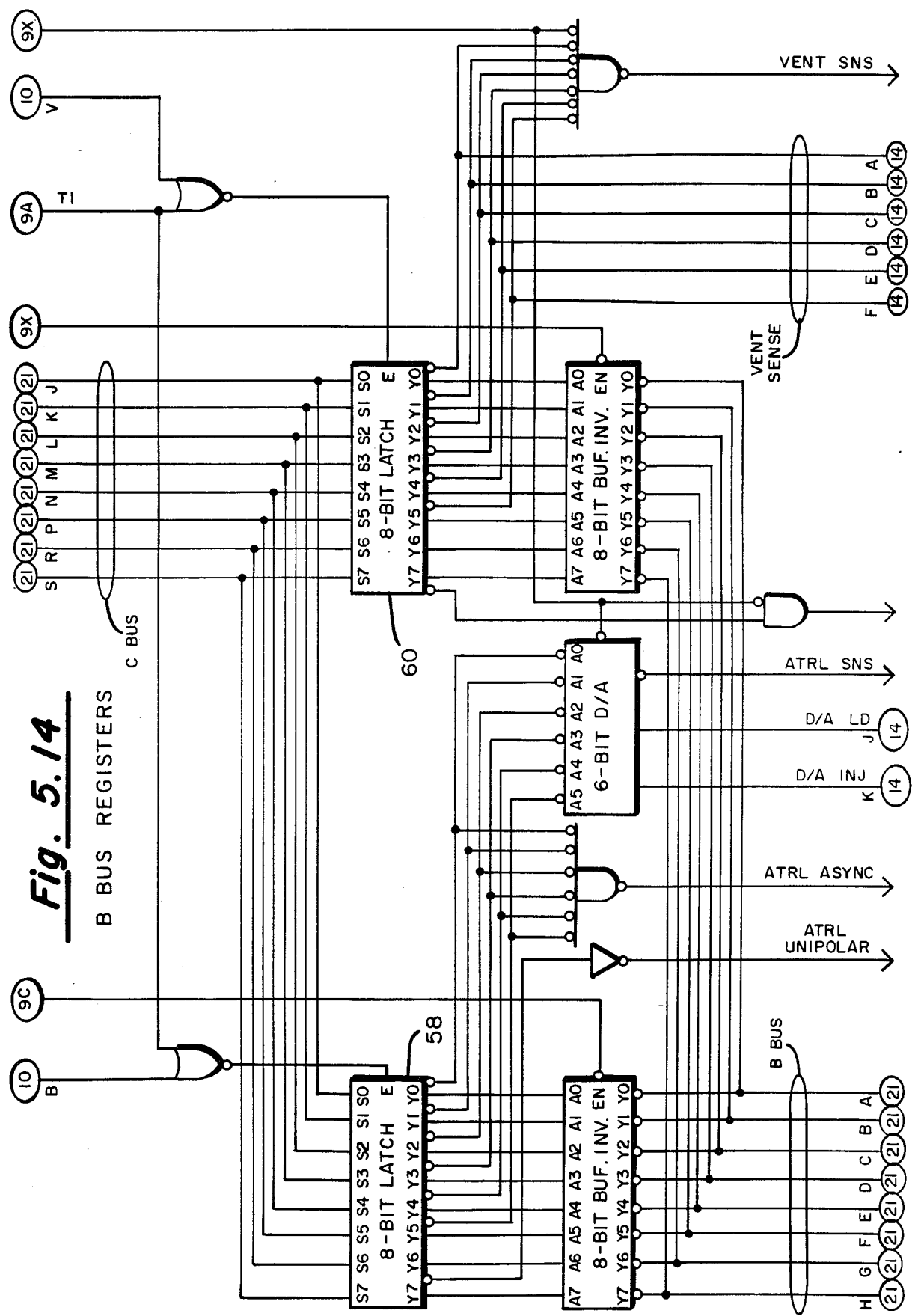
Fig. 5.14 B BUS REGISTERS

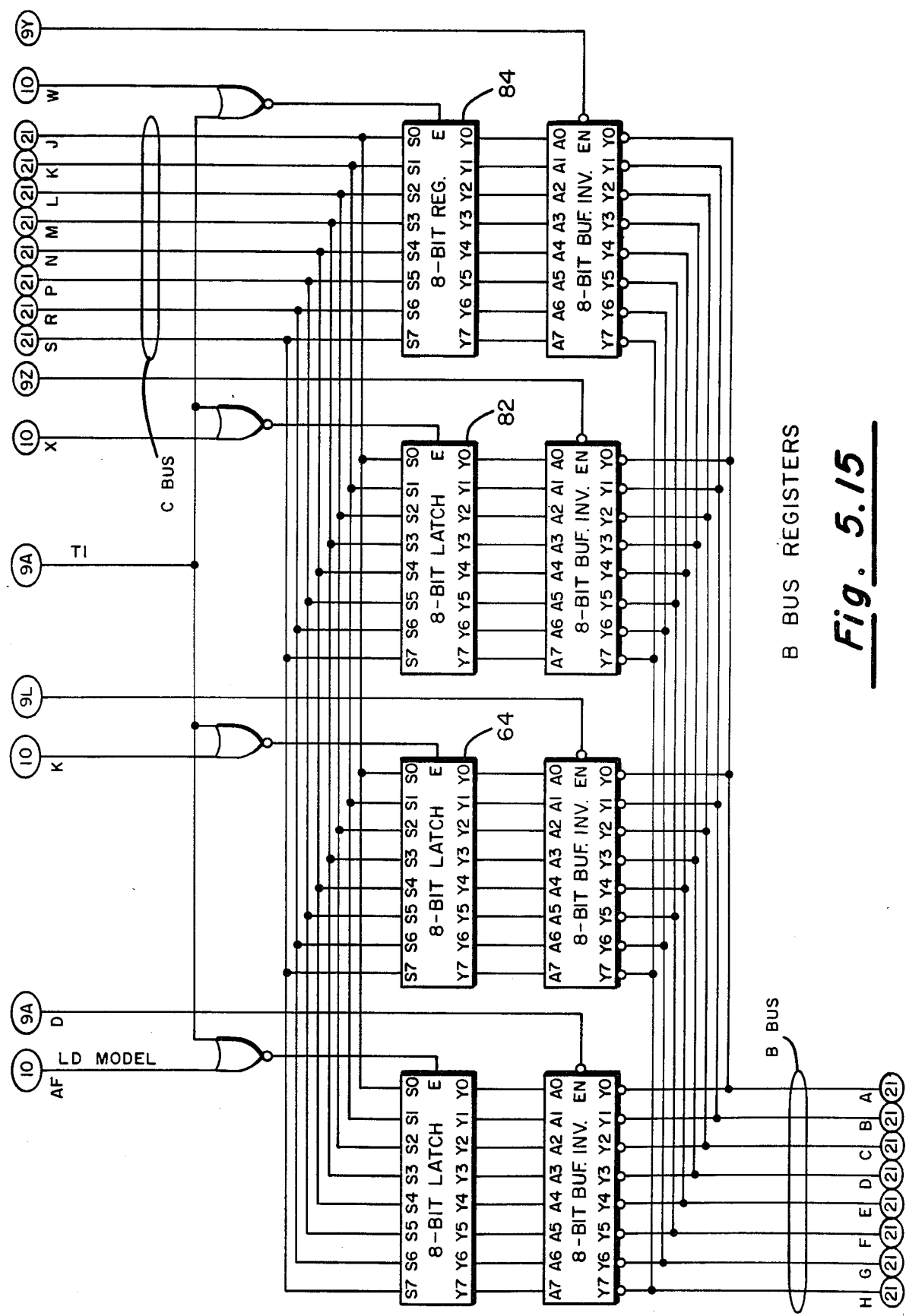
Fig. 5.15

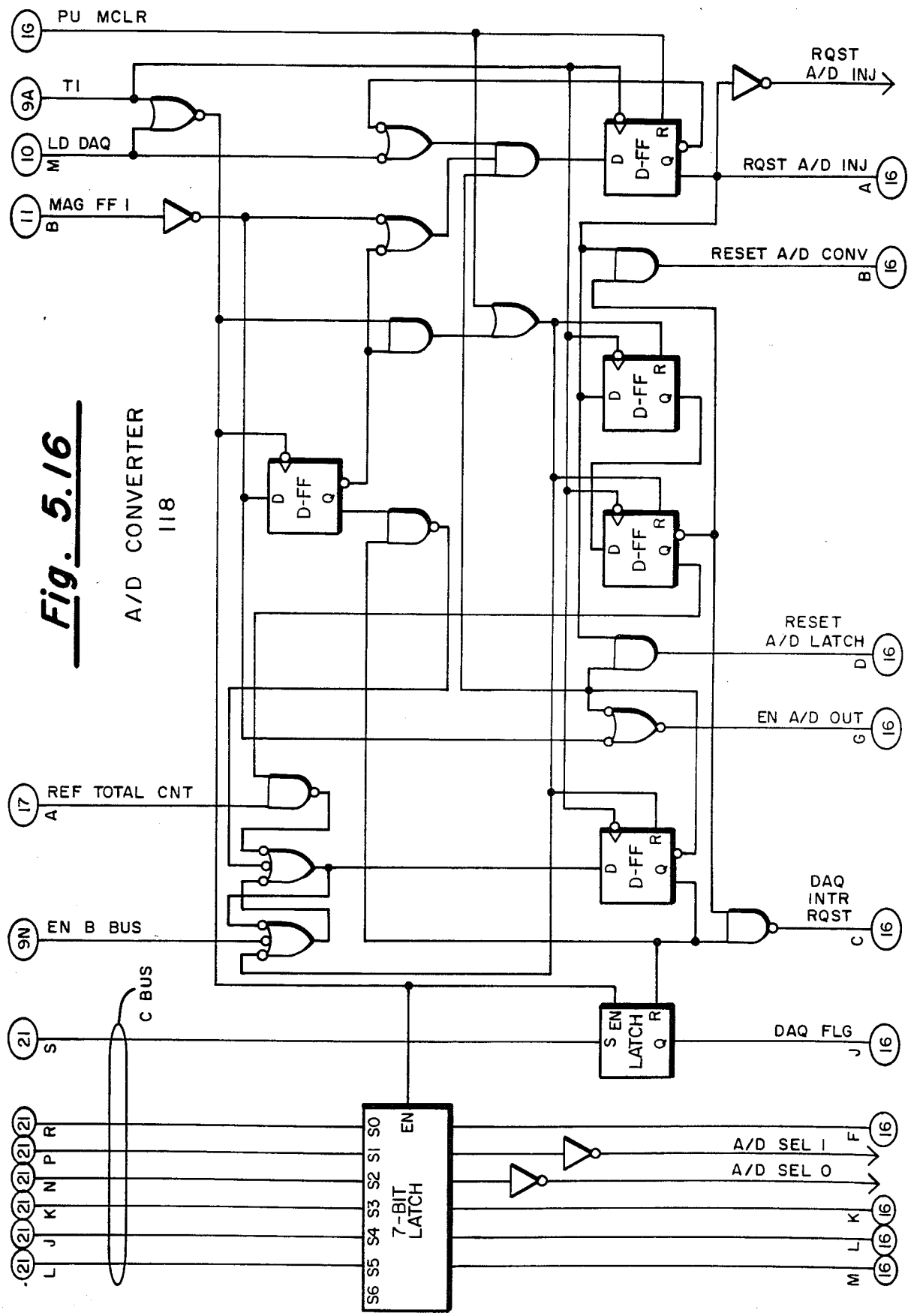
Fig. 5.16 A/D CONVERTER 118

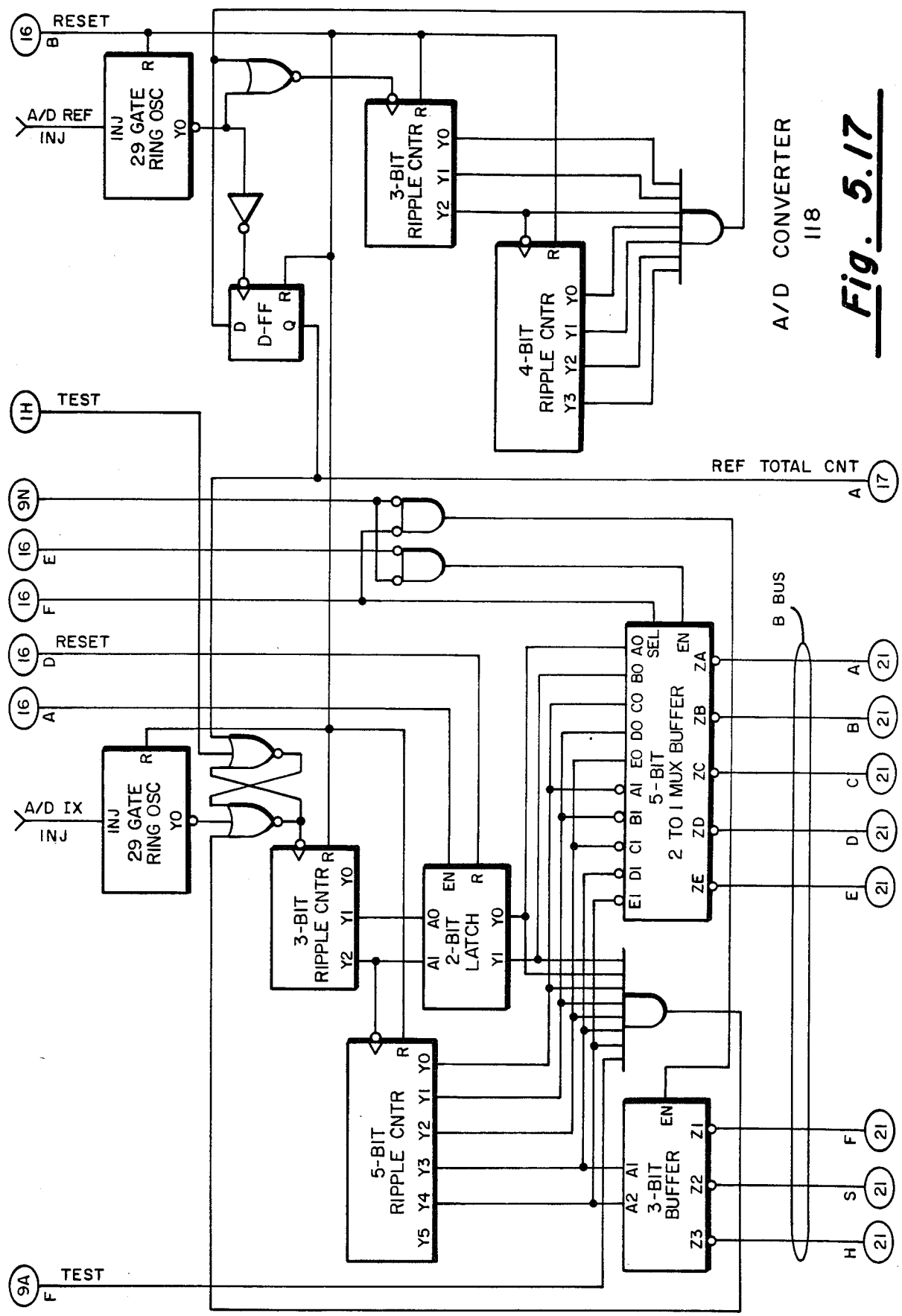
Fig. 5.17

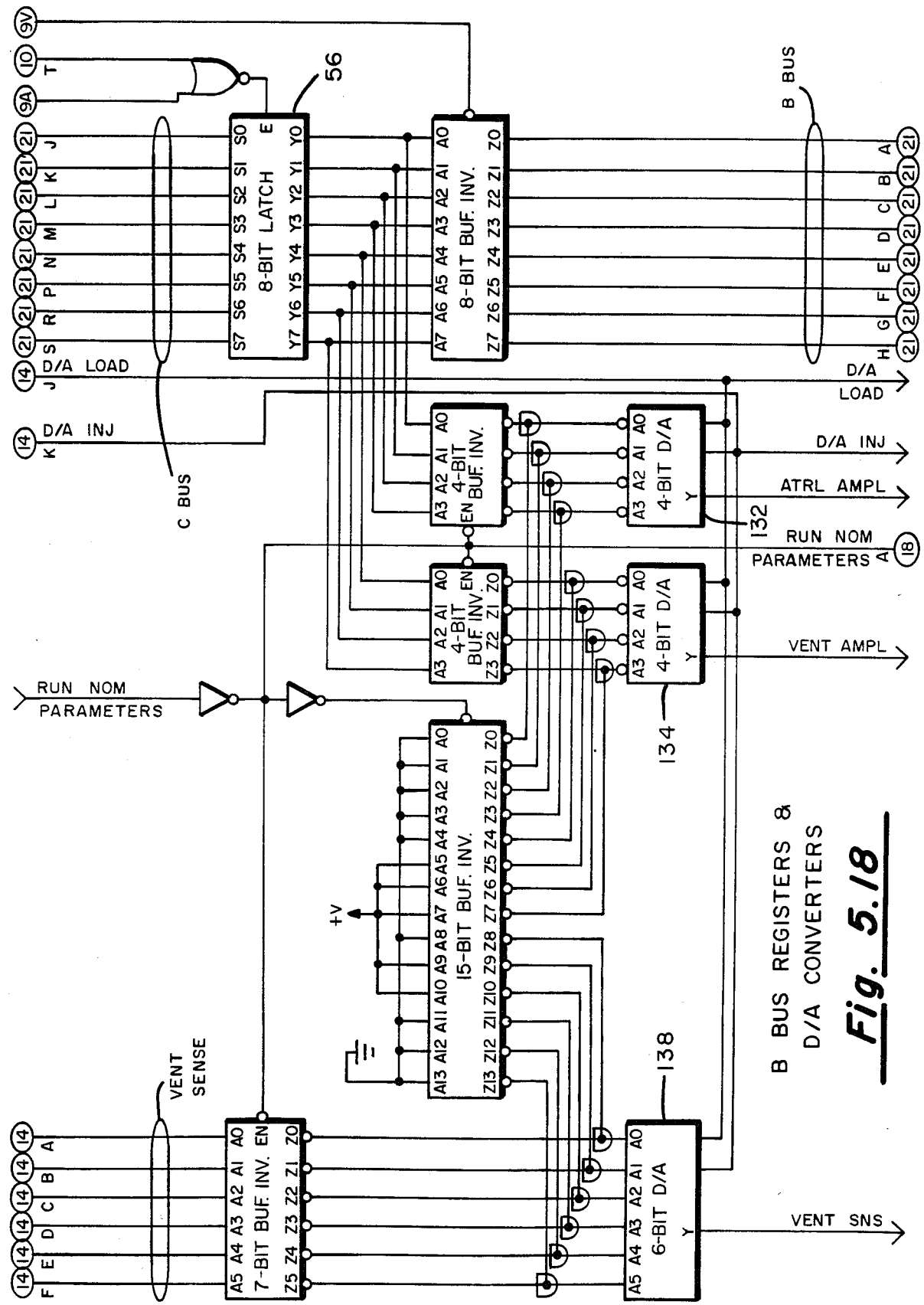

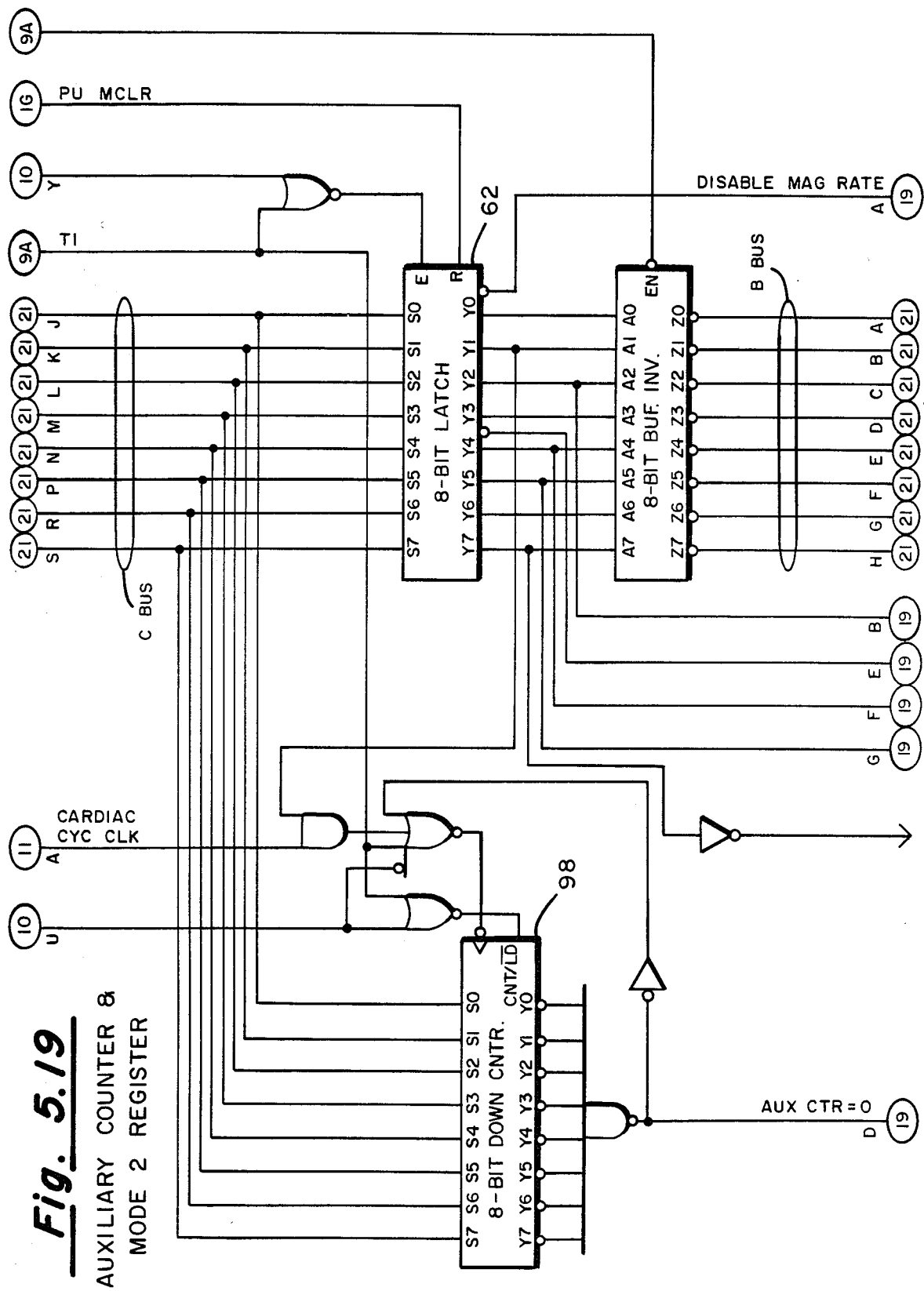

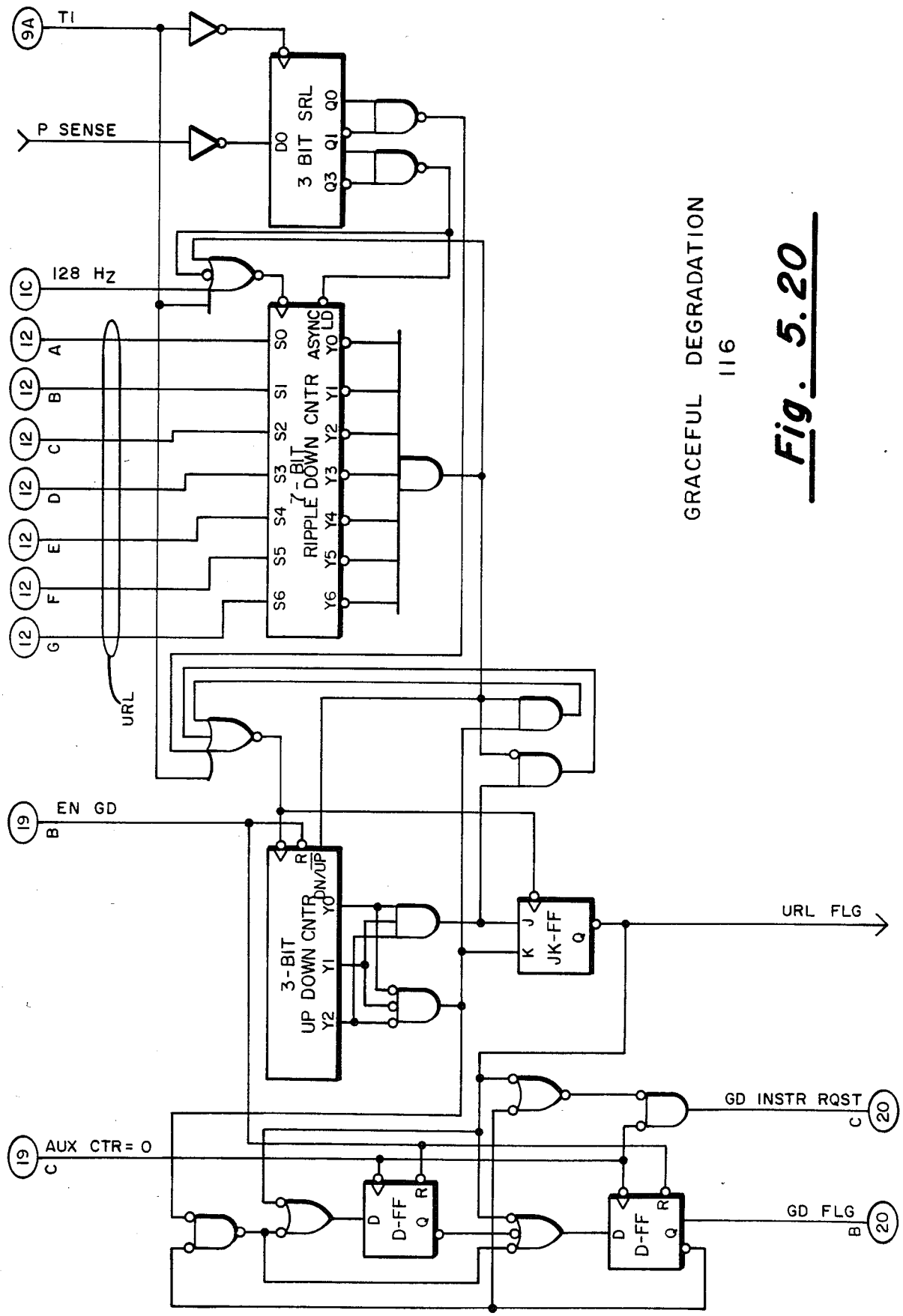
Fig. 5.20
GRACEFUL DEGRADATION 116

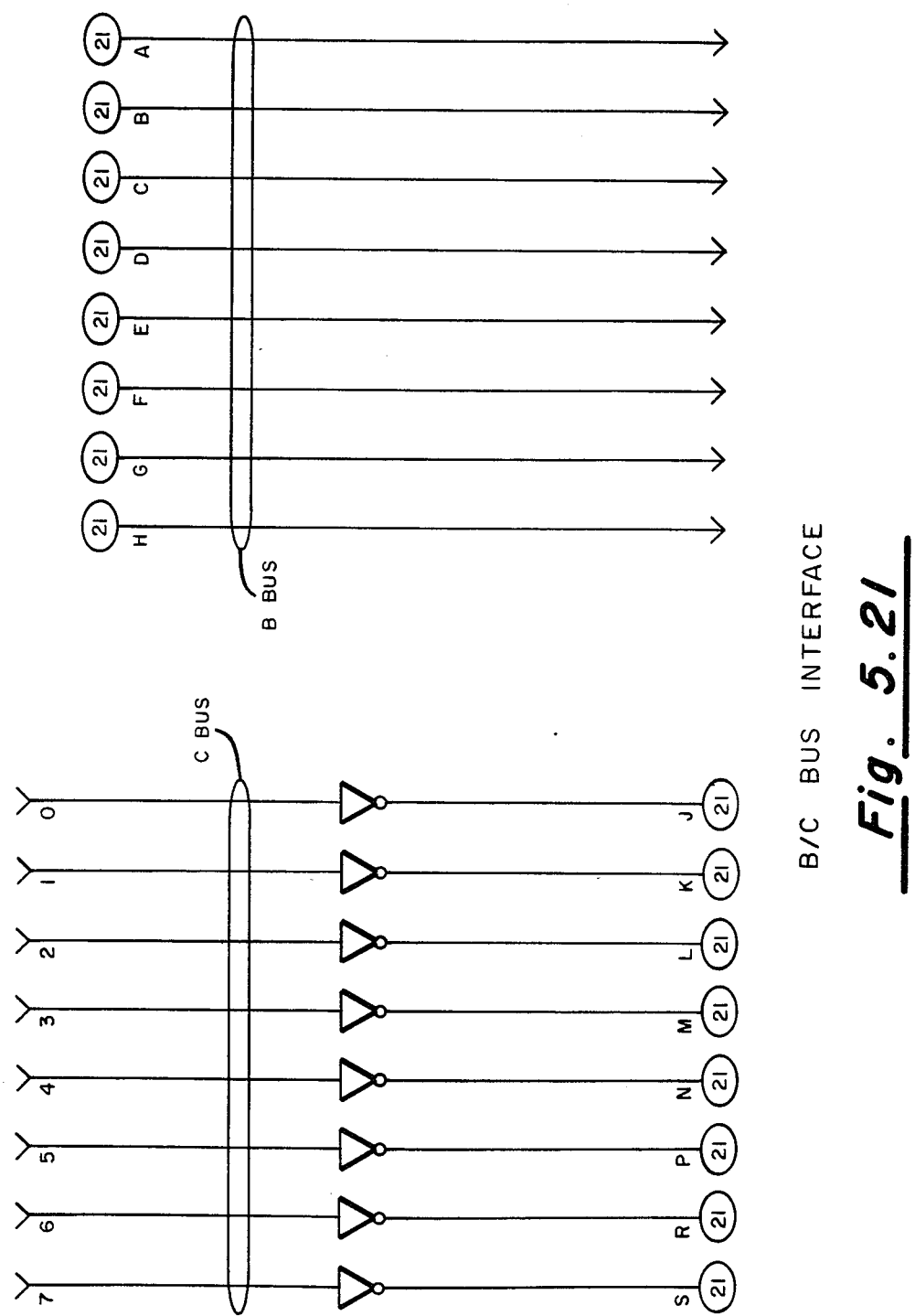
Fig. 5.21  B/C BUS INTERFACE

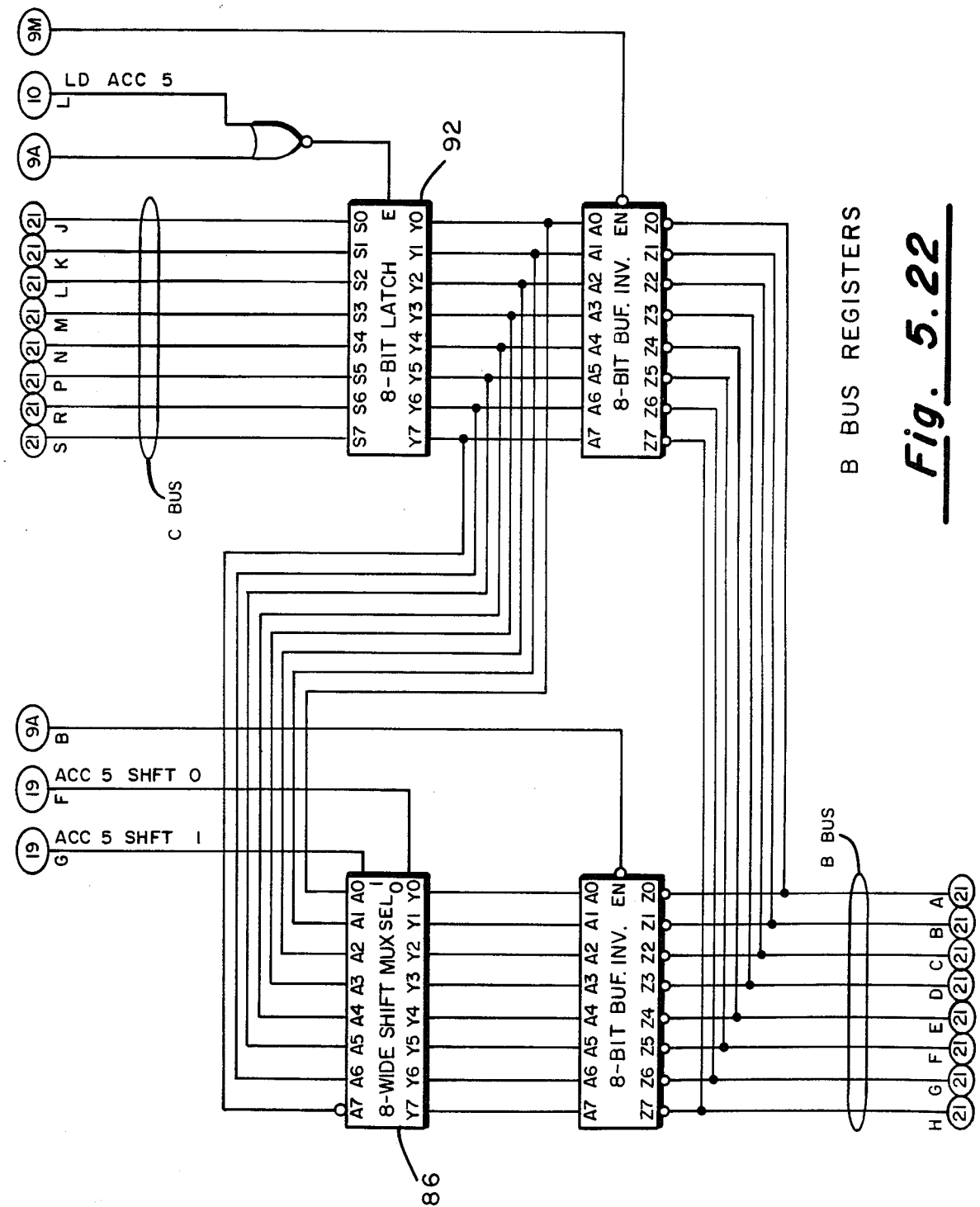
Fig. 5.22

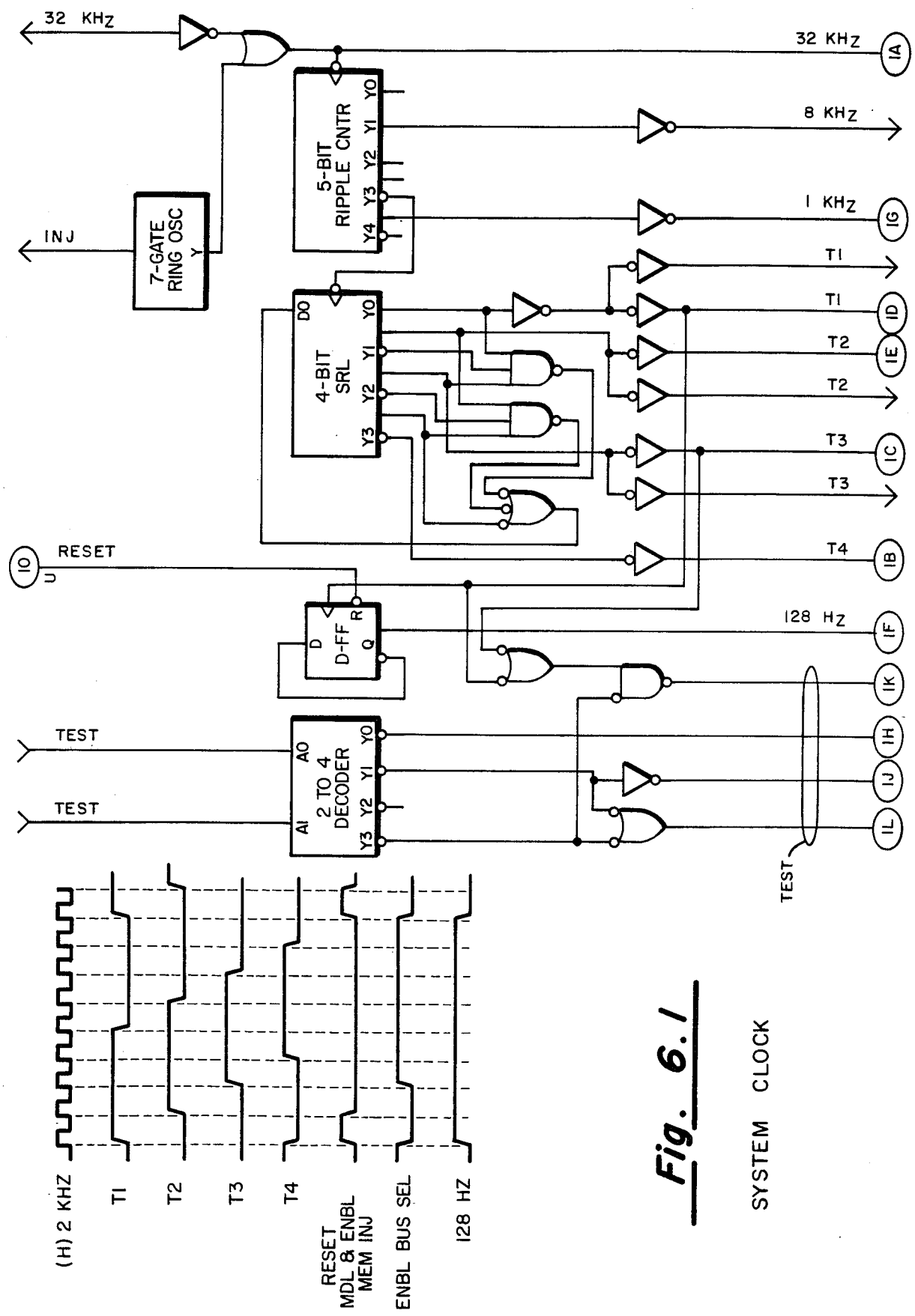
Fig. 6.1  SYSTEM CLOCK

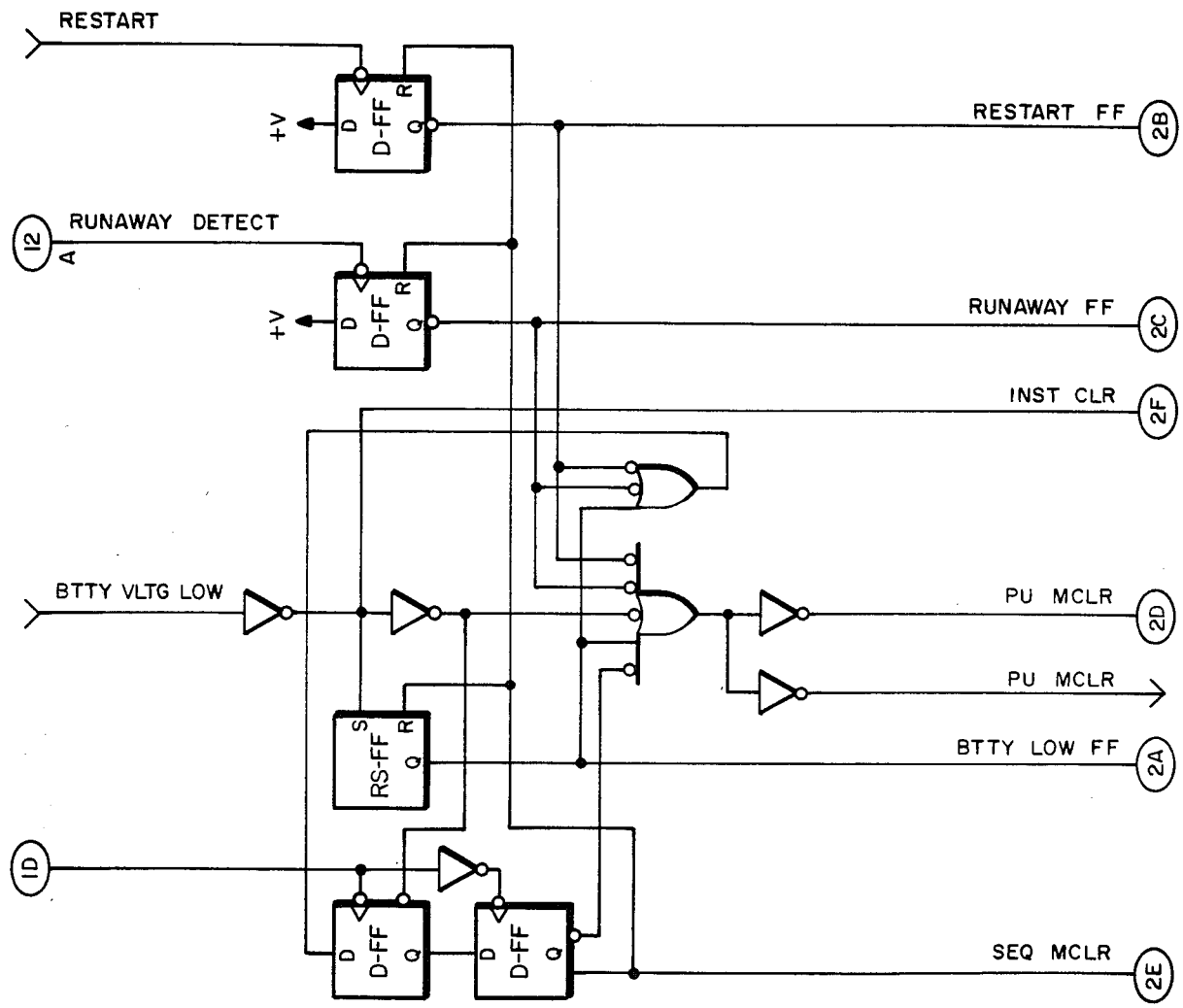
Fig. 6.2
POWER UP INSTRUCTION CYCLE CONTROL 19

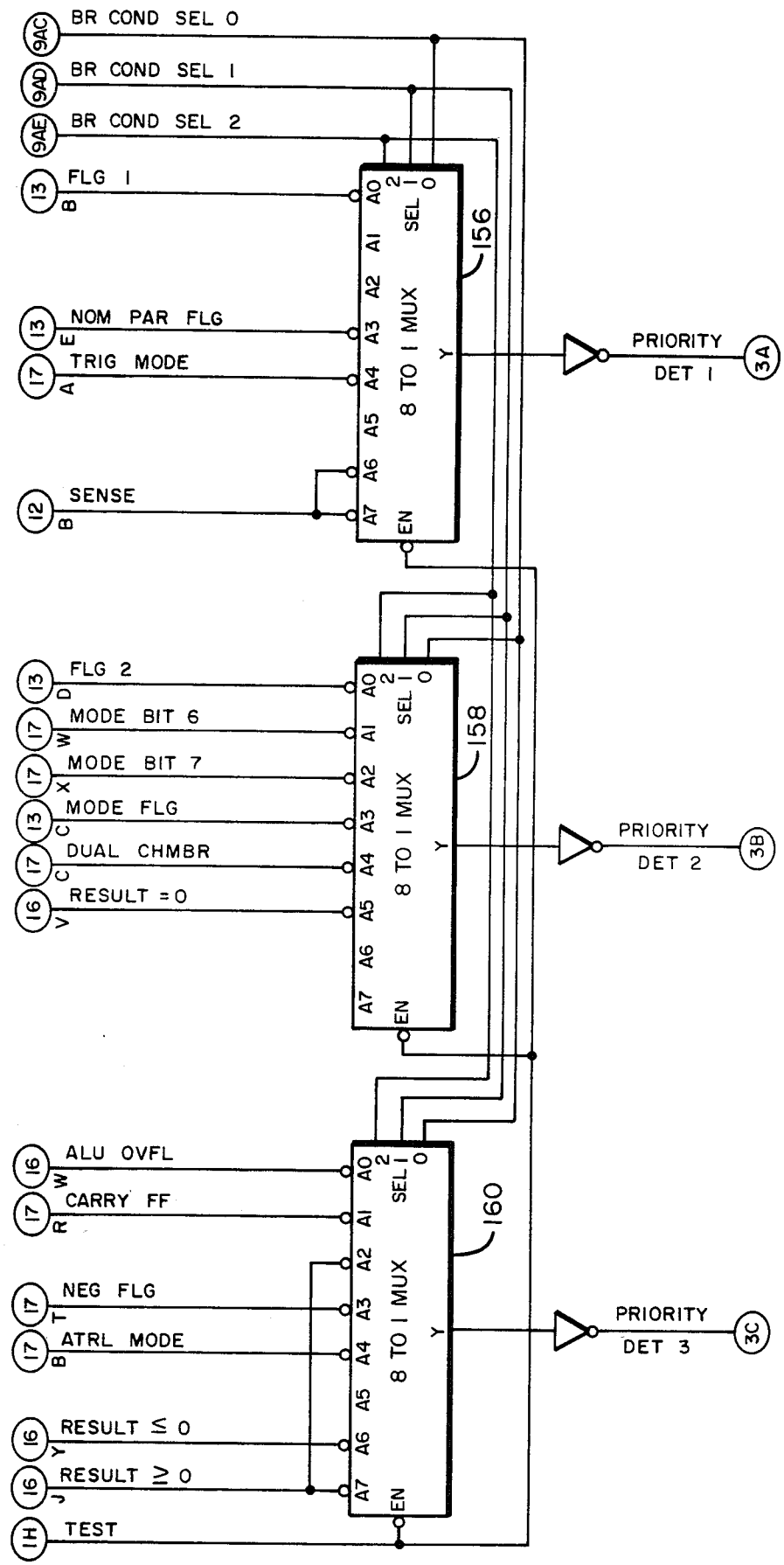
Fig. 6.3

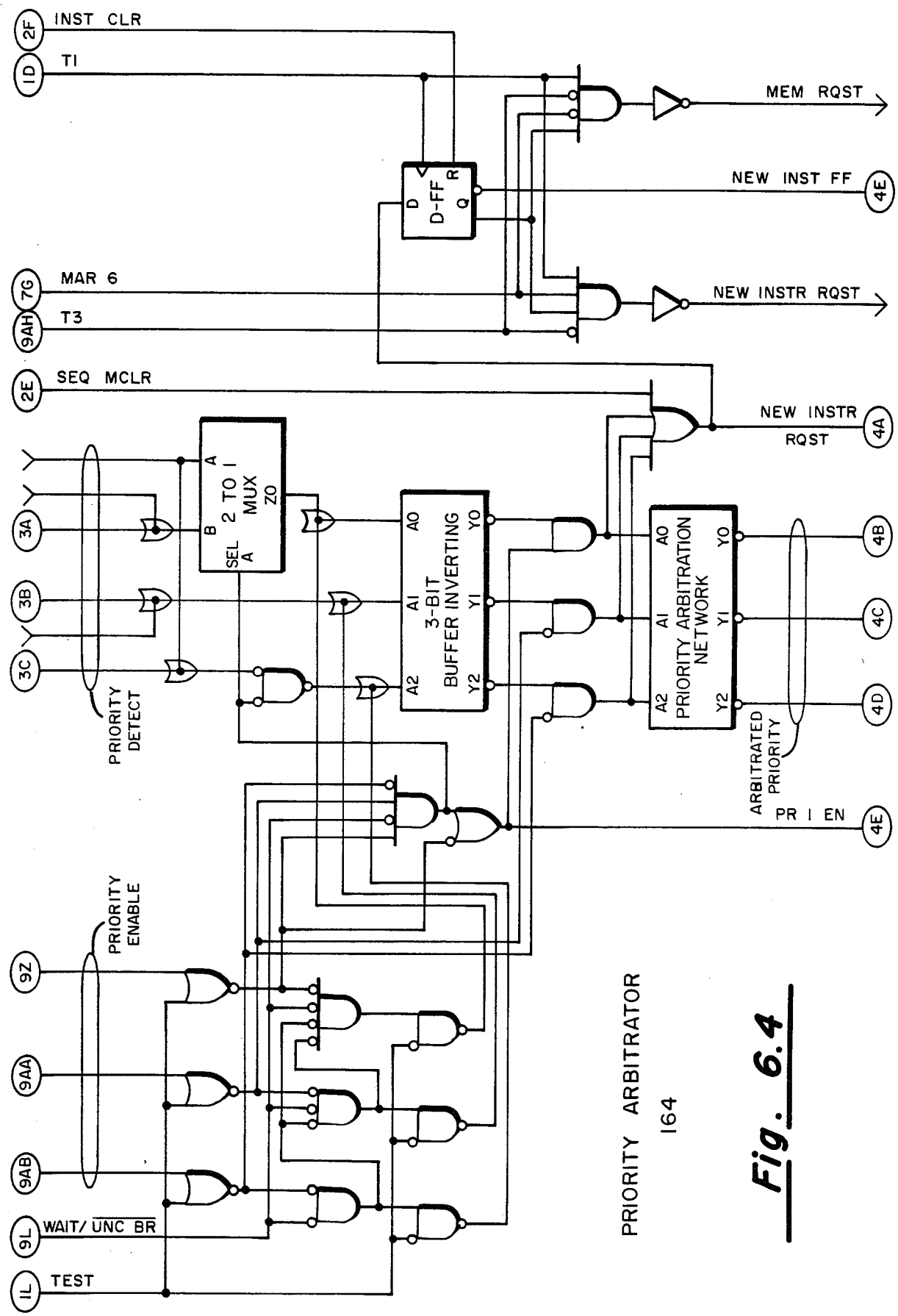

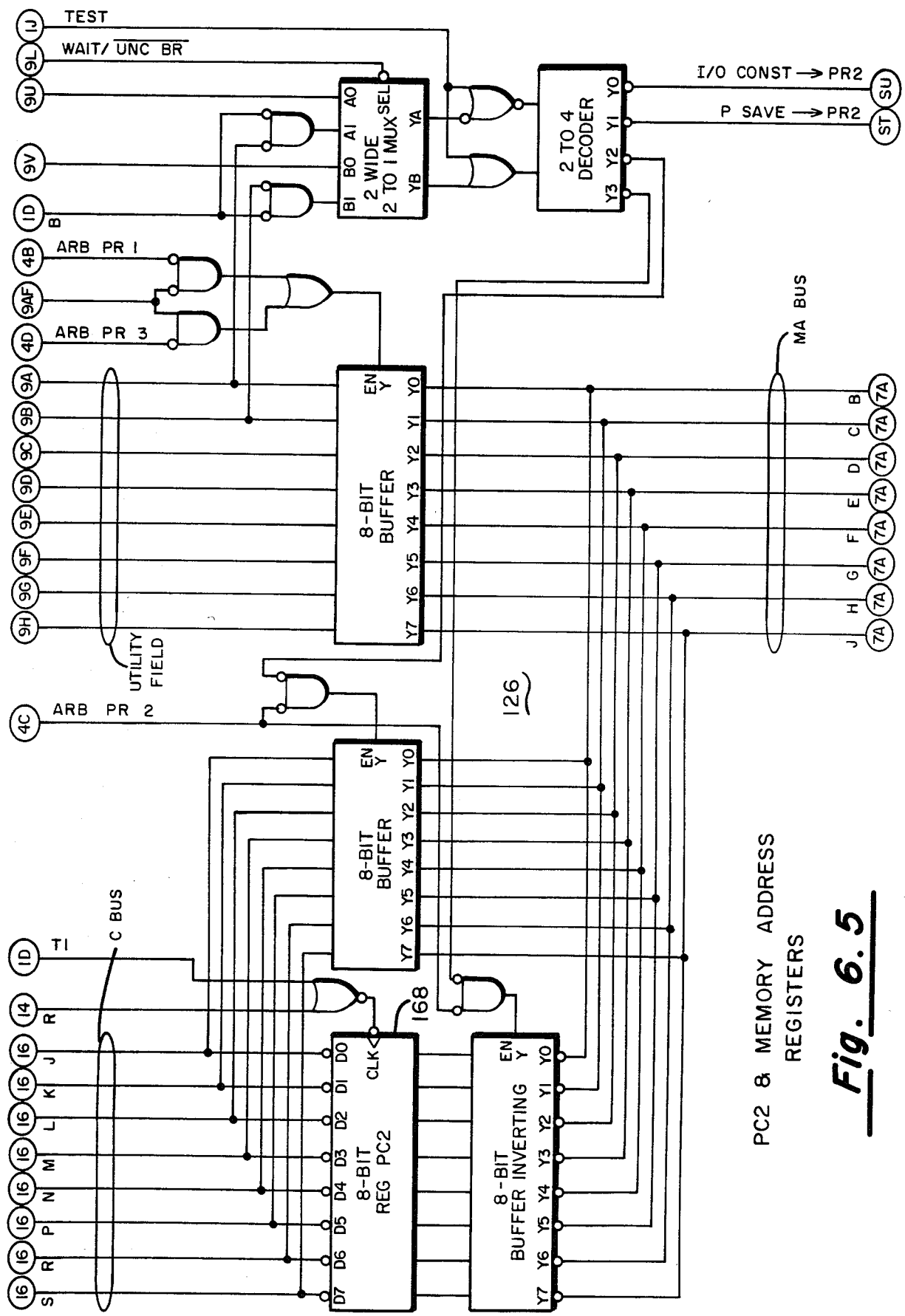
Fig. 6.5

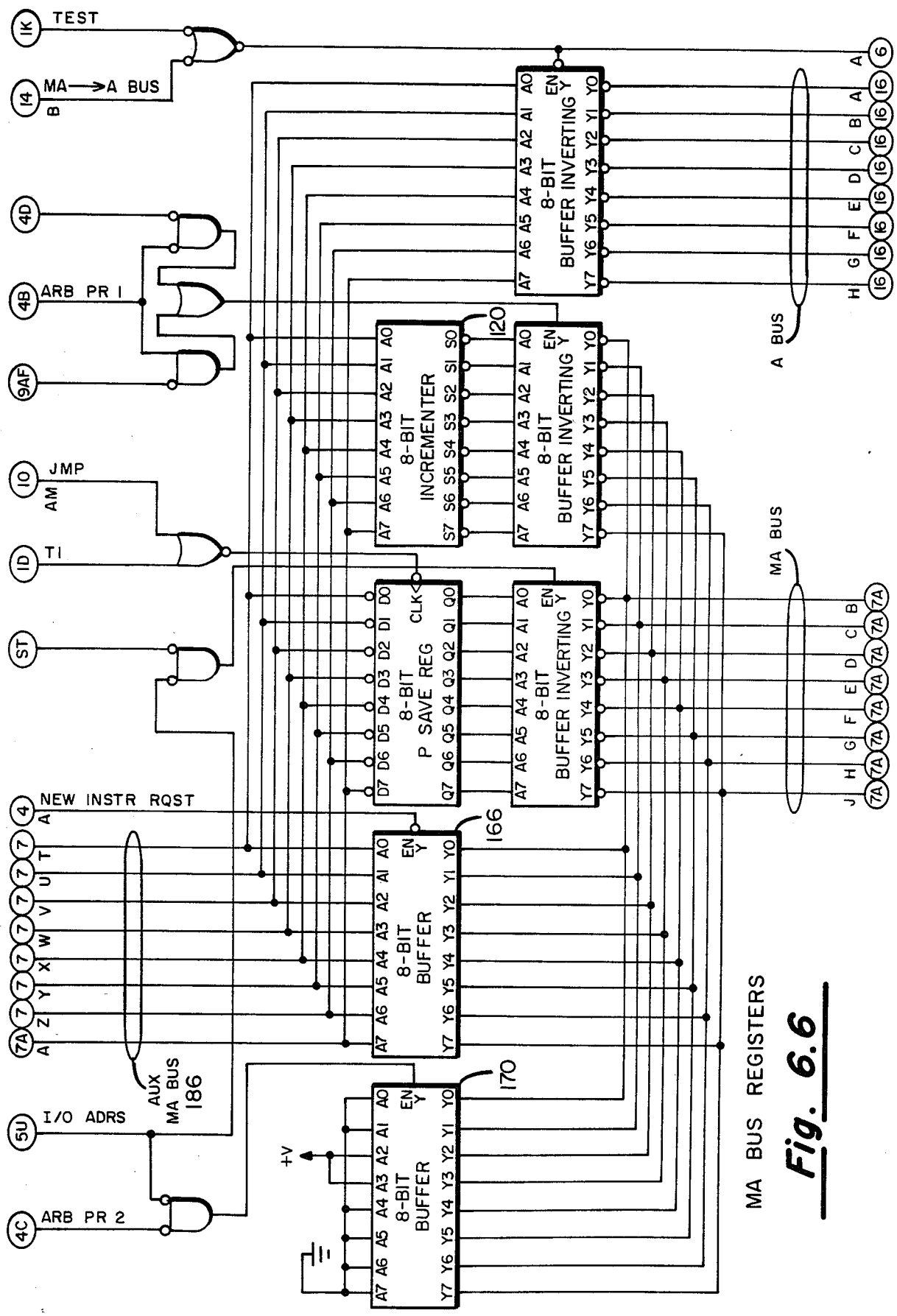
Fig. 6.6
MA BUS REGISTERS

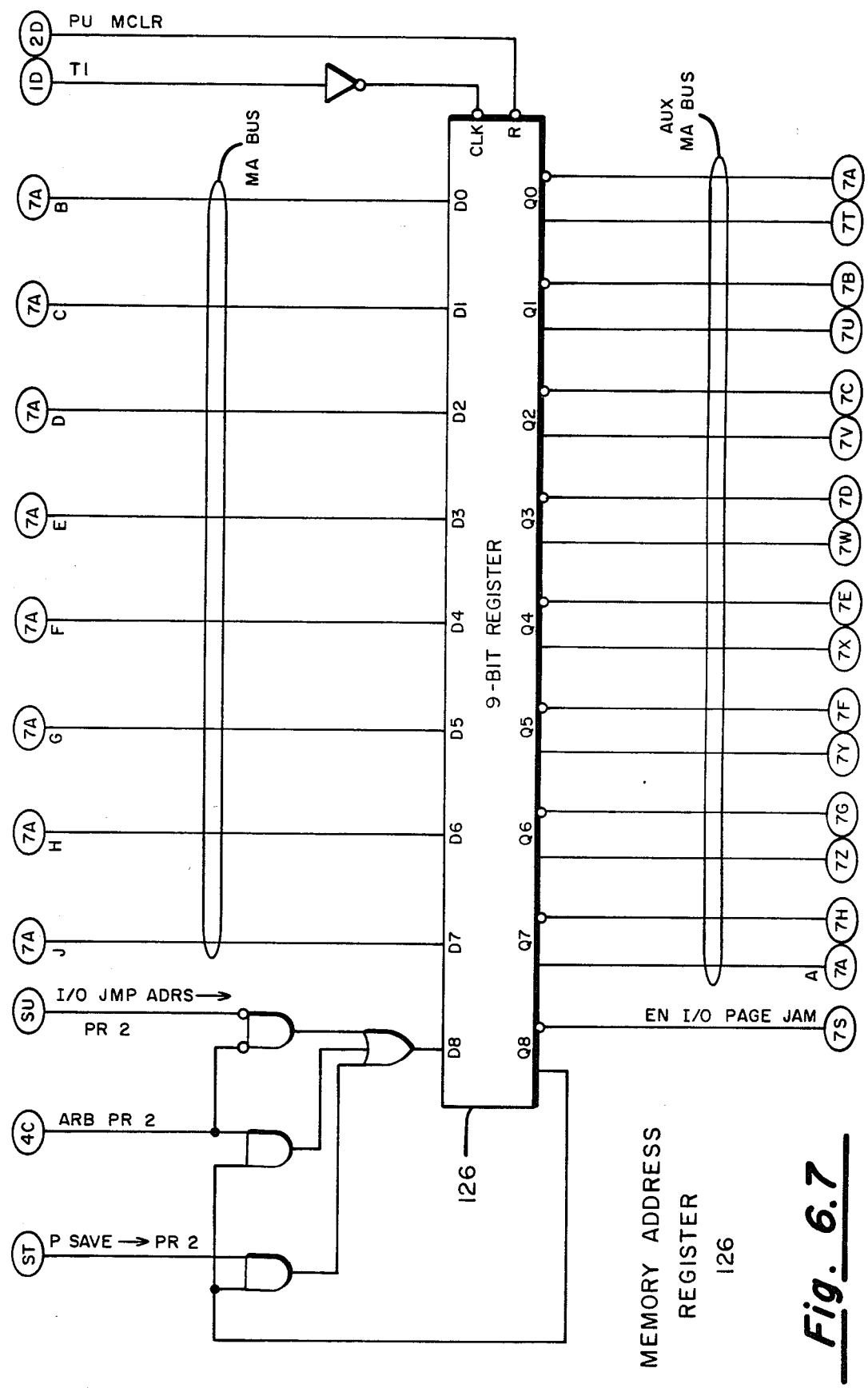
Fig. 6.7

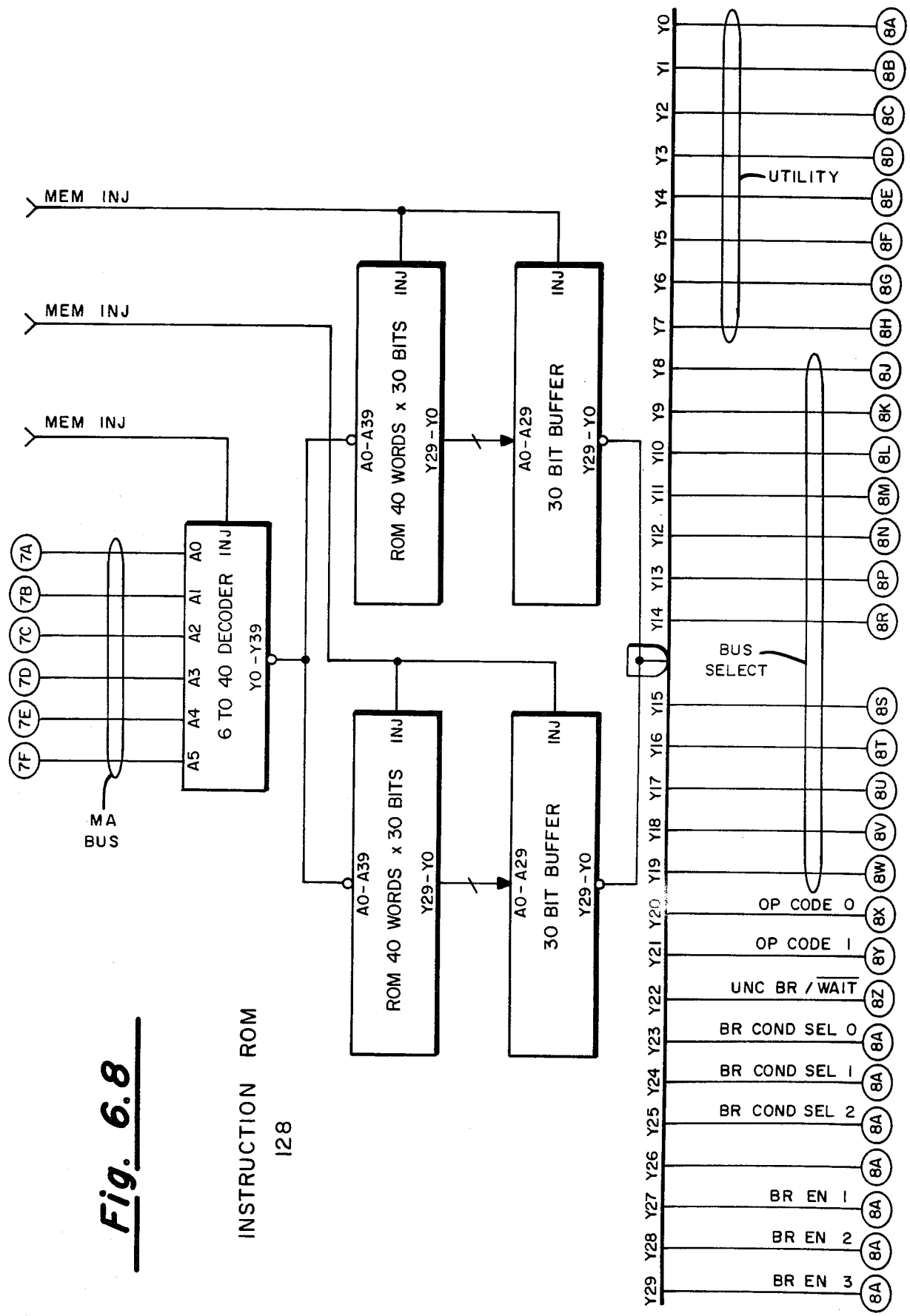
Fig. 6.8 INSTRUCTION ROM 128

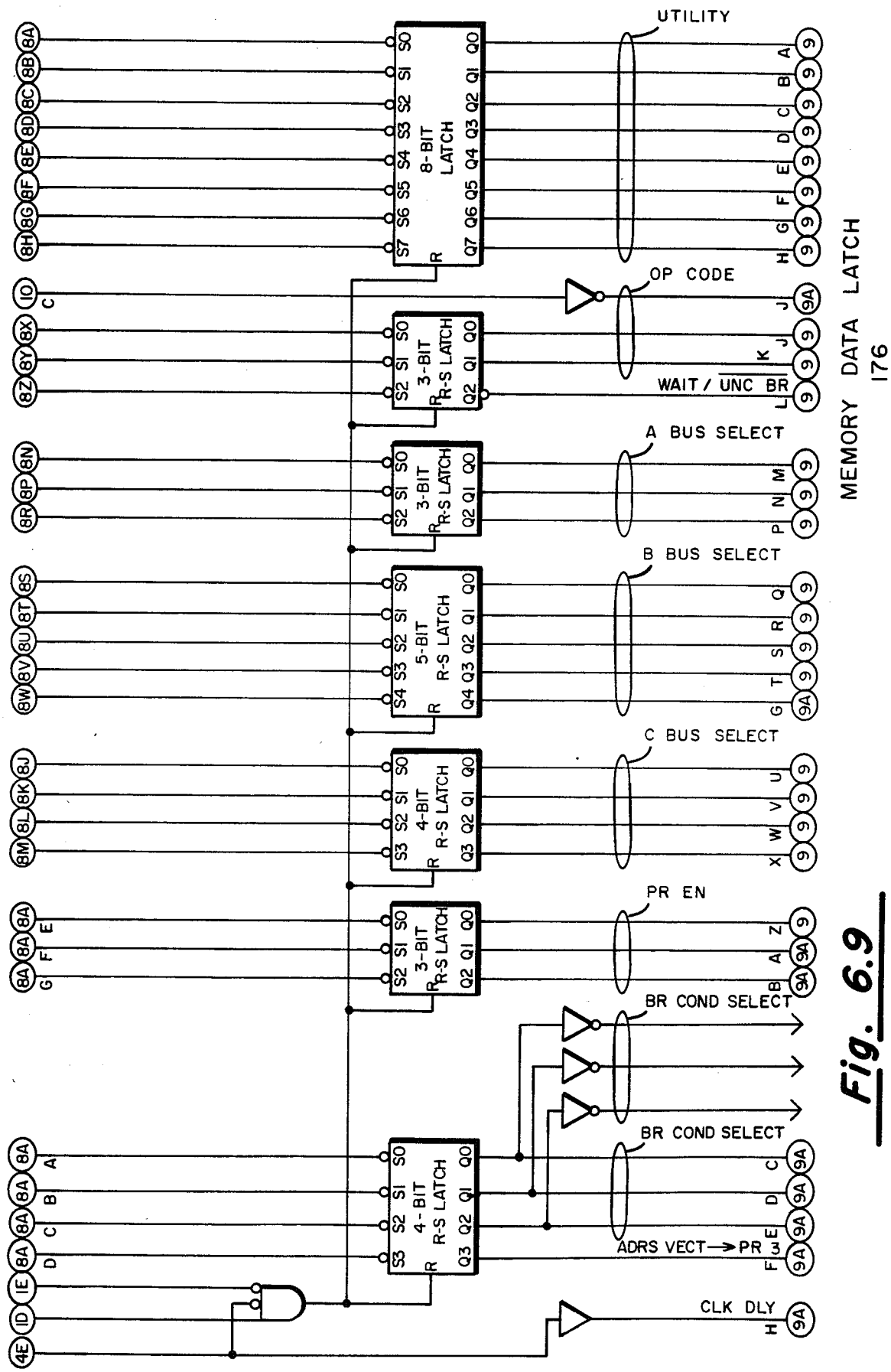

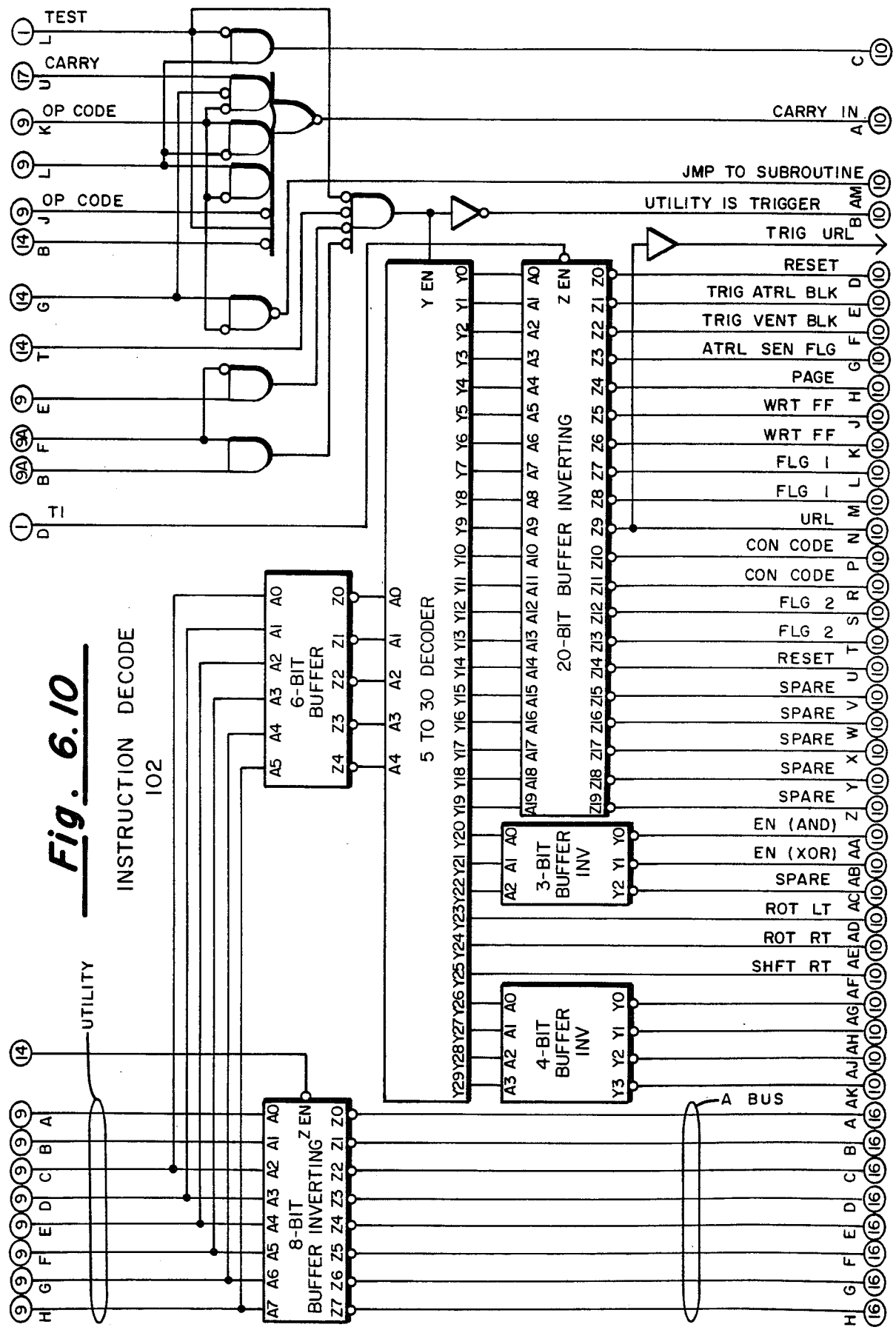
Fig. 6.10

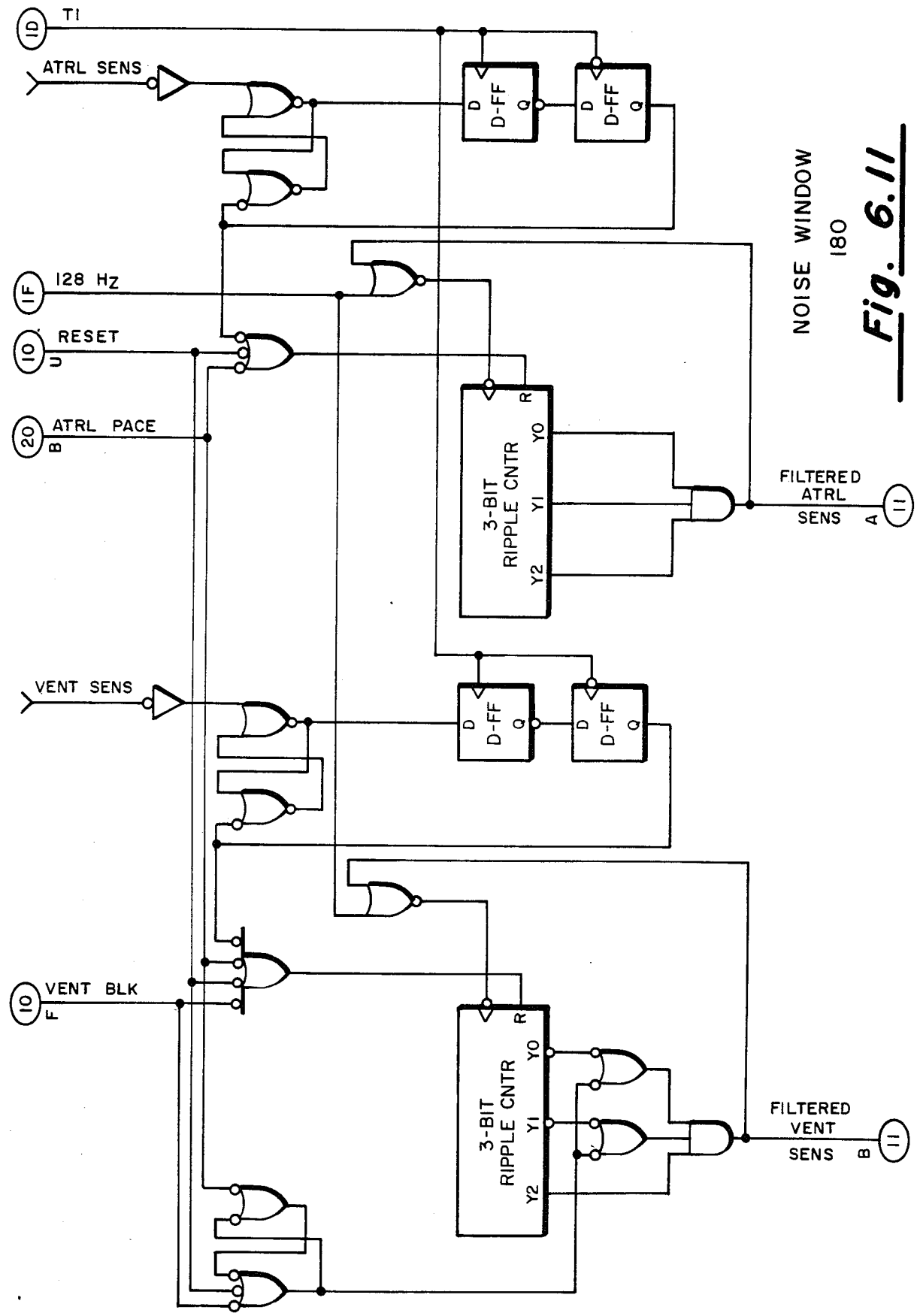
Fig. 6.11

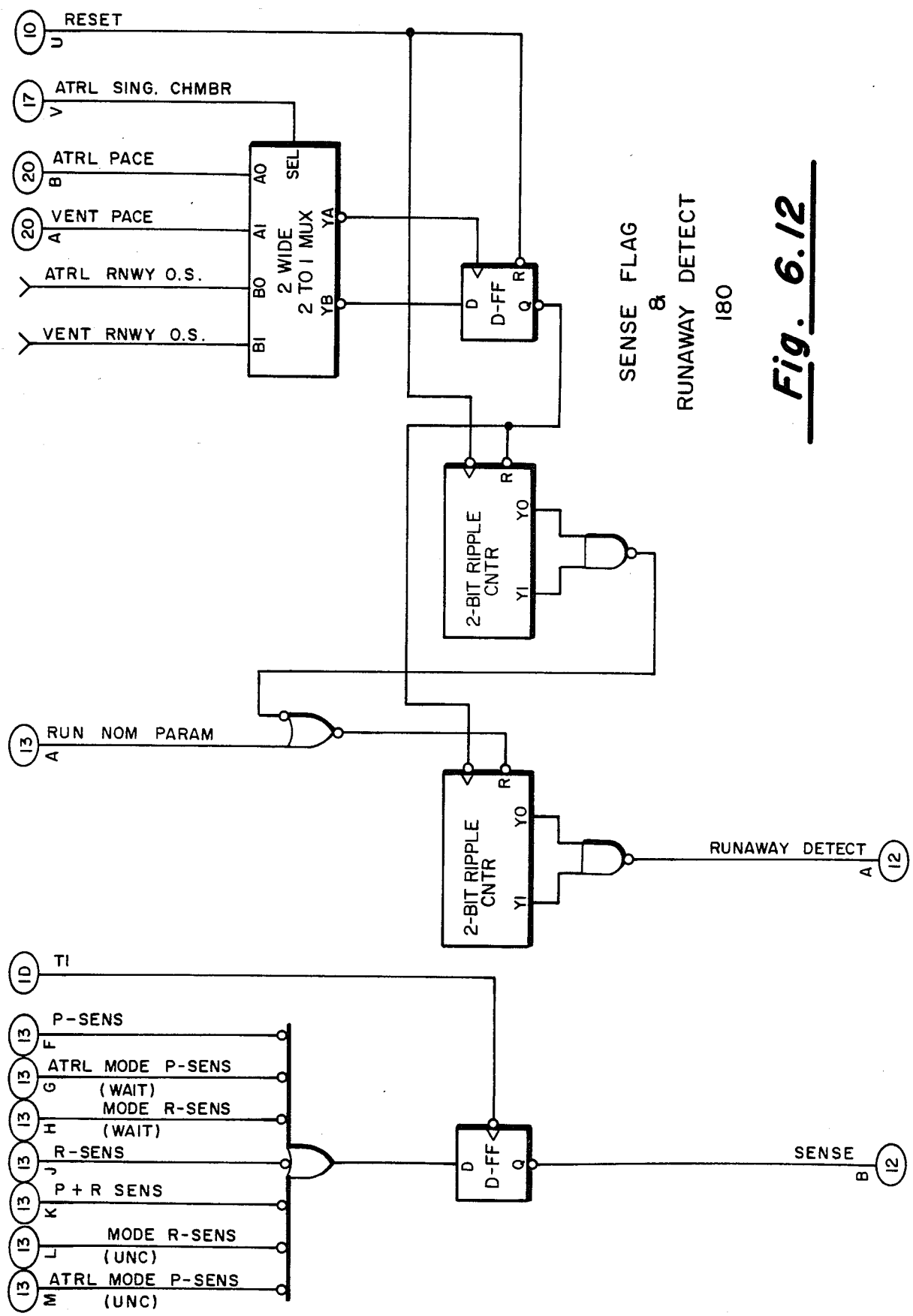
Fig. 6.12
SENSE FLAG & RUNAWAY DETECT 180

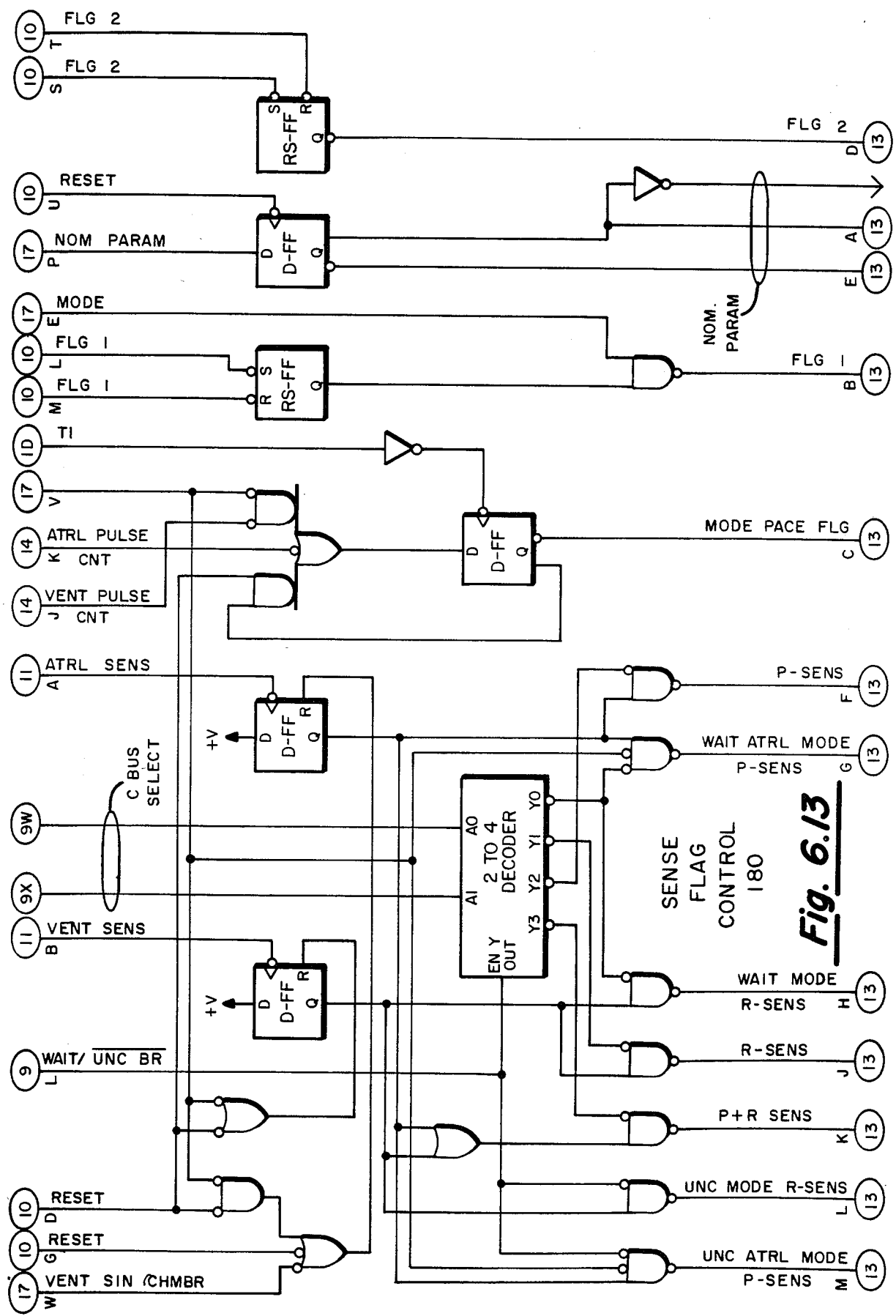
Fig. 6.13

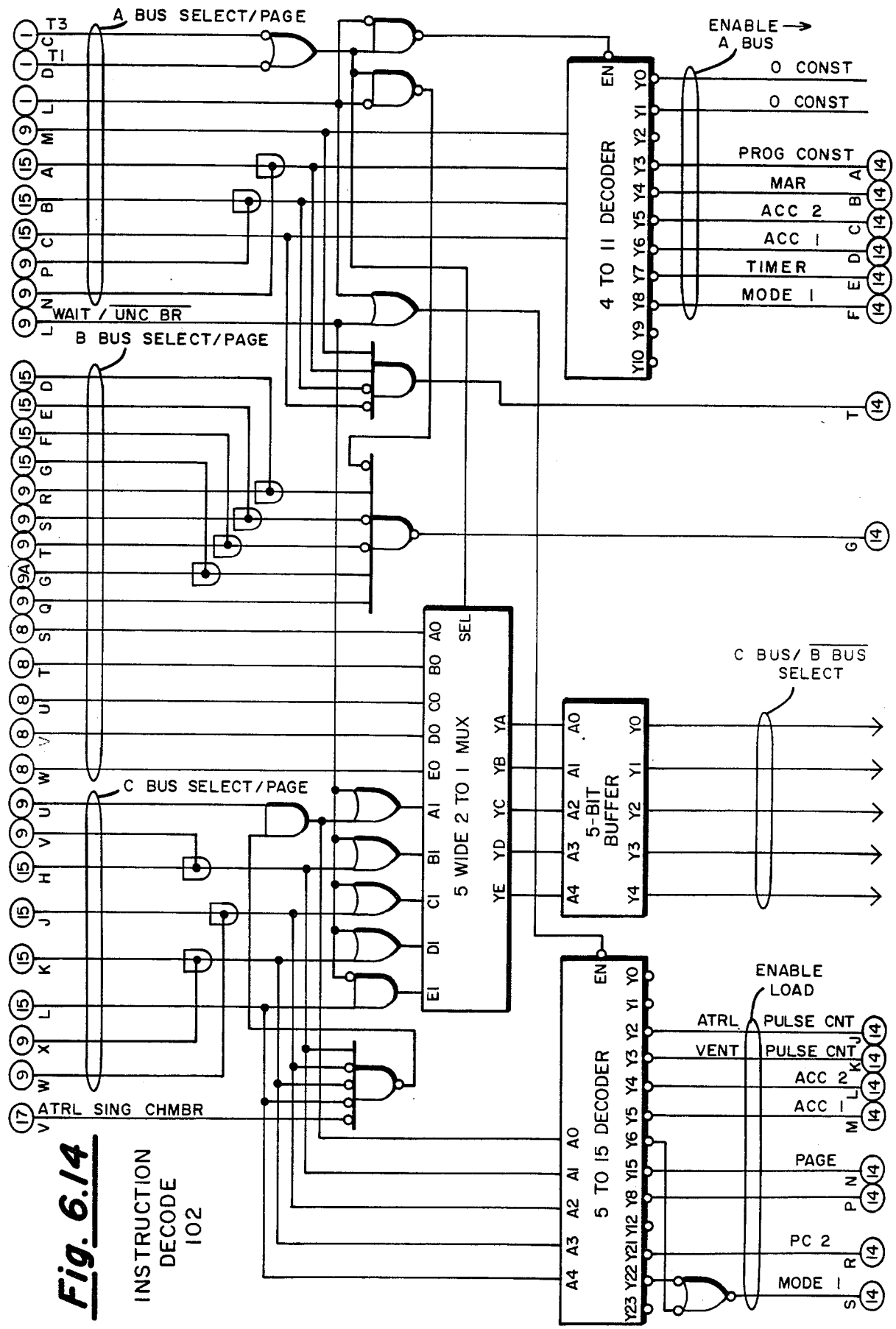
Fig. 6.14 INSTRUCTION DECODE 102

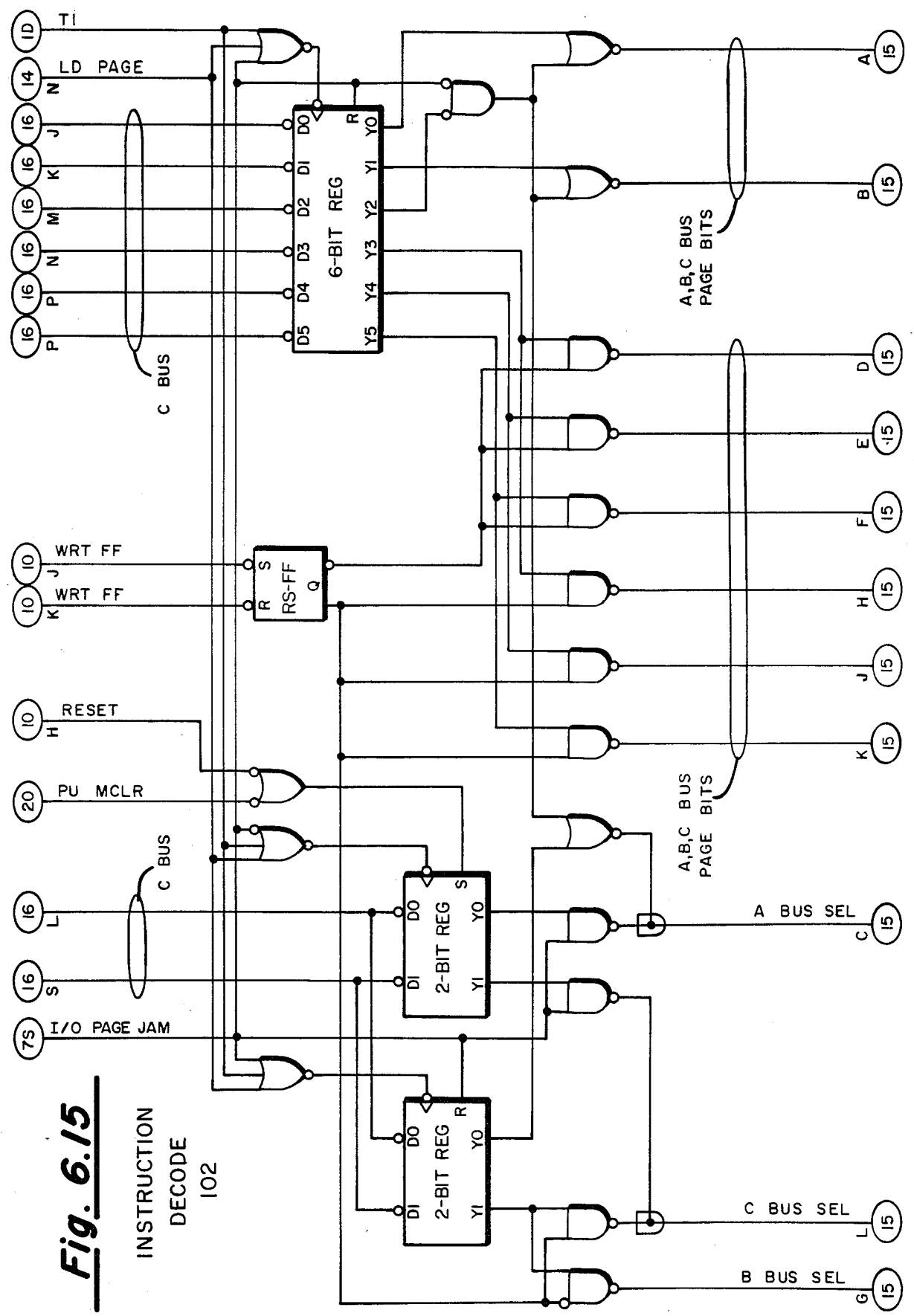

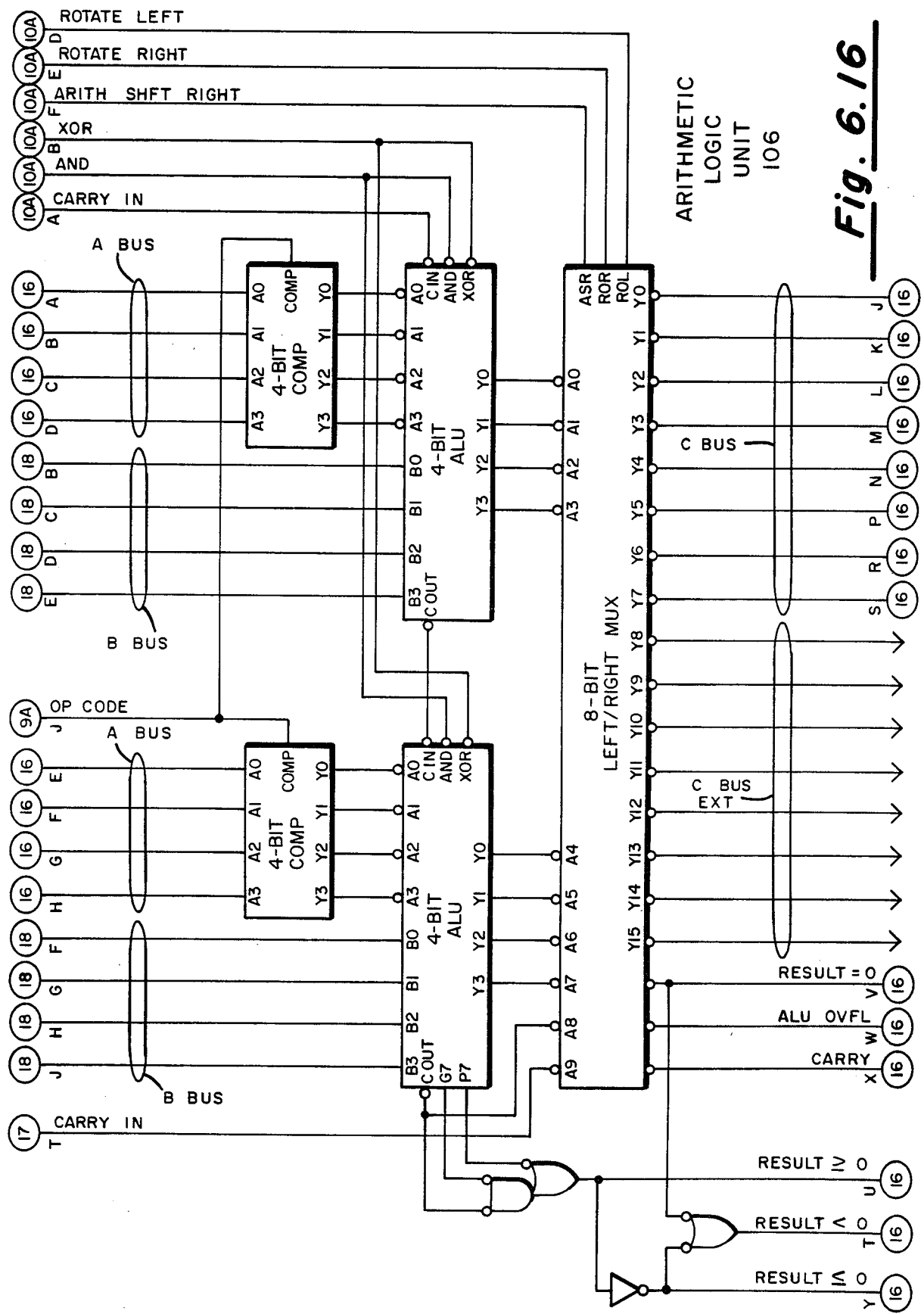
Fig. 6.16

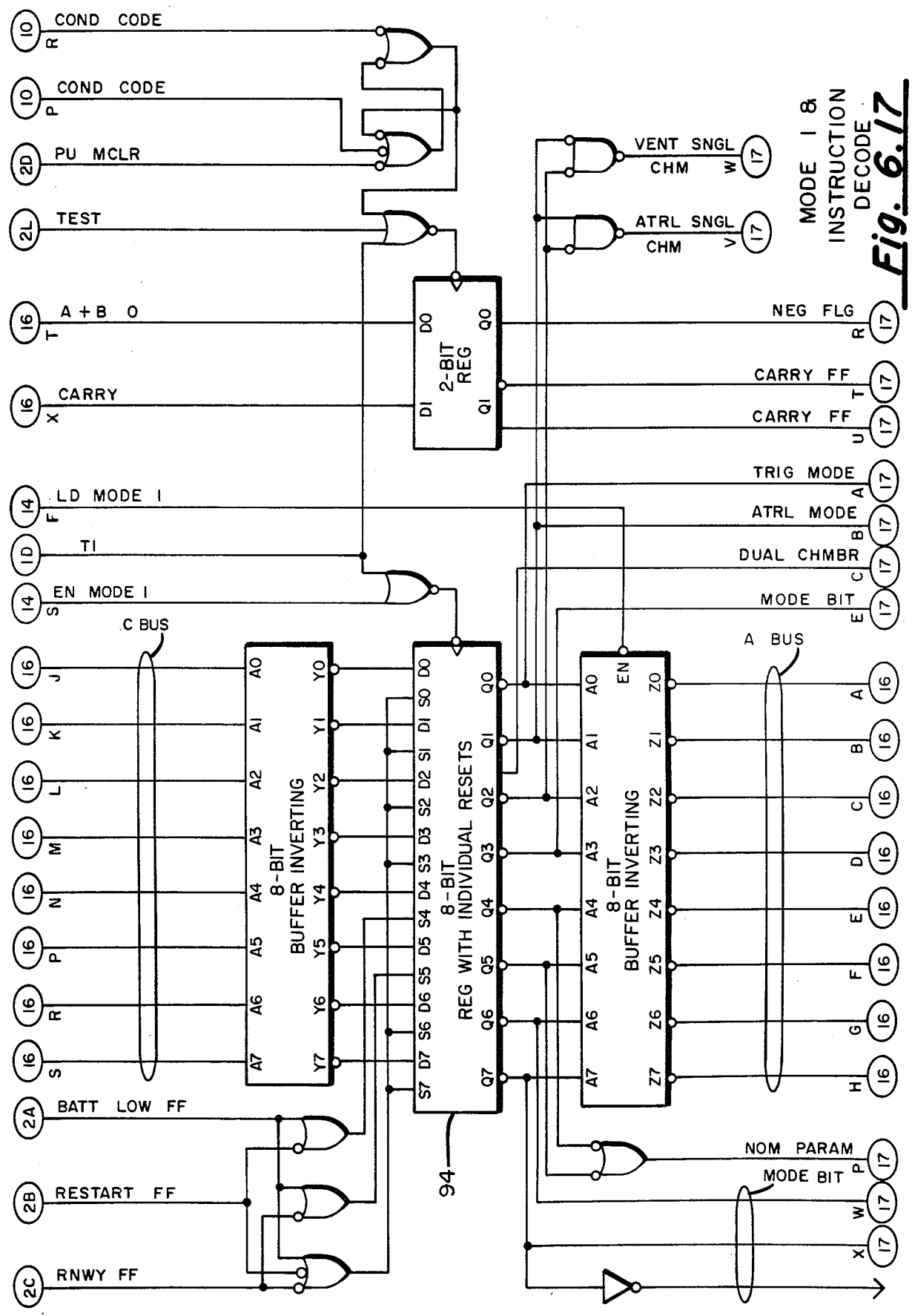

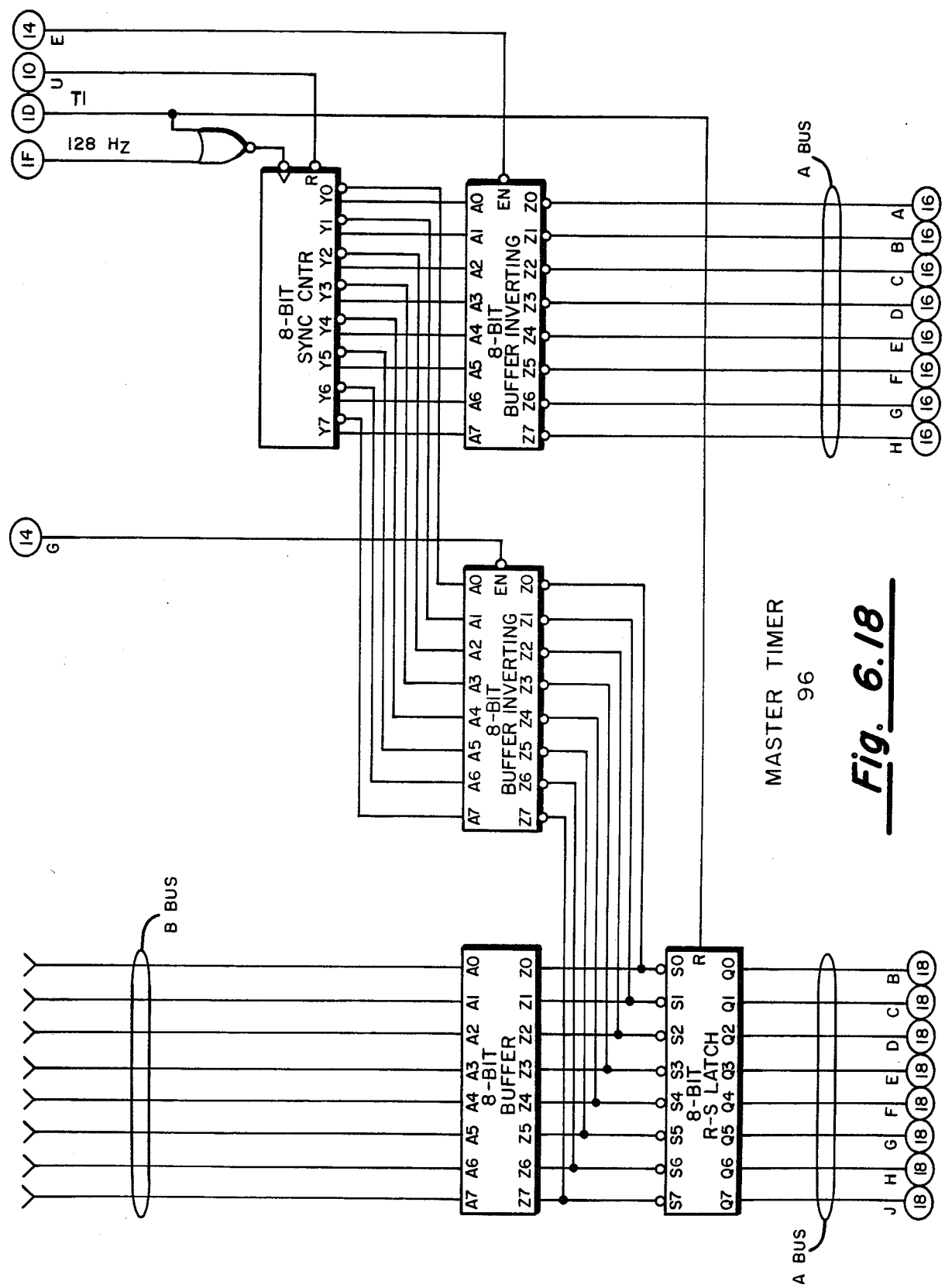
Fig. 6.18

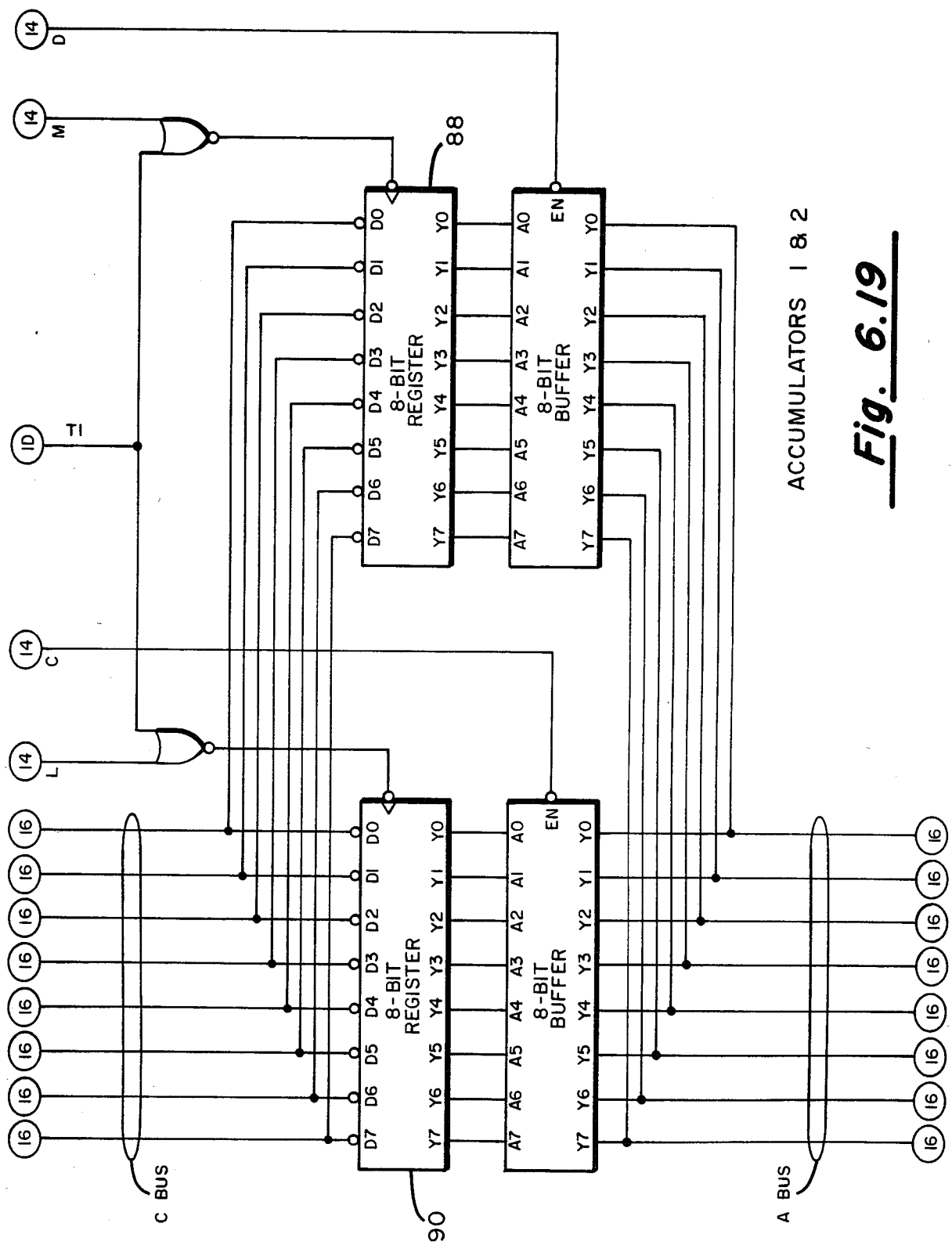
Fig. 6.19
ACCUMULATORS 1 & 2

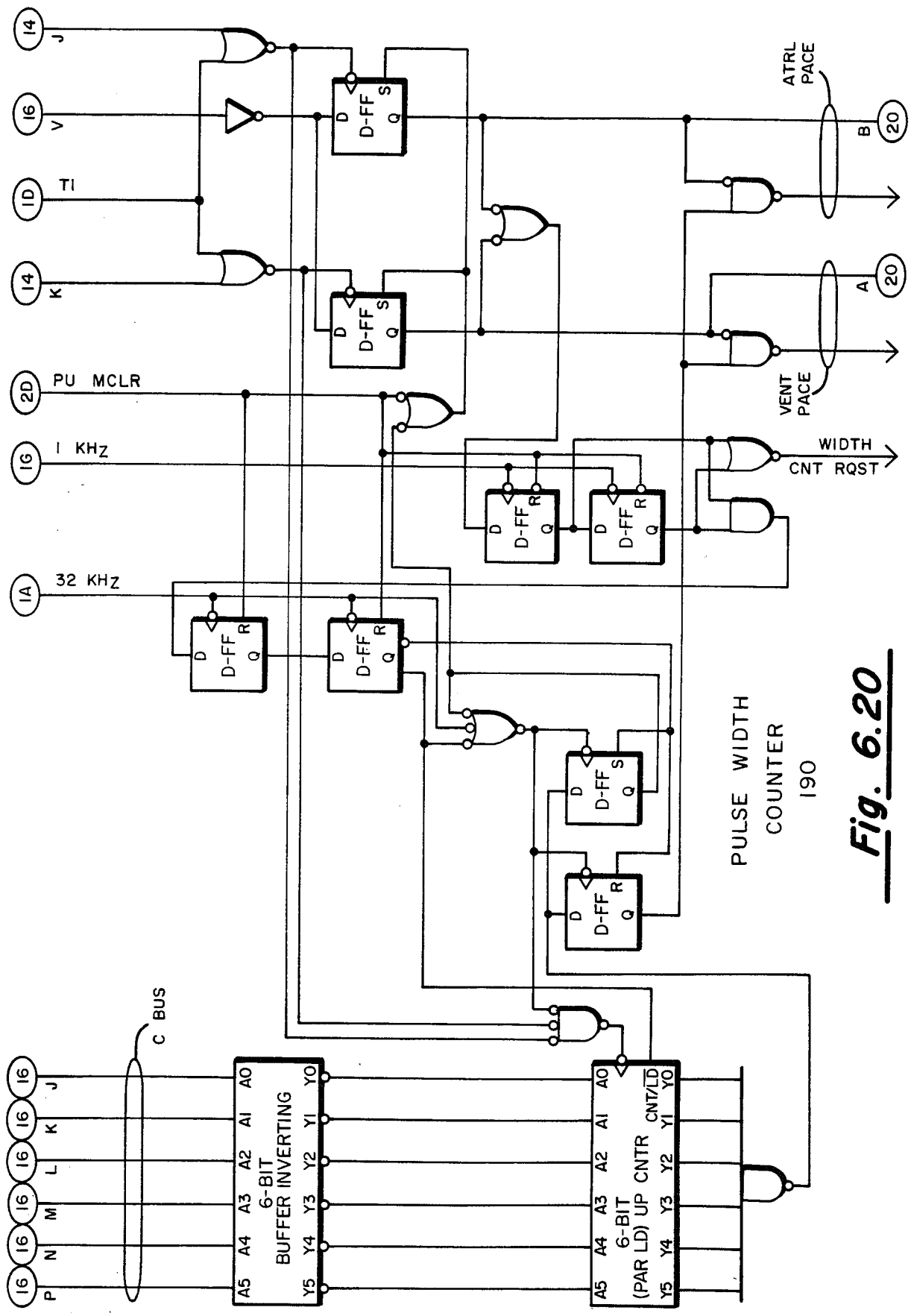
Fig. 6.20

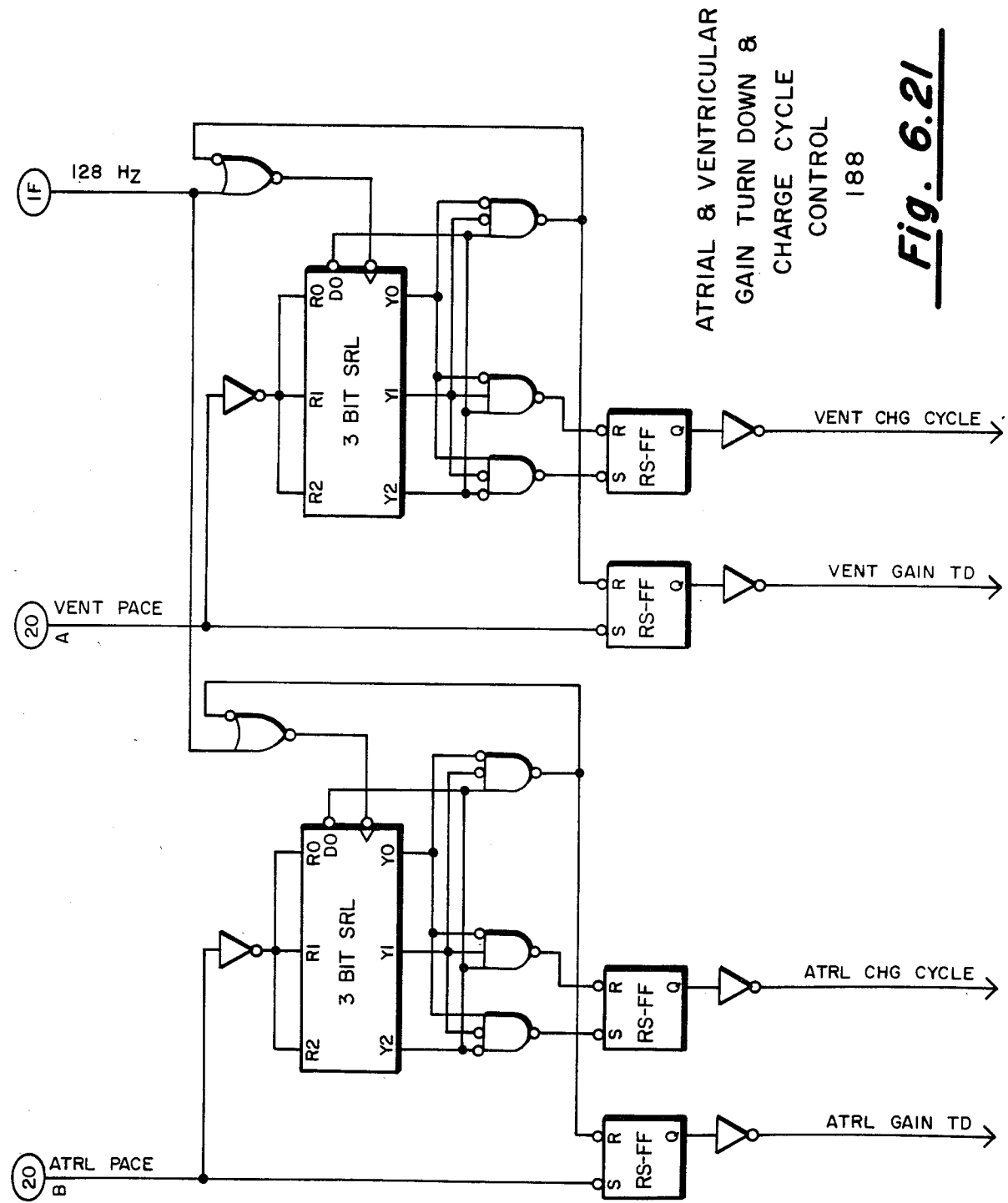

UPPER RATE LIMIT SIMULATION WITHOUT RATE SMOOTHING

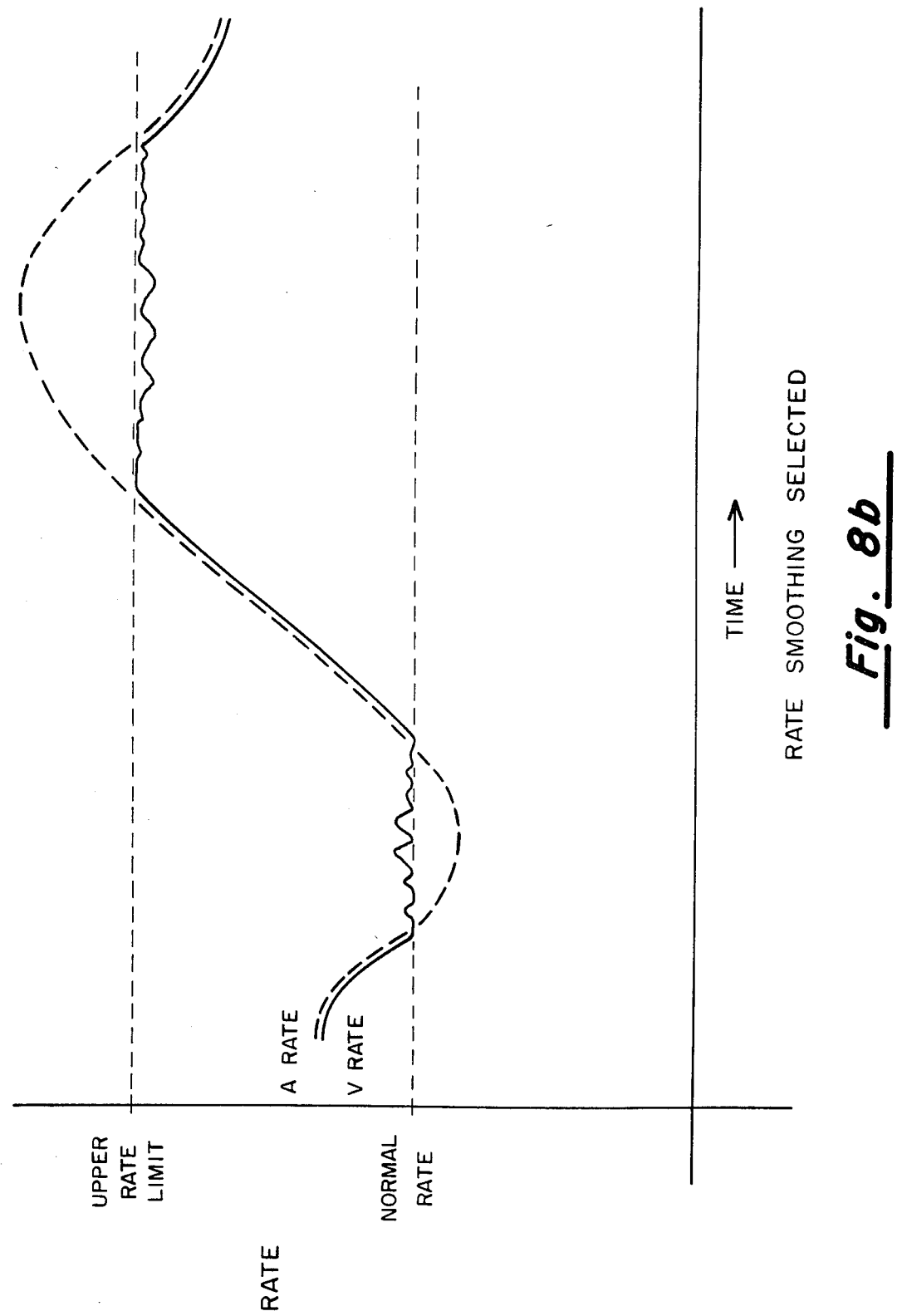

PROGRAMMABLE MULTI-MODE CARDIAC PACEMAKER

BACKGROUND OF THE INVENTION

The present invention relates to cardiac pacemakers and in particular to implantable cardiac pacemakers that are capable of being selectively programmed and/or externally interrogated.

Implantable cardiac pacemakers have been in existence since the later 1950's, although external pacemakers were known even earlier. Since that time great strides have been made in improving upon the leads and the pulse generators that together comprise the pacemaker. In particular, the pulse generator circuitry has evolved from discrete components to semi-custom integrated circuits, which are now fabricated from complimentary metal oxide semi-conductor (CMOS) technology or as with the present invention from integrated injection logic ($I^2L$) technology.

With this evolution, so too have digital techniques been applied to the design of the pulse generator circuitry, as well as techniques for non-invasively programming various of the pacing parameters and modes into the pulse generator. For example, see U.S. Pat. No. 4,304,238 with respect to a programmable parameter pacer. Alternatively, an example of a multi-mode programmable cardiac pacemaker can be found upon reference to U.S. Pat. No. 4,233,985. The pacemaker disclosed therein permits the operator to externally program various of the pacing parameters (i.e. rate, pulse width, pulse amplitude, refractory and sensitivity.) That pacemaker, however, can only be selectively programmed into either the ventricular demand (VVI), R-wave synchronous (VVT) or asynchronous modes of operation.

While the other multi-mode pacemaker accommodates a great many patients that require pacing in one of the other of these modes, there are a great many other patients that require pacing in other modes or for whom the necessary mode of operation may change with time, and which modes or mode changes are not accommodated via devices of the above type. These other desirable pacing modes are atrial demand (AAI), P-wave synchronous (AAT), P-wave synchronous demand (VDD), double demand synchronous (DDD) and A-V sequential (DVI).

The present invention, therefore was developed to permit an operator (1) to selectively program all of the above modes of pacer operation as well as for each of the various associated programmable parameters, (2) to selectively interrogate many of the analog and digital values that are accessible to the pulse generator circuitry and (3) to select a nominal parameter mode, that is dependent upon a number of pre-programmed nominal parameters. Further, the present invention provides the operator to the ability rate smooth and/or gracefully degradate the pacemaker output during conditions of high natural atrial rates.

The present invention, in one pulse generator, thus accommodates all the generally accepted modes of pacemaker operation, while introducing a great many other advantages and improvements. These advantages and improvements over the prior art will, however, become more apparent to those of skill in the art, upon a reading of the following description and upon reference to the appended drawings.

SUMMARY OF THE INVENTION

The present invention comprises an implantable cardiac pacemaker, that may be selectively programmed via a radio frequency link to operate in anyone of the following modes: (1) ventricular demand (VVI), (2) atrial demand (AAI), (3) R-wave synchronous (VVT), (4) P-wave synchronous (AAT), (5) P-wave synchronous demand (VDD), (6) double demand synchronous (DDD) (7) A-V sequential (DVI) and (8) asynchronous. Necessary pacing parameters for each of these modes may also be individually programmed within established ranges or the pacemaker may be operated in a nominal parameter mode (i.e. ventricular demand) using related preprogrammed pacing parameters, should circumstances dictate.

The pulse generator control circuitry is generally configured in the form of input/output (I/O) controller circuitry and pulse generator (PG) or pacing controller circuit and each of which operate independently of one another so as to permit the PG controller to pace the heart in the selected mode, independent of any concurrent communications between an external programmer and the I/O controller. The I/O and PG controller, in turn, communicate with one another via a three bus, paged system employing an arithmetic logic unit, interrupt vector logic circuitry, priority arbitration circuitry, branch control circuitry and associated decoding and timing circuitry.

Also included in the pulse generator control circuitry are additional means for accomodating a "graceful degradation" function, whereby during periods of high natural atrial activity the pulse generator regulates the ventricular pacing rate and causes it to decay from an upper rate limit to the programmed normal rate The pacemaker also contains circuitry for enabling a "rate smoothing" function and which ensures that the ventricular pacing rate, from cycle-to-cycle, changes by only an amount within a pre-programmed percentage of the previous cycle's pacing rate. The pacemaker circuitry further contains circuitry for permitting the programmer to interrogate battery condition or other analog conditions via associated analog-to-digital converters. Still further, the pacemaker contains circuitry for ensuring that the I/O circuitry is essentially "off during periods wherein I/O communications do not occur" so that power is conserved. The architecture of the pacing controller and the multi-function instruction words are also structured to permit the powering down of the instruction memory and pulse width generator during the vast majority of each cardiac cycle, thereby further reducing power consumption.

BRIEF DESCRIPTION OF THE DRAWINGS

FIGS. 1, 1a, and 1b show a system block diagram of the major elements of the present invention.

FIG. 2 shows the relative relationship and duration of the sync pulses and data window.

FIGS. 4, 4a, 4b, 4c and 4d, show a detailed block diagram of the pulse generator control circuitry.

FIGS. 5.1 through 5.22, shows the detailed schematic diagrams of the I/O controller circuitry.

FIGS. 6.1 through 6.22 shows the detailed schematic diagrams of the PG controller circuitry.

FIGS. 8a and 8b, show exemplary waveforms demonstrating the before and after effects of rate smoothing.

FIG. 9 shows the various fields of the 30 bit instruction words stored in ROM.

DESCRIPTION OF THE PREFERRED EMBODIMENT

Figure 1B:
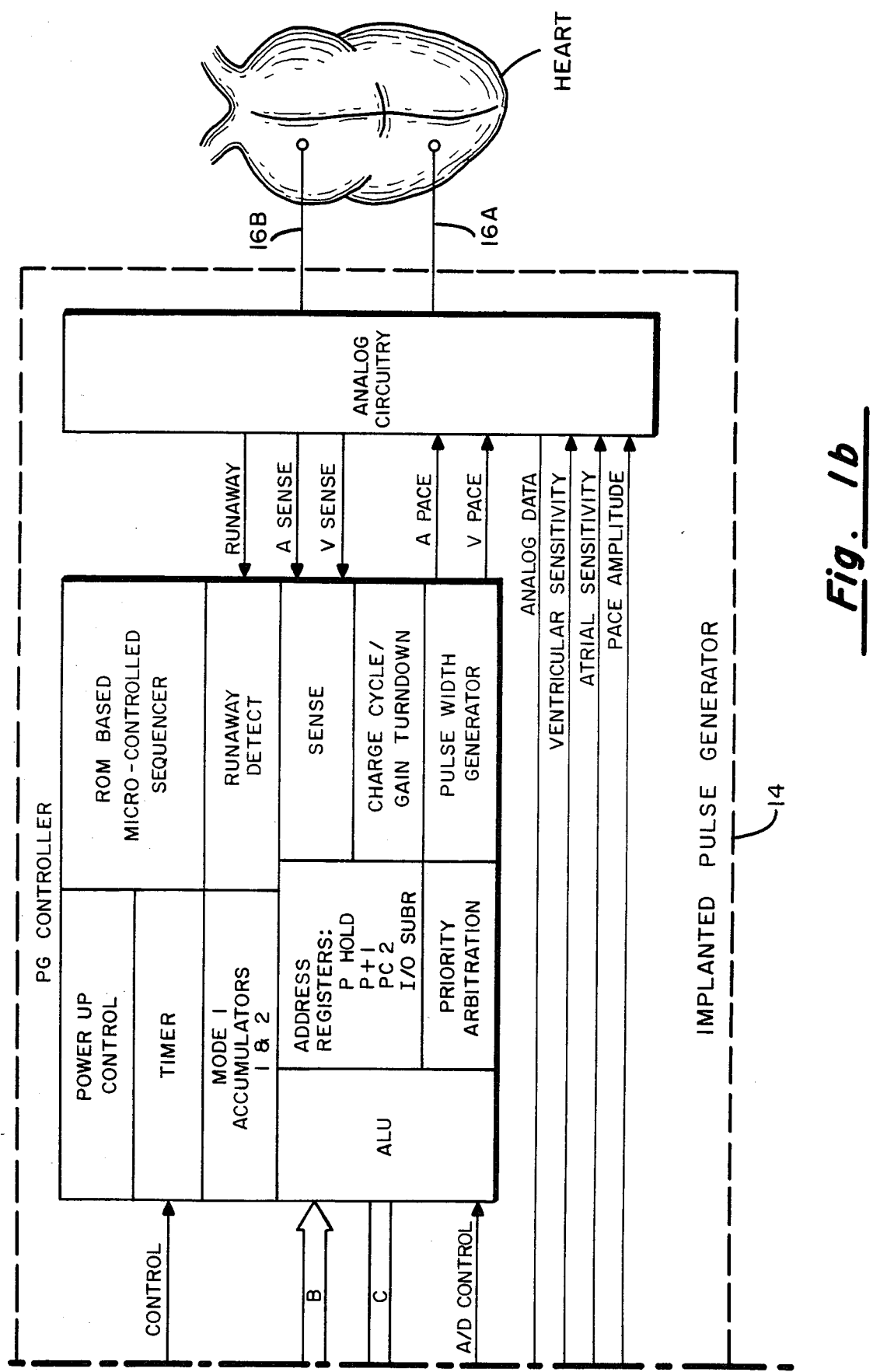

Referring to FIG. 1, a system diagram is shown of the present pacemaker system and the various elements thereof. Specifically, these elements are the external programmer 10, the RF data link 12, the pulse generator 14 and the pacing leads 16A and 16B. While only the control circuitry of the pulse generator 14 will be described in any great detail hereinafter, brief mention will now be made to each of the individual elements of the system. In particular, attention is first directed to the external programmer 10 and which is essentially comprised of apparatus for transmitting pulses of radio frequency at 100 kilohertz. These pulses and the period between pulses have been respectively defined as sync pulses and data pulses.

Referring to FIG. 2, a typical sync pulse and the inter-period time is shown relative to a defined "data window". The sync pulses are transmitted once each millisecond at a 1 kilohertz rate and have a duration of approximately 0.05 milliseconds to 0.2 milliseconds. The period between the sync pulses is sub-divided into the data window and which starts approximately 400 microseconds after the leading edge of a sync pulse and continues for 300 microseconds, with an approximate 300 microsecond gap before the next sync pulse. It is the I/O controller's detection of the existence or non-existence of a pulse during this data window, that determines whether or not a binary "1" or "0" is transmitted/detected. A binary "1" corresponds to the presence of a pulse and binary "0" to the absence of a pulse.

The pulsed transmissions from the external programmer 10, as well as from the pulse generator 14 are, upon receipt formatted into the proper sequence and are appropriately interpretted by the receiver, depending upon the transmission mode of the programmer (i.e. idle, read or write). The specific order of transmission for the various words (i.e. idle, flag, command, response, data or CRC) used during the various transmission modes of the present apparatus can be seen more clearly upon reference to FIG. 3 and which will be described in greater detail hereinafter. It should be recognized too that because of the two-way communications and the symmetry of the various transmissions, the encoding/decoding circuitry within the external programmer 10 and the pulse generator 14 are essentially identical, but which circuitry too will be described in greater detail hereinafter.

Returning next to the of the external programmer 10, it is to be noted that it typically contains a keyboard (not shown) for permitting the operator to enter desired communications; a display (not shown) for visually displaying the communications; and various dedicated switches (not shown) for controlling certain pulse generator actions such as restart, identification of pacemaker type, and battery check, among various other automatic functions that the operator may desire. For more information with respect to the present programmer 10, attention is directed to available product literature descriptive of the present Assignee's Mode 2000 Programmer. The model 2000 programmer is of the same general type as the present programmer 10, albeit it employs an electro-magnetic field and does not contain as much functionality as the present programmer 10.

As mentioned, the external programmer 10 and pulse generator 14 communicate with one another via the RF data link 12 and the I/O controller circuitry. The RF data link 12 is established upon placing an external antenna (not shown) over the skin of a patient within whom the pulse generator 14 is implanted and in proximity thereto. The RF signals are detected and the link 12 is completed by a subjacent RF antenna (not shown) that is contained within or coupled to the pulse generator 14. In the present apparatus, the circuitry is configured to operate in parallel, with I/O communications between the programmer 10 and pulse generator 14 occurring, independent of on-going pacing activities. Once the pacemaker is initiated, pacing pulses are produced without interruption and as required by the heart's activity and the mode in process and are transmitted to the heart via the ventricular and atrial leads 16A and 16B. I/O communications are thus interleaved with the pacing activities on a non-interference basis so as to permit the changing of the pacing mode or parameters, as necessary, without affecting the delivery of pacing pulses.

Completing the system and intermediate the heart and digital-to-analog conversion circuitry are an appropriate ventricular lead 16A and atrial lead 16B, which are in contact with the respective chambers of the heart so that appropriate pacing pulses can be applied thereto and naturally occuring R and P waves can be sensed therein. The specific types of leads that may be employed are numerous, but generally an endocardial lead of the type manufactured by the present assignee is preferred. These leads are placed within the appropriate heart chamber via the right and/or left external jugular veins or the right and/or left cephalic veins.

Prior to next describing in detail the operation and circuitry of the pulse generator 14, it is to be noted that one important feature of the present pacemaker system is its ability to be programmed into any one of the plurality of generally accepted modes of operation, with only the one pulse generator. As mentioned, any one of the following modes may be selectively programmed: ventricular demand (VVI), atrial demand (AAI), R-wave synchronous (VVT), P-wave synchronous (AAT), P-wave synchronous demand (VDD), double demand synchronous (DDD) or A-V sequential (DV) along with single or dual chamber asynchronous operation. The specific mode selected is only dependent upon the requirements of the patient; and thus the present pulse generator 14 provides a great step forward in patient care and towards standardization, since the mode and not the pacemaker can now be changed to accommodate changes in the patient's needs and only one pulse generator need now be inventoried. Further, the operator need now only be familiar the operation of the one pulse generator and not a number of special mode pacers.

Another important feature is that the operating parameters of the present pulse generator 14 are also selectively programmable within relatively broad ranges so that the programmer can tailor the operation of the pulse generator to the selected mode and to the individual. The programmable parameters provided are rate (30-150 bpm), sensed refractory (140-700 milliseconds), P-R interval (0-300 milliseconds), upper rate limit (rate-150 bpm), hysteresis rate (30-150 bpm), ventricular pulse width (0-1.9 milliseconds), atrial pulse width (0-1.9 milliseconds,) R-wave sensitivity (0.25-15.75 millivolts) and P-wave sensitivity (0.25-15.75 millivolts).

Still another important feature is that included in the memory of the present apparatus is a set of preprogrammed, operator accessible nominal parameters that which can be automatically reverted to upon the pulse generator 14's detecting various abnormal conditions, thereby always ensuring the operation of the pulse generator 14 in at least the ventricular demand mode. The specific nominal parameter values are set forth in Table 1 below. It is to be recognized though that other parameters for various of the other modes may also be preprogrammed and which too may either be automatically or selectively accessed in whole or in part, depending upon design choice.

TABLE 1
PREPROGRAMMED NOMINAL PARAMETERS MODE (VVI)

| Parameter | Value |
| --- | --- |
| RATE | 72 bpm |
| REFRACTORY | 320 msec |
| P-R INTERVAL | N/A |
| RATE LIMIT | N/A |
| HYSTERESIS RATE* | 72 bpm |
| ATRIAL REFRACTORY | N/A |
| VENT. PULSE WIDTH | 1.0 msec |
| VENT. SENSITIVITY | 1.5 mV |
| ATRIAL PULSE WIDTH | N/A |
| ATRIAL SENSITIVITY | N/A |
| RATE SMOOTHING | N/A |
| DEGRADATION SLOPE | N/A |
| DEGRADATION DELAY | N/A |

(*NOTE: WHEN ACCESSING THE NOMINAL PARAMETERS, HYSTERESIS IS EFFECTIVELY DISABLED, SINCE IT IS THE SAME AS THE RATE.)

Referring now to the pulse generator 14, upon leaving the factory, the pulse generator 14 is operational and is programmed into a low power consuming mode in order to extend the shelf life of the unit and to provide the operator with a known starting point. For instance, this starting mode may be the nominal parameter mode. The specific mode is not critical though as the operator or implanting physician will typically re-program the unit to a desired mode and set of pacing parameters, prior to implantation.

Figure 3A:
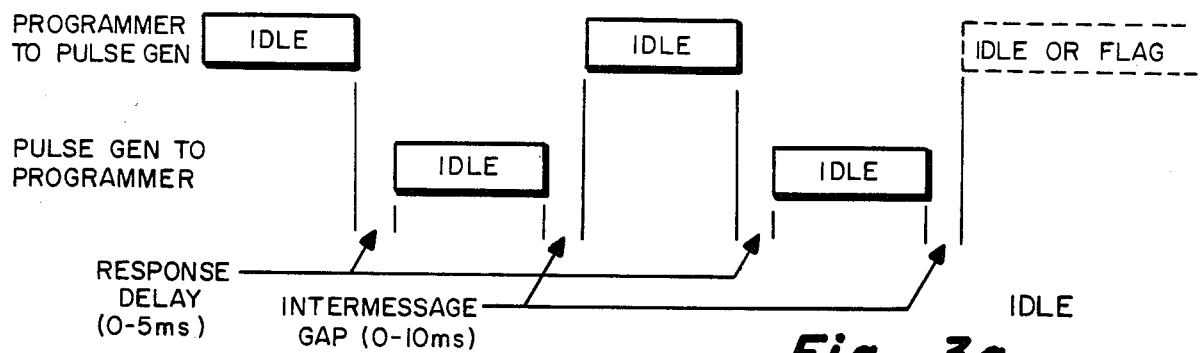
FIGS. 3a, 3b, 3c, and 3d, show the typical word communication sequences the respective IDLE, READ, WRITE and ABNORMAL RESPONSE.

Before or upon implantation, the pulse generator 14 is programmed by bringing it and external programmer 10 into proximity with one another so that the RF signals from one another can be detected. Referring to FIG. 3a, communications are initiated via the programmer 10, which first transmits an eight bit idle word (i.e. 10000001) to the pulse generator 14. The programmer 10 then waits for the pulse generator 14 to respond with its own idle word. If an idle word response isn't detected, the programmer 10 re-transmits a new idle word and again waits. This transmission and wait for response of idle words thereafter continues between the programmer 10 and pulse generator 14 until synchronization is established and at which time the programmer 10 transmits a flag word (i.e. 01111110) and in response to which the pulse generator 14 readies itself for receipt of a command word.

Figure 3B:
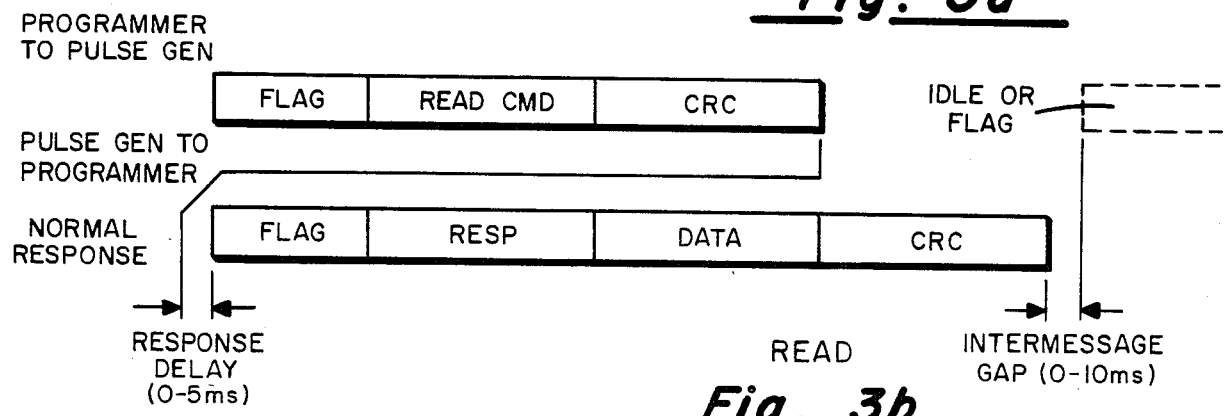
Figure 3C:
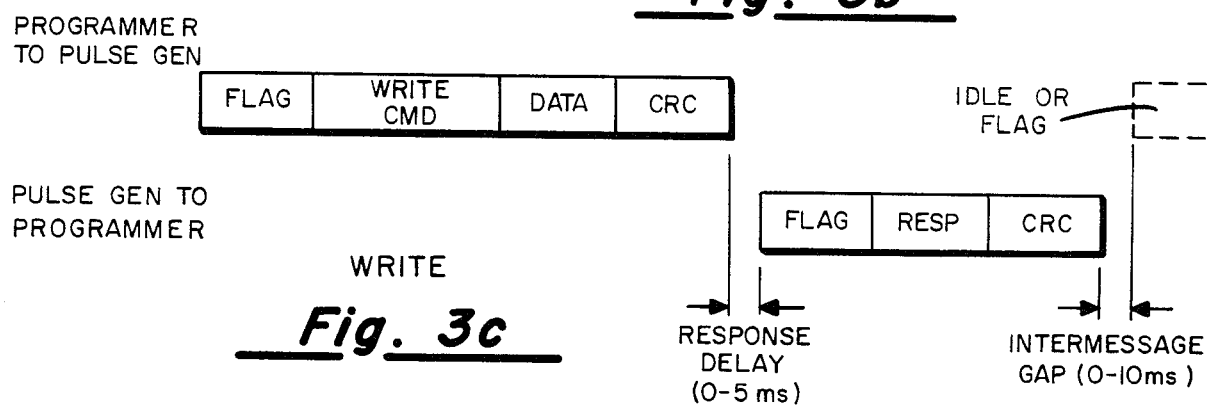

Immediately following the establishment of synchronization and referring to FIGS. 3b to 3c the programmer 10 typically transmits a command sequence that specifies the pulse generator type, the command type (see Table 2) and a sub-system address. For instance, the programmer 10 may transmit a WRITE command, followed by a cyclic redundancy check (CRC) word which generally accompanies every transmission and confirms the accuracy thereof. The pulse generator 14 then responds with another flag word, a response word that contains its own error information, a pulse generator status word (e.g. buffer ready) and the internal address of the responding sub-system. On the other hand, the pulse generator 14 may transmit a READ command and to which the pulse generator 14 would respond with the requested data along with another CRC word. Alternatively, if an error was detected by the pulse generator 14, it would respond with a flag word and an appropriate response indicating the type of error and its own CRC word.

Thus, communications between the programmer 10 and the pulse generator 14 occur in the three basic communication modes of IDLE, READ or WRITE and by which the operator can program the desired mode of operation as well as the desired parameters and magnitudes thereof (within the ranges allowed). It should also be noted that this communications capability permits the operator to interrogate many of the parameters within the pulse generator 14, since the programmer 10 can read and write most of the registers that are coupled to the buses within the pulse generator 14. Consequently, the programmer can also interrogate various of the analog conditions that are available to the A/D converter subsystem (e.g. battery voltage and current and from which a relative value indicative of the remaining life of the battery can be determined).

Returning again to the various programmable single and dual chamber modes and parameters of the present apparatus, two new functions are also provided. In particular and in recognition of the high atrial rates that often occur during a patient's normal activities as well as of the need for an upper rate limit beyond which the ventricle will not be paced, the additional functions of "rate smoothing" and "graceful degradation" have been incorporated into the circuitry of pulse generator 14 and either or both of which may also be selectively programmed by the operator. Specifically, rate smoothing can be selected during either of the dual chamber P-wave synchronous demand (VDD) or double demand synchronous (DDD) modes. Rate smoothing, upon selection, operates to ensure that the pacing rate from pacing interval-to-pacing interval does not change by more than a selected percentage of the previous interval. Thus, the pulse generator 14 is able to provide a smoother, less erratic, pacing rhythm during the above-mentioned dual chamber modes.

Graceful degradation, on the other hand, offers the ability to gracefully reduce the ventricular pacing rate from the upper rate limit down to the programmed rate, during those times when the atrial rate is at or exceeds the upper rate limit. Normal physiologic conditions, such as during exercise when atrial rate naturally increases, can also be accommodated via the programming of a delay period or "onset internal" and before the expiration of which the graceful degradation function will not become operative. Thus, assuming that graceful degradation has been selected and that the atrial rate exceeds the upper rate limit, the pulse generator 14 will pace the ventricle at or near the upper limit rate. The upper rate limit (i.e. 120-150 bpm) may, however, be excessive for certain individuals or at least not to be tolerated for long periods of time, therefore, by programming an onset interval, the operator is able to control the amount of time prior to the graceful degradation circuitry's beginning to reduce the pacing rate down to the programmed rate. In order to accomodate the various possible high atrial rate situations that might arise, the present circuitry permits the operator to selectively program the onset interval from 1 to 2048 beats in increments of eight beats and to gracefully degrade the ventricular rate in an incremental fashion along any one of 256 programmable degradation slopes, wherein each slope is comprised of a plurality of equal incremental changes in rate.

In order to now better understand the specifics of the present control circuitry and its operation during the various modes, attention is directed to FIGS. 4 and 4a to 4d wherein a detailed block diagram is shown of the I/O controller circuitry and the PG controller circuitry. Attention will also be directed from time to time to FIGS 5.1 through 5.22 and wherein more detailed schematic diagrams are shown for the various circuitry that comprises the elements of the block diagram of FIGS. 4 and 4a to 4d. For the moment, though, particular attention is directed to the I/O controller circuitry.

As soon as the battery power source is placed in the pulse generator 14, the PG controller circuitry is powered up and becomes fully operational, but the I/O controller circuitry is only partially powered up. That is, the I/O controller is able to detect RF transmissions from the programmer 10, but the circuitry is not fully powered so as to be able to communicate with the programmer 10. Only after sensing successive sync pulses for three, four millisecond periods, at input terminal 20, does the pulse generator 14 respond and cause a flip-flop in the "power on" logic circuitry 22 to be set and which, in turn, causes the remainder of the I/O controller circuitry to be powered up, see FIG. 5.1(b).

At the same time, the master clear (MCLR) line 26 is disabled and the telemetry encode/decode circuitry 24, see FIG. 5.1a, begins to monitor its input terminal 20 to detect and decode the data contained within the sync pulses and begin to look for an idle word so as to establish sychronization between the external programmer 10 and the pulse generator 14. In particular, the telemetry encode/decode circuitry 24 looks for the presence or absence of a pulse within the 300 microsecond data window of each sync pulse, and which conditions are respectively decoded into binary "1's" and "0's". The thus decoded data is then transmitted in a serial fashion via the serial port input bus 28 to the command decode (CMD DECODE) logic circuitry 30, see FIG. 5.4a, where it is loaded into an eight bit register and decoded via associated logic circuitry to determine whether or not each successive eight bits correspond to an idle word. As the command decode circuitry 30 attempts to identify eight bit idle word (i.e. 10000001), the identification process may be hindered by the pulse generator 14's not initially being in phase with the sync pulses. Thus, if the programmer 10 fails to get a response to its first idle word, it must retransmit a new idle word and again wait and/or repeat the process until an idle word response is detected.

Once an idle word is detected, the command decode circuitry 30 transmits an IDLE detect signal to the sequence control logic 32, see FIS. 5.2, 5.3, 5.4b, and 5.8. The sequence control logic 32 responds and causes the telemetry encode/decode circuitry 24 to open its output line 34 so that the response decode circuitry 36, see FIG. 5.5, can respond back to the external programmer 10 with an idle word of its own word. The reception of an idle word from the pulse generator 14 by the programmer 10, confirms that synchronization has been established, and the programmer 10 can thereafter either transmit a command sequence or another idle word. However, if a command is not entered, another idle word is transmitted and the pulse generator 14 responds with another idle word. Thus, a "ping-pong" effect occurs (i.e. idle-in, idle out) and which continues until a command sequence (i.e. READ or WRITE) is transmitted and the command decode cicuitry 30 detects and confirms it. This idling process can be seen upon reference to FIG. 3a. It is to be noted too that the inter-message gap between consecutive idle words must be less than 10 milliseconds in order to prevent the powering off of the I/O controller.

Assuming that the operator desires to transmit a command to the pulse generator 14, the operator must enter either a READ or a WRITE command. In either event though, a flag word (i.e. 01111110) proceeds the READ or WRITE command and causes the command decode logic circuitry 30 to produce a control signal that, in turn, causes the sequence control logic circuitry 32 to properly control the remainder of the I/O sequence.

In that regard, attention is directed to Table 2 below and wherein the various fields of a typical sixteen bit command word are shown relative to the various bit positions of the command word. Depending upon the command word, the binary value at each bit position, is detected and decoded via the command decode logic circuitry 30 and responsively coupled to associated control circuitry, where they establish an appropriate READ, WRITE or RESTART instruction sequence, as well as establish the function the B/C ADDRESS, File/A ADDRESS and PG TYPE fields. The specific functional assignments of each of these latter fields are set forth in Table 3, below. It is also to be noted that Table 2 shows the typical field assignments for the pulse generator 14's response words.

TABLE 2

| FIELD FORMATS FOR COMMAND AND RESPONSE WORDS | | | | |
|---|---|---|---|---|
| COMMAND: | | | | |
| 15 14 13 12 | 11 10 9 8 | 7 6 5 | 4 3 2 1 | 0 |
| B/C ADRS | FILE/A ADRS | CMD | PG TYPE | WORD TYPE |
| RESPONSE: | | | | |
| 15 14 13 12 | 11 10 9 8 | 7 6 5 | 4 3 2 1 | 0 |
| B/C ADRS | FILE/A ADRS | ERR | PG STATUS | WORD TYPE |

TABLE 3

FIELD ASSIGNMENTS

TABLE 3-continued

B/C ADRS: The B/C address field selects a source pair of registers from the B-Bus during a READ and a destination pair of registers for the C-Bus during a WRITE.
NOTE: During READ operations, the A-BUS and B-BUS register outputs are added together when driving the C-BUS. The zero constant operand is also always selected on the unrequested BUS during a READ and on the A-BUS during a WRITE. A file request also automatically forces the zero constant onto the A-BUS.

B BUS (READ)

| FIELD BITS 15 14 13 12 | REGISTER 15 14 13 12 11 10 9 8 | ASSIGNMENT 7 6 5 4 3 2 1 0 |
|---|---|---|
| 0 0 0 0 | CONSTANT 0, | CONSTANT 0 |
| 0 0 0 1 | PACE AMPLITUDE, | PR-INTERVAL |
| 0 0 1 0 | DATA ACQUISITION, | DATA ACQUISITION |
| 0 0 1 1 | ATRIAL SENSITIVITY, | ATRIAL WIDTH |
| 0 1 0 0 | INTERRUPT VECTOR, | SERIAL PORT ADRS |
| 0 1 0 1 | MODEL NUMBER, | MODE 2 REG. |
| 0 1 1 0 | MODE WIDTH, | VENTRICULAR SENSITIVITY |
| 0 1 1 1 | ACCUMULATOR 3, | ACCUMULATOR 4 |
| 1 0 0 0 | ATRIAL BLANKING INTERVAL, | ABSOLUTE REFRACTORY |
| 1 0 0 1 | COMPLEMENT TIMER, | CONSTANT 0 |
| 1 0 1 0 | G.D. ONSET, | G.D. INTERVAL |
| 1 0 1 1 | ACCUMULATOR 5, | CONSTANT 0 |
| 1 1 0 0 | CONSTANT 0, | ACCUM 5 SHIFTED |
| 1 1 0 1 | PERIOD 2 (UPPER RATE LIMIT), | PERIOD 1 (ESCAPE) |
| 1 1 1 0 | CONSTANT 0, | CONSTANT 0 |
| 1 1 1 1 | SERIAL PORT 1, | SERIAL PORT 0 |

C BUS (WRITE)

| FIELD BITS 15 14 13 12 | REGISTER 15 14 13 12 11 10 9 8 | ASSIGNMENT 7 6 5 4 3 2 1 0 |
|---|---|---|
| 0 0 0 0 | DATA ACQUISITION 1, | DATA ACQUISITION 0 |
| 0 0 0 1 | MODE PULSE WIDTH CNTR, | ATRIAL PULSE WIDTH CNTR |
| 0 0 1 0 | ACCUMULATOR 1, | ACCUMULATOR 2 |
| 0 0 1 1 | ACCUMULATOR 3, | PAGE REGISTER 0 |
| 0 1 0 0 | AUXILARY COUNTER, | PROGRAM COUNTER 2 |
| 0 1 0 1 | G.D. INTERVAL, | G.D. ONSET |
| 0 1 1 0 | ACCUMULATOR 5, | MODEL NUMBER |
| 0 1 1 1 | NO OPERATION, | ACCUMULATOR 4 |
| 1 0 0 0 | PERIOD 2 (UPPER RATE LIMIT), | PERIOD 1 (ESCAPE) |
| 1 0 0 1 | ATRIAL BLANKING INTERVAL, | ABSOLUTE REFRACTORY |
| 1 0 1 0 | MODE 1 REGISTER, | MODE 2 REGISTER |
| 1 0 1 1 | NO OPERATION, | PAGE REGISTER 1 |
| 1 1 0 0 | MODE WIDTH, | VENTRICULAR SENSITIVITY |
| 1 1 0 1 | ATRIAL WIDTH, | ATRIAL SENSITIVITY |
| 1 1 1 0 | PACE AMPLITUDE, | PR-INTERVAL |
| 1 1 1 1 | SERIAL PORT 1, | SERIAL PORT 0 |

FILE/A ADRS: The file/A address field selects an A-BUS register pair during a read command and an internal subsystem file, if specified, at other times.

| FIELD BITS 11 10 9 8 | CMD | ASSIGNMENT |
|---|---|---|
| 1 X X X | READ | A-Bus registers XXX0, XXX1 |
| O X X X | READ | CONSTANT 0 |
| 1 X X X | WRITE | Not defined |
| O X X X | WRITE | Not defined |

A-BUS (READ)

| FIELD BITS 11 10 9 8 | REGISTER 15 14 13 12 11 10 9 8 | ASSIGNMENT 7 6 5 4 3 2 1 0 |
|---|---|---|
|  | CONSTANT 0, | CONSTANT 0 |
| 1 0 0 0 | CONSTANT 0, | CONSTANT 0 |
| 1 0 0 1 | PROGRAM CONSTANT, | CONSTANT 0 |
| 1 0 1 0 | ACCUMULATOR 2, | MAR |
| 1 0 1 1 | TIMER, | ACCUMULATOR 1 |
| 1 1 0 0 | CONSTANT 0, | MODE 1 REG. |
| 1 1 0 1 | CONSTANT 0, | CONSTANT 0 |
| 1 1 1 0 | CONSTANT 0, | CONSTANT 0 |

CMD: The command field specifies the type of data transfer to follow. WRITE commands transfer data to the PG controller from the Programmer. Read commands transfer data from the PG controller to the Programmer.

| FIELD BITS 7 6 5 | ASSIGNMENT |
|---|---|
| O X X | Programmer read (interrogate) |
| 1 X X | Programmer write |
| O 0 0 | Read buffer |
| 0 0 1 | Read request |
| 0 1 0 | Read interrupt |
| 0 1 1 | Spare |
| 1 0 0 | Write buffer |
| 1 0 1 | Write request |

TABLE 3-continued

| | | | |
|---|---|---|---|
| 1 | 1 | 0 | Write interrupt |
| 1 | 1 | 1 | Restart |

PG TYPE     The pulse generator type field defines a unique code for each pulse generator type. A pulse generator will accept commands from the Programmer only if a match exists.

| FIELD BITS | | | | |
|---|---|---|---|---|
| 4 | 3 | 2 | 1 | ASSIGNMENT |
| 0 | 0 | 0 | 0 | Spare |
| 0 | 0 | 0 | 1 | Demand IV |
| 0 | 0 | 1 | 0 | Spare |
| 0 | 0 | 1 | 1 | Spare |
| 0 | 1 | 0 | 0 | Spare |
| 0 | 1 | 0 | 1 | Spare |
| 0 | 1 | 1 | 0 | Spare |
| 0 | 1 | 1 | 1 | Spare |
| 1 | 0 | 0 | 0 | Spare |
| 1 | 0 | 0 | 1 | Spare |
| 1 | 0 | 1 | 0 | Spare |
| 1 | 0 | 1 | 1 | Spare |
| 1 | 1 | 0 | 0 | Spare |
| 1 | 1 | 0 | 1 | Spare |
| 1 | 1 | 1 | 0 | Spare |
| 1 | 1 | 1 | 1 | Spare |

ERR:     The error field of a response word indicates to the programmer any errors in the last message received by the pulse generator.

| FIELD BITS | | | |
|---|---|---|---|
| 7 | 6 | 5 | ASSIGNMENT |
| 0 | 0 | 0 | NO ERROR |
| 0 | 0 | 1 | P.G. BUSY |
| 0 | 1 | 0 | CRC ERROR |
| 1 | 0 | 0 | ILLEGAL COMMAND |

WORD TYPE     The word type field specifies whether the word is a command word or a response word.

| FIELD BITS | ASSIGNMENT |
|---|---|
| 0 | ASSIGNMENT |
| 1 | COMMAND |
| 0 | RESPONSE |

PG STATUS:     The pulse generator status field of a response word indicates internal status conditions. The status indicated in response to any abnormal condition (i.e. illegal command, CRC error, or busy) is the PG type code.

| FIELD BITS | | | | |
|---|---|---|---|---|
| 4 | 3 | 2 | 1 | ASSIGNMENT |
| 0 | 0 | 0 | 1 | For all abnormal responses |
| 1 | X | X | X | Data aquisition port busy |
| 0 | X | X | X | Data aquisition port available |

Figure 3D:
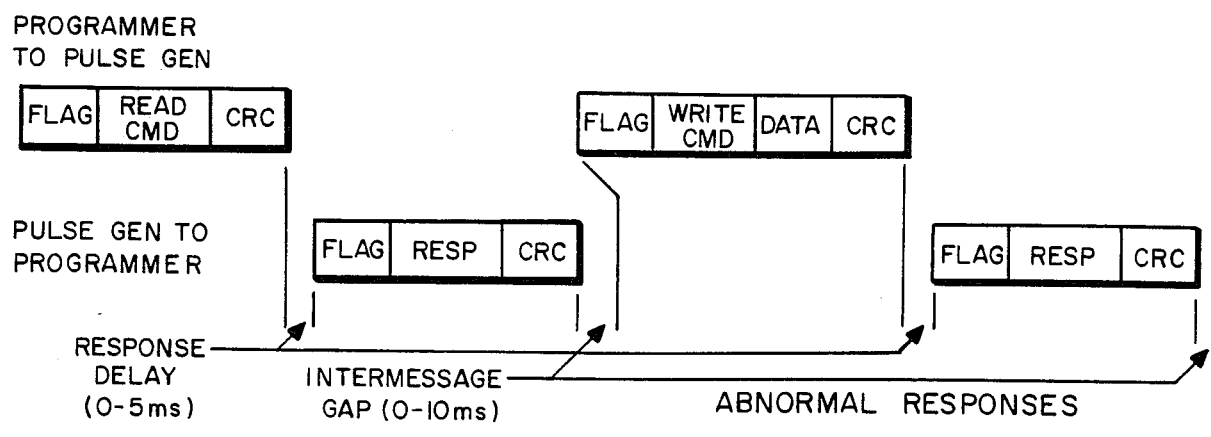
Figure 4A:
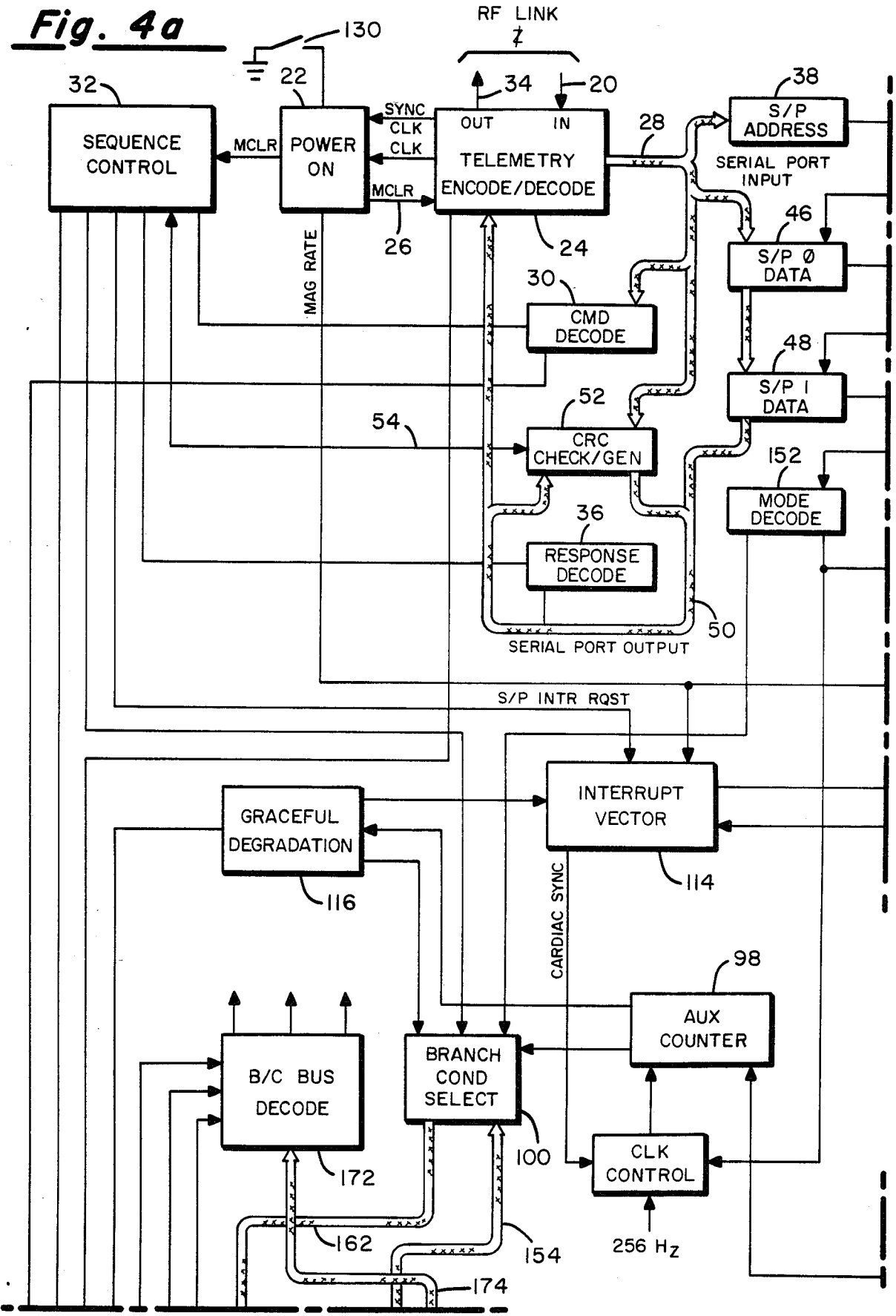
Figure 4B:
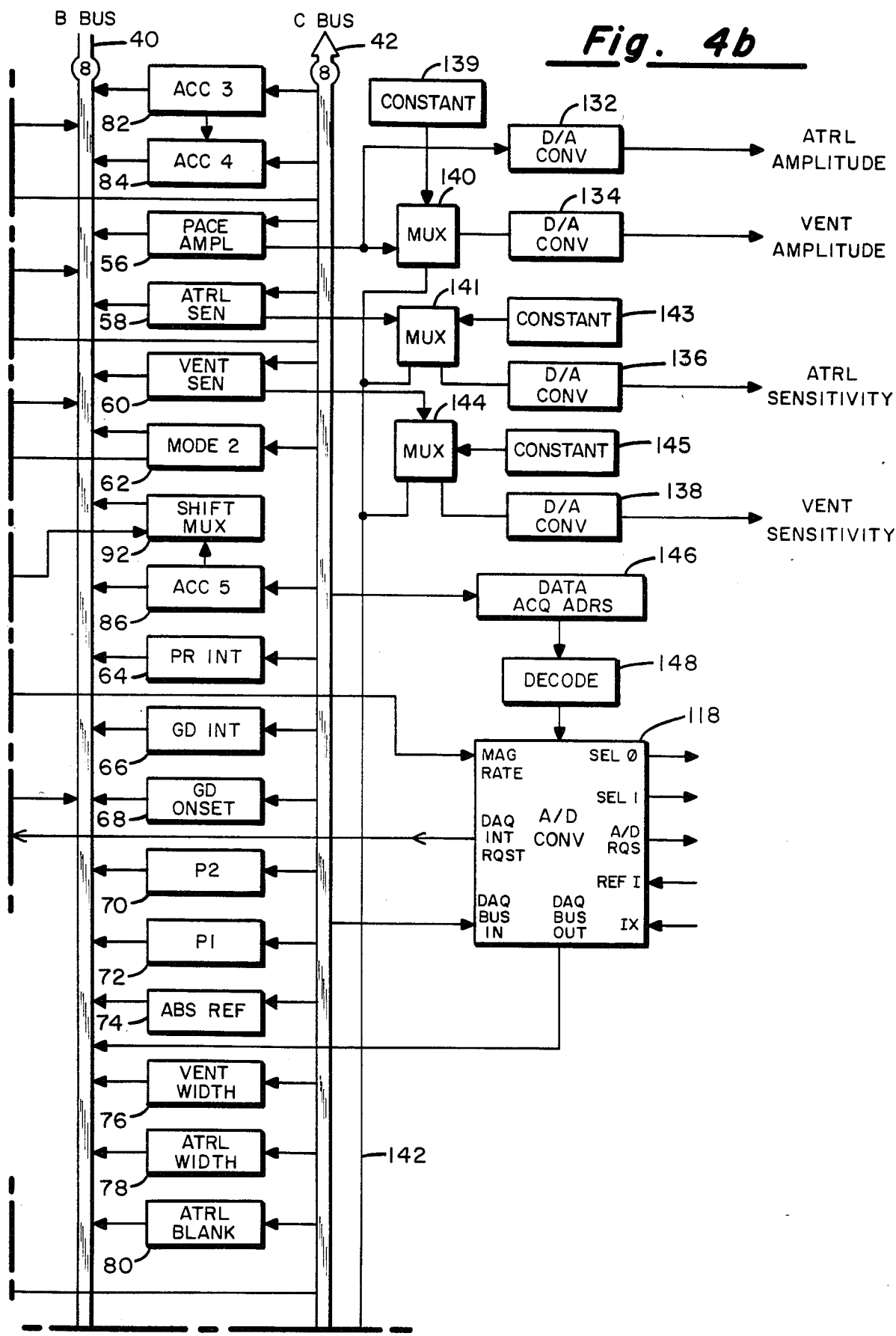
Figure 4C:
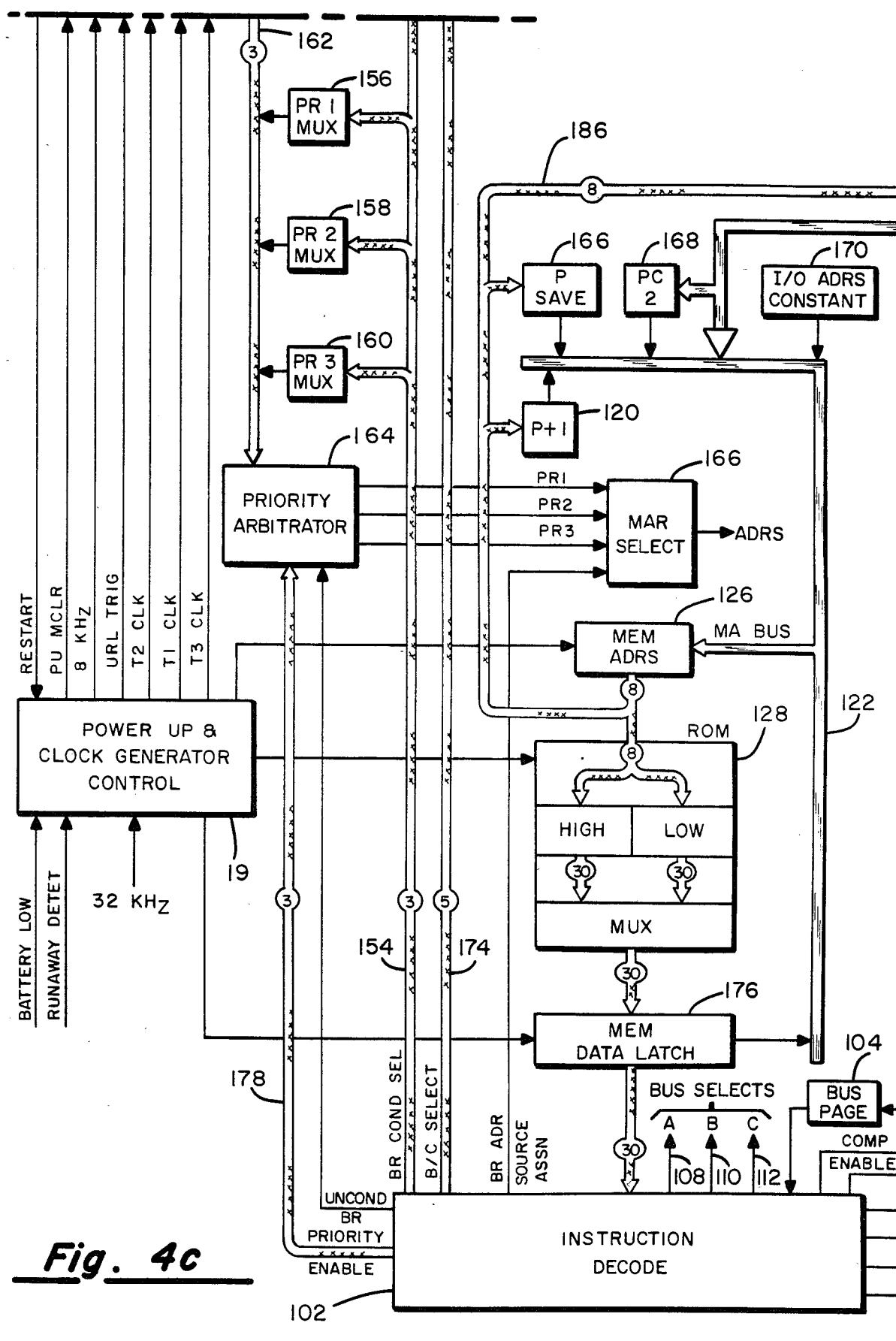
Figure 4D:
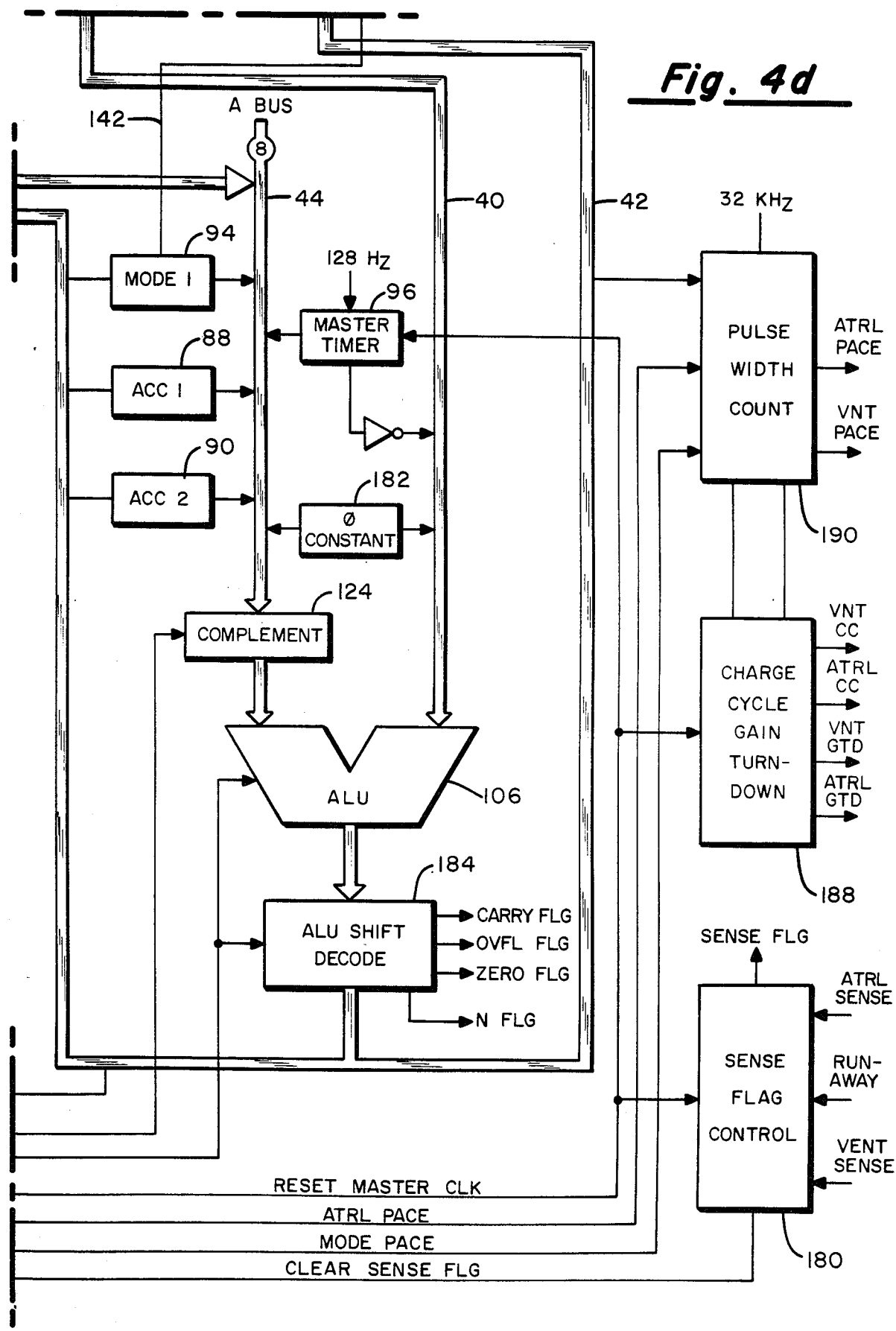

Prior to referring to the individual fields of the command and response words, it is to be recalled that the programmer 10 and pulse generator 14, each transmit a CRC word, see FIGS. 3b, 3c and 3d, with each transmission. The CRC word is an error control word that is used in all modes of transmission, except "IDLE", to confirm the accuracy of the transmission. It is comprised of a 16 bit remainder from a long division operation that is performed by the CRC check/generator circuitry 48, see FIG. 5.6, and which uses all the words in a transmission, except the flag word, as a binary dividend and the CRC generator polynomial (i.e. $X^{16}+X^{12}+X^5+1$) 1 as a divisor. Thus, for each transmission, the transmitter, whoever it is, includes its CRC word in its transmission and the receiver performs a similar division, upon receipt, using all the words of the transmission (again excluding the flag word, but including the received CRC word) to calculate another CRC word. If a non-zero result is obtained from the receiver's division operation, a transmission error is indicated. If, however, the result of the division is zero, then no error is deemed to have occured during the transmission. It is to be noted too that this division process is essentially performed by logic manipulations within the I/O controller circuitry and thus does not require arithmetic processing time.

In particular and with respect to the pulse generator 14, as a command sequence is received, the CRC check/gen circuitry 52 (or the equivalent circuitry in the programer 10) performs the above logic manipulations. If upon checking the received sequence, it is determined that an error occurred during transmission of the command word, the CRC check/gen circuitry 52 advises the sequence control logic circuitry 32 of the non-zero condition via an appropriate control signal on conductor 54. The sequence control logic circuitry 32, then, causes the response decoder circuitry 36, see FIG. 5.5, to transmit a CRC error response (i.e. 010) to the programmer 10 via the response decoder circuitry 36 and the serial port output bus 50 and which requires the operator to re-transmit. The CRC check generator circuitry 52 thus ensures with a high degree of probability that the pulse generator control circuitry will not respond to transmissions containing errors, other than to transmit an error message to the programmer.

Referring now to Table 2, it is to be noted that each command or response word contains an 8 bit address field, where 4 bits specify an address on the B or C BUSES (i.e. B/C ADRS) 40 and 42 and 4 bits specify an address in File or on the A Bus 44 (i.e. File A/ADRS). The specific buses selected via the address field data will, however, depend upon whether a READ or WRITE command is to be performed and which will be determined when the three CMD bits are decoded by the command decode circuitry 30.

In any event, as the 8 bits of address data are received from the telemetry encode/decode circuitry 24 they are transmitted via the serial port input bus 28 to the serial port address (S/P ADDRESS) register 38, see FIG. 5.7, and from which the address data is properly coupled via the B BUS 40 to the bus page or "jam" register 104, see FIG. 6.15 in the instruction decode circuitry 102, where it is used to select the proper source and destination registers. In particular, the contents of the bus page register 104 are used to jam or force the A, B, and C BUS SELECT signals from the instruction decode circuitry 102, see FIG. 6.14, onto conductors 108, 110 and 112 in an appropriate fashion, depending upon whether a READ or WRITE operation is to be performed. From Table 2, it is to be noted that, during a READ, the first four bits define a pair of source registers that are coupled to the B BUS 40 and, during a WRITE, a pair of destination registers coupled to the C BUS 42. Also, the fourth bit File/A ADRS field denotes either (1) a subsystem file that may be selected and coupled to the B BUS 42 to facilitate the operation of the system, or (2) a pair of source registers, during a READ command that are to be coupled to the A BUS 44. Thus, the B/C ADRS and File/A ADRS address fields are included in all commands to define pairs of registers from which data is to be read or into which data is to be written and in all responses to confirm the addresses read or written.

If a Write command is received, the sixteen bits of data that follow the command word are loaded into the serial-to-parallel S/P 0 and S/P 1 data registers 46 and 48, see FIG. 5.7. Upon decoding the command word, this data is then written into the destination registers defined by the four bit B/C ADRS address field. During a READ command, however, the S/P 0 and S/P 1 data register 46 and 48 do not receive any data, until after the data has been read from the source registers defined by the B/C ADRS address field. Once the data is read from the source registers and stored in the S/P 0 and S/P 1 registers 46 and 48, it is then coupled to the telemetry encode/decode circuitry 24 via the serial port bus 50 where it is converted and transmitted after the response word.

From Table 2, it is also to be noted that each command word contains a pulse generator type field (i.e. PG TYPE) as well as a one bit field in the least significant bit position that specifies the word type (i.e. COMMAND or RESPONSE). At present, only one pulse generator type has been assigned (i.e. Demand IV), while the remainder of the possible binary permutations have been relegated to spare positions. However, upon future expansion of the concepts of the present invention into other types of pulse generators, these generators will be assigned other PG TYPE numbers. Thus, the programmer 10 is able to detect and confirm which type of pulse generator it is communicating with and thereby ensure that the proper protocol is followed during communications.

Also, it is to be noted that each RESPONSE word contains a 3 bit error field (i.e. ERR) and a 4 bit pulse generator status field (i.e. PG STATUS). At present, the error field only provides for the conditions of PG busy, CRC error and illegal command. PG busy indicates that the pulse generator cannot perform the command at the present time. CRC error has already been mentioned and illegal command indicates that the command word contains one or more parameters that cannot be complied with. Thus, upon the programmer 10's detection of any of these error conditions, it must retransmit the entire message.

The pulse generator status field, in turn, advises the programmer 10 of three possible status conditions (i.e. PG type, data acquisition port busy and data acquisition port available). If the response is to a READ command, the status field will typically indicate the availability of the data acquisition port. Otherwise, during all abnormal status responses the status field advises the programmer 10 of the PG type so as to permit the operator to confirm that the proper protocol is being used.

Returning to the description of FIG. 4, the I/O controller circuitry also contains a number of programmable pacing parameter registers that are coupled to the B BUS 40 and the C BUS 42. These registers are individually programmable by the programmer 10 and are used to store the necessary pacing parameters for the various modes of operation and to facilitate so called "scratch pad" operations. In particular, the programmable registers are the pace amplitude (PACE AMPL) register 56, the atrial sensitivity (ATRL SEN) register 58, the ventricular sensitivity (VENT SEN) register 60, the MODE 2 register 62, the PR interval (PR INT) register 64, the graceful degradation interval (GD INT) register 66, the graceful degradation onset (GD Onset) register 68, the P2 (i.e. UPPER RATE LIMIT (URL)) register 70, the P1 (i.e. ESCAPE PERIOD or LOWER RATE LIMIT (LRL)) register 72, the absloute refractory (ABS REF) register 74, the ventricular width (VENT WIDTH) register 76, the atrial width (ATRL WIDTH) register 78 and the atrial blank (ATRL BLANK) register 80, see FIGS. 5.12, 5.13, 5.14, 5.15, 5.19 and 5.22.

A number of scratch pad or accumulator (ACC) registers are also available to the I/O controller and PG controller circuitry. Specifically, the accumulator ACC 3, ACC 4 and ACC 5 registers 82, 84 and 86, are available to the I/O controller, see FIGS. 5.15 and 5.22 while the ACC 1 and ACC 2 registers 88 and 90, are available to the PG controller, see FIG. 6.19. While the accumulator registers can be read and written by the programmer 10, they typically are not programmed directly, as with the pacing parameter registers, but rather are used in a scratch pad fashion to facilitate normal operations. In passing, it is also to be noted that the ACC5 register 86 is coupled to shift multiplexer (SHIFT MUX) 92 and which, in turn, is controlled via the MODE 2 register so as to permit "right shifts with zero fill" of 2, 3, 4 and 5 bit positions, the operation thereof will however be described in greater detail hereinafter.

The P/G controller circuitry also contains a number of other registers, some of which are programmable and some not. The MODE 1 register 94, in particular, is programmable, see FIG. 6.17. The master time 96, on the other hand, is capable of only being read, while the auxiliary counter 98 can only be written so that neither is truly programmable, see FIGS. 5.19 and 6.18.

The programmer 10 via the above mentioned communications protocol, bus system, and addressable registers is thus able to communicate with most of the pacing registers as well as with most of the other circuitry coupled to the registers and/or the A, B or C BUSES 40, 42 and 44.

Continuing with the description of FIGS. 4 and 4a to 4d and assuming that a valid, error free READ or WRITE command has been received, that the appropriate buses have been selected and that data, if appropriate, is available in the S/P 0 and S/P 1 DATA registers 46 and 48, then a "buffer ready" flag will be set in the priority select/detect circuitry 100. There the flag will be stored along with any other flags that have been set during the cardiac cycle. The PG controller as it proceeds through the cardiac cycle will then periodically review these flags on the prioritized basis established by the instruction word then resident in the instruction decide circuitry 102 and perform a subroutine jump to the I/O subroutine when the buffer ready branch condition and time within the pacing algorithm is encountered. During the I/O subroutine, the algorithm then confirms which of the READ or WRITE commands has been received enables the source and destination registers and transfers the high and low bytes of data from the source registers to the destination registers, before returning to the instruction from which it jumped.

In particular, during a READ command, the C BUS 42 is deselected while the A and B BUSES 44 and 40 are selected so that the contents of the appropriate source registers are read via the A and B BUSES 44 and 40 into the ALU 106, see FIG. 6.16. There a zero is added to the contents of each of the just read source registers and the data is transfered to the S/P 0 and 1 DATA registers 46 and 48 via the C BUS 42. Next, the data is transfered via the serial port output bus 50 to the telemetry encode/decode circuitry 24, and from there it is transmitted to the external programmer 10.

Alternatively, during a WRITE command, the C BUS 42 is selected and the A and B BUSES 44 and 40 are deselected. The data in the S/P 0 and 1 data registers 46 and 48 is then consecutively read onto the B BUS 40 and transmitted to the ALU 106. There a zero is again added to the data and the data is transferred via the C BUS 42 to the appropriate destination registers as defined and enable via the B/C ADRS address field.

Concurrently and independently of the above communications, the PG controller circuitry operates in response to the operative programmed pacing mode to produce pacing pulses to the heart. While communications with the programmer 10 are necessary, the operation of the PG controller takes priority and therefore all other non-vital operations are overlapped on a non-interference basis. However, since many of these non-vital operations happen at the same or slightly staggered times depending upon the mode, it is necessary to prioritize operations. Thus, it is necessary that some operations be permitted to "interrupt" or take precedence over other operations and which interrupting operations are more important to the overall operation of the control circuitry. Such interruptions are accommodated via the interrupt circuitry of the controller, each of the interrupt vector logic circuitry 114, the I/O communications circuitry, the graceful degradation circuitry and the rate smoothing circuitry can generate interrupt requests.

When an interrupt request is made, it is made via the interrupt vector logic circuitry 114, see FIG. 5.11, as a consequence of receiving a request from either the sequence control logic 32, the power on logic circuitry 22, (i.e. during a magnetic rate MAG RATE operation), the graceful degradation control circuitry 116 or the analog-to-digital (A/D) converter circuitry 118, see FIGS. 5.16 and 5.17. When an interrupt request is generated, an interrupt vector of a specific value is coupled from the interrupt vector logic circuitry 114 to the B BUS 40. The vector is then read by the ALU 106, for example, near the beginning of the absolute refractory period for that cardiac cycle. The ALU 106, upon reading the interrupt vector, next adds the vector value to the value then resident in the memory address register (MAR) 126 and which value is coupled via the auxiliary memory address (MA) BUS 186 to the ALU 106 by way of the A BUS 44 and the disabled complement circuitry 124. The sum of the values in the interrupt vector and MAR registers 114 and 126 is then loaded into the memory address register (MAR) 126m, see FIG. 6.7; so as to establish the address of the next instruction to be read from the pulse generator 14's instruction or read only memory (ROM) 128, see FIG. 6.3. The loading of MAR 126, as just described, thus ensures that the next instruction read is the desired interrupt instruction and which produces the desired priorities of operation. It is also to be noted that only eight of such interrupt vectors have been included in the present apparatus, although more or less can be included as required.

As mentioned, interrupt requests are generated via a number of different circuits elements. For instance, assuming that the MAG RATE function is enabled, an interrupt request will be generated to initiate the MAG RATE condition unless previously disabled. Such a condition is enabled when the operator moves a magnet into close proximity with the pulse generator 14 so as to close the normally open reed switch 130 and which action causes the pulse generator 14 at the start of the next cardiac cycle to revert to a pacing rate that is demonstrative of the battery voltage. In particular, at the beginning of life (BOL) the pulse generator 14 will revert to an asynchronous rate of 100 bpm and, as the battery degrades towards the end of life (EOL) or approximately 2 volts, the rate will revert to approximately 85 bpm.

The specific rate at which the pulse generator operates is dependent upon a reading obtained from the A/D converter 106 and which reading is scaled relative to the 15 beat increments that exist in the defined 100 bpm to 85 bpm range. In particular, a scaled factor corresponding to battery condition is determined and added to the 600 millisecond period of the 100 bpm base rate and which sum is stored in one of the accumulator registers for subsequent comparison with the count of the auxiliary counter 98. During subsequent cardia cycles and once the count in the counter 98 matches the scaled sum, pacing pulses will thereafter be produced at an asynchronous rate between 85 and 100 bpm depending upon the batteries condition, so long as the magnet is applied. Once the magnet is removed, the pulse generator 14 resumes pacing in the programmed mode at the programmed rate.

It is to be noted, though, that the MAG RATE interrupt can be disabled and which is accomplished via the programming of the least significant bit of the MODE 2 register 62 to a binary "0", see FIGS. 5.11 and 5.19. Such an action essentially prevents the generation of the interrupt vector, inadvertent or otherwise, and which is important for patients with ischemic hearts (i.e. individuals who are not able to accommodate the demands of the higher MAG RATES).

Other interrupt requests can also be generated via the graceful degradation control logic circuitry 102, upon the timing out of the graceful degradation onset interval. Similarly, data acquisition and serial port interrupt requests can be generated in response to various I/O commands. In general, though, each of these requests produces a different vector that affects the instructions that are performed during the remainder of the present or subsequent cardiac cycles.

Continuing on with the description of the I/O controller circuitry, attention is next directed to the digital-to-analog (D/A) interface circuitry that is used to decode the various programmed parameters and sense and/or pace the proper heart chambers. In particular, attention is directed to the two, 4 bit digital-to-analog (D/A) converters 132 and 134 and to the two, 6 bit D/A converters 136 and 138, see FIGS. 5.14 and 5.18. These D/A converters are used to control the atrial and ventricular pacing pulse amplitudes and the atrial and ventricular sensitivity thresholds. The pacing amplitude is determined in part by selecting and coupling the four least significant of the eight bits of data stored in the PACE AMPL register 56 to the D/A converter 108. The other four bits of the PACE AMPL register 56 are then selected and coupled via the multiplexer 140 to the converter 134, as opposed to the corresponding nominal ventricular sensitivity bits that are also coupled to multiplexer 140, via conductor 142 and the MODE 1 register 94. The four bit outputs from the two D/A convertors 132 and 134 are then wire OR'ed together and the subsequent sum of the two analog currents determines the pacing amplitude established by the analog chip and which for the presently preferred embodiment is established to be the same.

Similarly, the atrial sensitivity is determined by selecting and coupling the least significant six bits of the atrial sensitivity value stored in the ATRL SEN register 58 to the D/A converter 136 via multiplexer 141. This digital value is then converted into an analog current which determines the atrial sensitivity threshold on the analog chip. In turn, the ventricular sensitivity is determined by coupling the least significant six bits of the ventricular sensitivity value stored in the VENT SEN register 60 and multiplexing and selecting this value over the nominal ventricular sensitivity value that is also coupled to multiplexer 144 via conductor 142.

Thus, depending upon the programmed mode either one or the other or both of the programmed atrial amplitude and sensitivity values or the programmed ventricular amplitude and sensitivity values can be selected. Also, depending upon the mode and parameters desired, either or both of the pre-programmed nominal ventricular amplitude and sensitivity values can be selected. It should also be noted that one of the two extra bits in the sensitivity registers 58 and 60 is unused, while the other serves as a unipolar/bipolar lead configuration select bit for shorting the sensing portions of the leads 16B and 16A to the pulse generator container, when unipolar operation is desired or vice versa. Still further, it should be noted that the constants in registers 139, 143 and 145 permit the selection of additional sensing thresholds and pacing amplitudes.

Next, attention is directed to the analog-to-digital (A/D) converter circuitry 118, which is shown in greater detail in FIGS. 5.16 and 5.17, and which contains circuitry for monitoring various sensed of heart functions as well as various other body functions. These functions can thereby be individually sensed and converted into digital values which, in turn, can be evaluated by the operator or external programmer 10. At present, however, the A/D converter circuitry 118 is used primarily for interrogating the battery to determine its remaining life, such as during the MAG RATE or batter check conditions, but the circuitry has been designed to permit the expansion of the pulse generator 14's capabilities to sense additional body functions.

Requests to interrogate such conditions can be initiated by the programmer 10 via the flagging of the interrupt request port and the loading of the data acquisition address register 146 with the appropriate control word, which upon being decoded via the address decode circuitry 148 causes an A/D request to be made to the analog circuitry (not shown). The desired data is then read at the data acquisition output port. Alternatively, a MAG RATE request can be executed under algorithm control upon flagging the MAG RATE port. In any event though and depending upon the requests, the select 0 and 1 (SEL 0 and 1) A/D request ports are enabled as well as the appropriate inputs lines so as to couple appropriate signals to the analog circuitry and analog data back to the selected input lines in response thereto. At present, this data takes the form of a reference current (REF I) and an unknown current (IX) and one or both of which are converted within the converter 118 into digital values that are used to indicate the MAG RATE or are transmitted to the programmer 10 via the B BUS 40 and an enable output signal to indicate battery condition. It is also to be noted that when such requests are not being made, the A/D converter circuitry 118 is not powered up, thus saving power.

As mentioned, the programmer 10 can interrogate the battery directly via the MAG RATE condition to determine its present function and approximate remaining life. During a direct interrogation, a WRITE command from the programmer 10 causes the A/D converter 118 to be enabled and an appropriate 8 bit data acquisition address to be written into the data acquisition address register 146 via the C BUS 42. This address is then decoded via the acquisition address decode circuitry 148 so as to produce an appropriate select signal and enable the receipt of the proper analog data. In particular, the battery current IX is selected and the analog value is converted into a digital value that is transmitted to the programmer 10.

On the other hand, during a MAG RATE condition, the other of the two presently available select codes is impressed under algorithm control on the analog circuitry and which responsively couples both of the REF I and IX currents to the converter 118. Prior thereto however the pacing algorithm and PG controller circuitry pace the heart at a rate of 100 bpm for two cardiac cycles. After the first beat, the REF 1 and IX currents are selected to determine a worst case battery condition, since such a condition typically occurs immediately after a paced event, when the most current has been withdrawn from the battery. And, after the second beat, the data is read out of the convertor 118.

The conversion then of both of the analog currents to a digital value by the above converter 118 occurs via the coupling of the current inputs to individual ring oscillators internal to the A/D converter 118, see FIG. 5.17, and which in turn, cycle at a frequency proportional to the magnitude of their respective IX and REF I current inputs. The ring oscillator outputs are next monitored via associated REF I and IX counters and after approximately 64 milliseconds or 128 clock cycles of the reference ring oscillator, the counters are turned off. At that point, one of the counters contains an unknown count that is proportional to the unknown current and the other contains a known count that is proportional to a known current.

The pacing algorithm next causes the unknown count to be loaded via the B BUS 40 into an accumulator register, before the A/D converter circuitry 118 and analog circuitry are powered off. The unknown count is then scaled and added to the 600 millisecond period of the predetermined 100 bpm base rate, thus determining the period of the subsequent pulses during the MAG RATE condition and the rate of which is a measure of the battery condition.

In passing, it is to be noted that the scaling is accomplished in part via the ACC 5 register 86 and shift multiplexer 92 and which right shift and zero fill the unknown digital value. This value is then inverted and the five least significant bits are selected as the scaled result which is added to the period of the base rate. It should be noted too that if the battery voltage is greater than or equal to 2.8 volts, the scaled value will be 0 and the MAG RATE 100 bpm; and if the battery voltage is less than or equal to 2.0 volts, the scale value will be 15 and the MAG RATE 85 bpm.

Referring next to the MODE 1 and 2 registers 94 and 62 and depending upon the desired mode of operation, an appropriate mode value is written by the operator via the external programmer 10 into three bit positions of each of the respective MODE 1 and 2 registers 94 and 62, see Table 4 and FIGS. 5.19 and 6.17.

TABLE 4

| MODE VALUES | | |
|---|---|---|
| MODE VALUE | DESCRIPTION | |
| 000 | VENTRICULAR DEMAND | (VVI) |
| 001 | R-WAVE SYNCHRONOUS | (VVT) |
| 010 | ATRIAL DEMAND | (AAI) |
| 011 | P-WAVE SYNCHRONOUS | (AAT) |
| 100 | DOUBLE DEMAND SYNCHRONOUS | (DDD) |
| 100 | **A-V SEQUENTIAL | (DVI) |
| 110 | *P-WAVE SYNCHRONOUS DEMAND | (VDD) |

*Disable Atrial Pacing (i.e. program atrial width to zero)
**Disable Atrial Sensitivity (i.e. program atrial sensitivity to Infinity)

During the cyclical operation of the I/O and PG controller circuitry, these values enable various portions of the circuitry and generally ensure the proper operation of the circuitry along with the various programmed instructions. In particular, the value stored in the MODE 2 register 62 enables the auxiliary counter 98 as well as the graceful degradation and rate smoothing functions, after being decoded by the mode decode register 152 and disables the MAG RATE function and controls the number of bit positions shifted and zero filled by the ACC5 register 86. Similarly, too, the value stored within the MODE 1 register 94 is interpretted by the PG controller and used to establish the proper operation thereof as well as to indicate the reasons why the PG controller reverted, if it had, to a nominal parameter mode. The MODE 1 register 94 also establishes the basic type and manner of single chamber or dual chamber and atrial or trigger modes of operation.

If a dual chamber mode of operation is selected along with either the graceful degradation and/or rate smoothing functions, then the value stored in the MODE 2 register 62 interacts with the selected pacing mode to establish the requisite priority and timing necessary to accommodate the selected functions. For example, if the graceful degradation function is programmed, the mode select circuitry 152 produces a graceful degradation enable signal that is coupled to the graceful degradation (GD) circuitry 116 and to the interrupt vector logic circuitry 114. At the same time the auxiliary counter 98 is enabled via the instruction word, which, in turn, flags the GD circuitry 116 when its count equals zero. The GD circuitry 116 then flags the interrupt vector circuitry 114 and in response thereto a graceful degradation interrupt request is produced and the branch condition select circuitry 100 is flagged. If, on the other hand, the rate smoothing function is programmed or if both functions are programmed, the mode decode circuitry 152 also produces a rate smoothing enable signal or flag that too is coupled to the branch condition select circuitry 100 and taken into account as the priority conditions are selected by the branch condition select circuitry 100. Depending upon whether or not and which types of other priority signals are present, the priority select circuitry 148 then establishes the appropriate priority for the various branch conditions that are required to perform the programmed function. The priority conditions relative to the various branch conditions will, however, be described in greater detail hereinafter with respect to FIG. 9, Table 6 and the fields of the typical instruction word.

Figure 7:
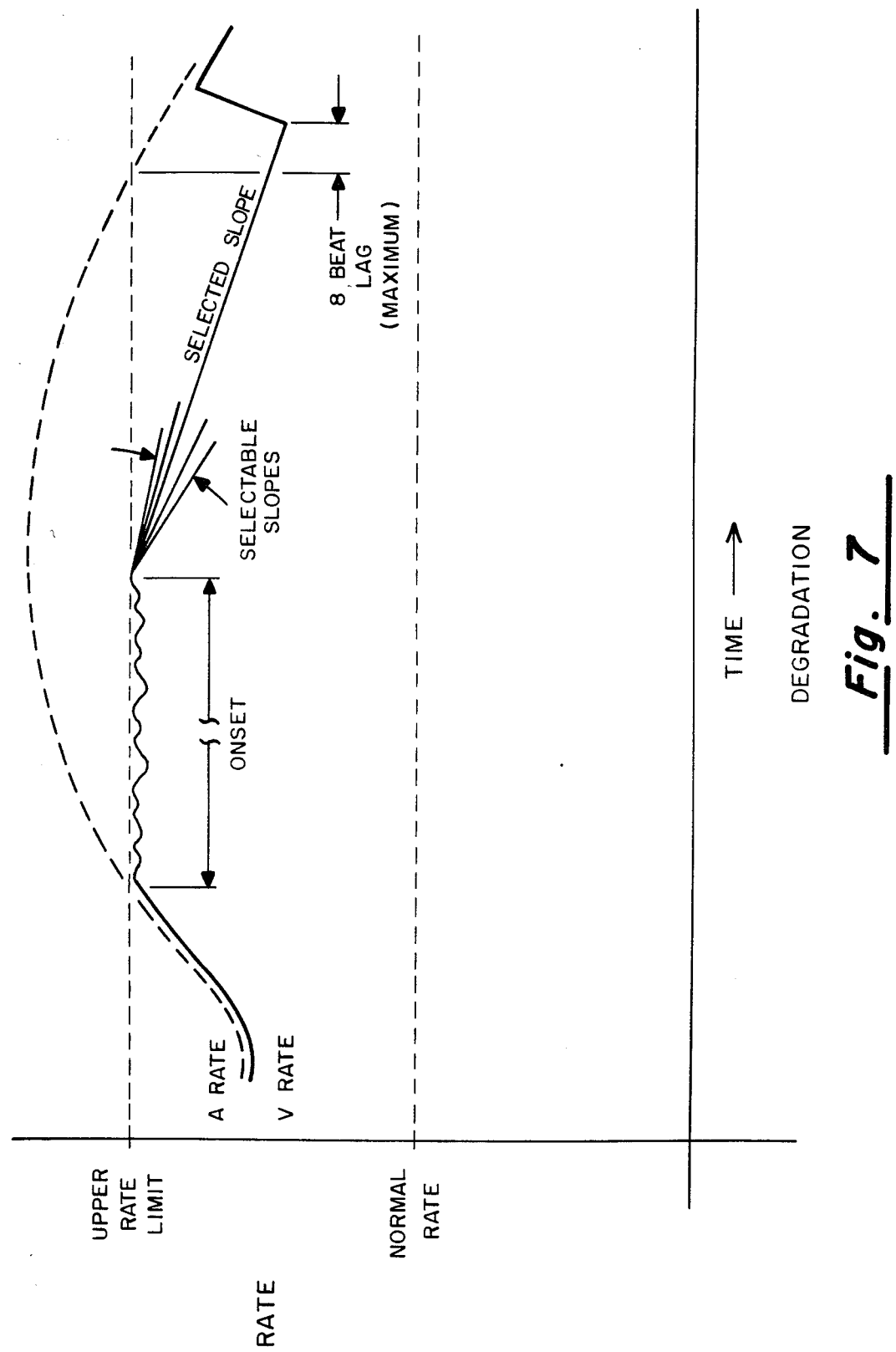
FIG. 7 shows an exemplary waveform demonstrating the effects of graceful degradation.

Again, if the graceful degradation function is programmed, the control circuitry, after decoding the mode of operation and prioritizing the branch conditions, acts in the fashion of FIG. 7 to reduce the ventricular pacing rate has, if the atrial rate exceeded the programmed upper rate limit for a sustained period. In particular, the control circuitry causes the period of the ventricular pulses to increase in a linear fashion and consequently the ventricular rate to decrease hyperbolically back to the programmed rate. The actual rate or slope of decay is programmable via the GD INT register 66 along any one of 256 different slopes, and the ventricular rate is reduced in a stepped fashion after a predetermined number of detected atrial beats. As a further enhancement to the graceful degradation function, a programmable GD onset interval is also provided so as to permit the operator to program an interval between 1 and 2048 beats and before which the graceful degradation function cannot be enabled, even though the atrial rate exceeds the programmed URL. This GD onset interval or time delay thus permits the pulse generator 14 to accommodate periods of high naturally increasing atrial rates, such as during exercise. In particular, it is achieved via the loading of the auxiliary counter 98 with the programmed GD onset value from register 70, after detecting a graceful degradation interrupt request. The counter 98 is then decremented each cardiac cycle for which the atrial rae exceeeds the programmed URL, and upon reaching zero, the control circuitry acknowledges the graceful degradation request and begins to monitor the atrial rate and vary the effective URL.

Before continuing, it is also to be noted that the graceful degradation circuitry 116 contains a 3-bit counter, see FIG. 5.20, that monitors the atrial rate relative to the upper rate limit. If the atrial rate exceeds the upper rate limit, it is incremented, otherwise it is decremented. This counter thus monitors the number of atrial beats that are above the URL relative to the number that are below the URL. If the number of early beats exceeds the number below the URL by eight, over a period of time, then the effective pacing rate is reduced by adding the value in the GD interval register 66 to the URL. Thus, it is to be noted that the effective URL value changes with time as more and more of the incremented GD intervals are added and whereby the rate is reduced to the LRL. Stated differently, a cummulative sum, starting with the programmed period of the upper rate limit is maintained and which produces successively decreasing effective URL values, until the period of the ventricular pacing pulses is increased to the programmed normal period.

It is also to be noted that if the number of late atrial beats or those below the URL exceeds the number of early atrial beats by eight, over a period of time, then the counter will reach zero. And, if the count remains at zero for two consecutive auxilliary counter time-outs, then the control circuitry will exit from the graceful degradation function.

Figure 8A:
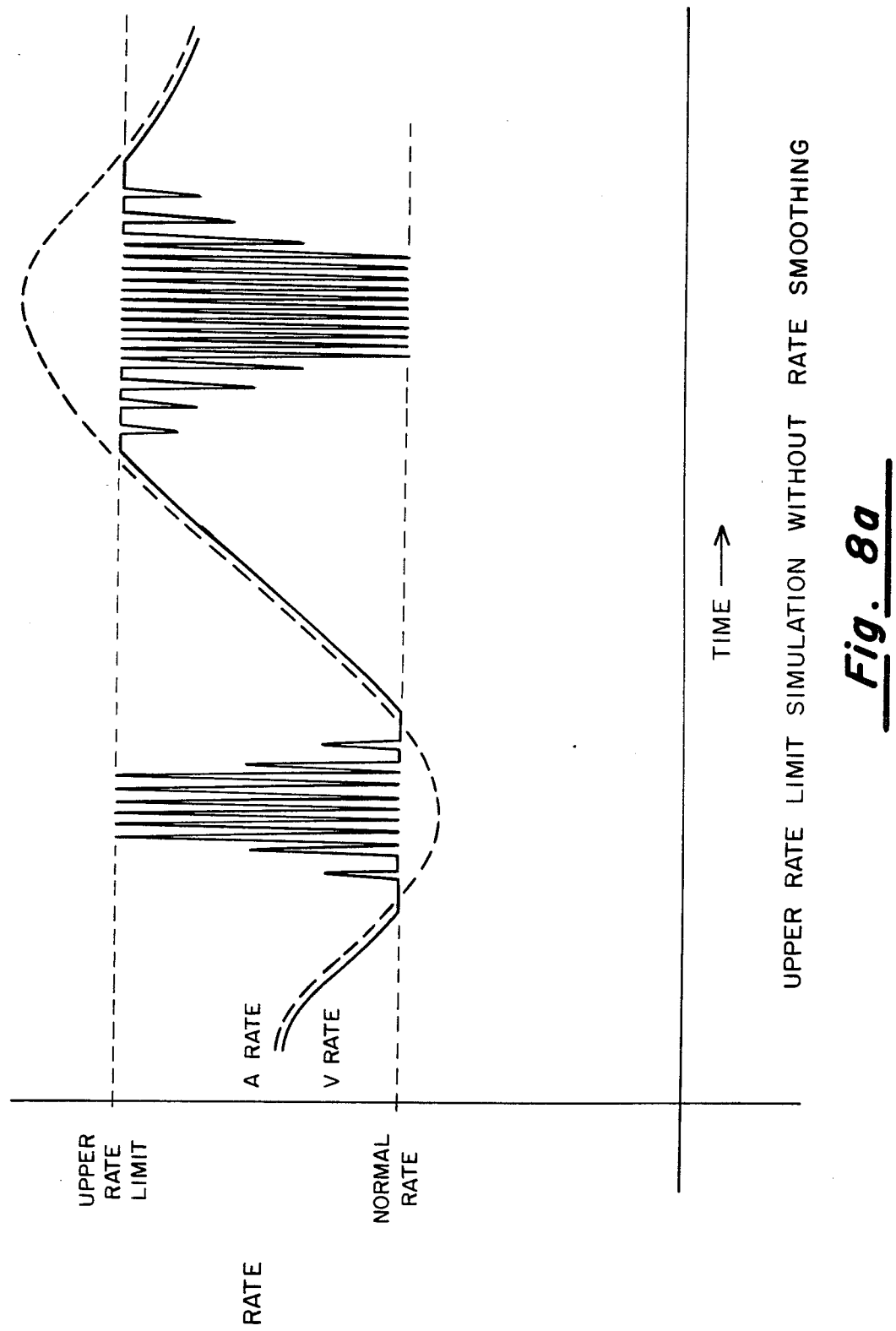
Figure 10A:
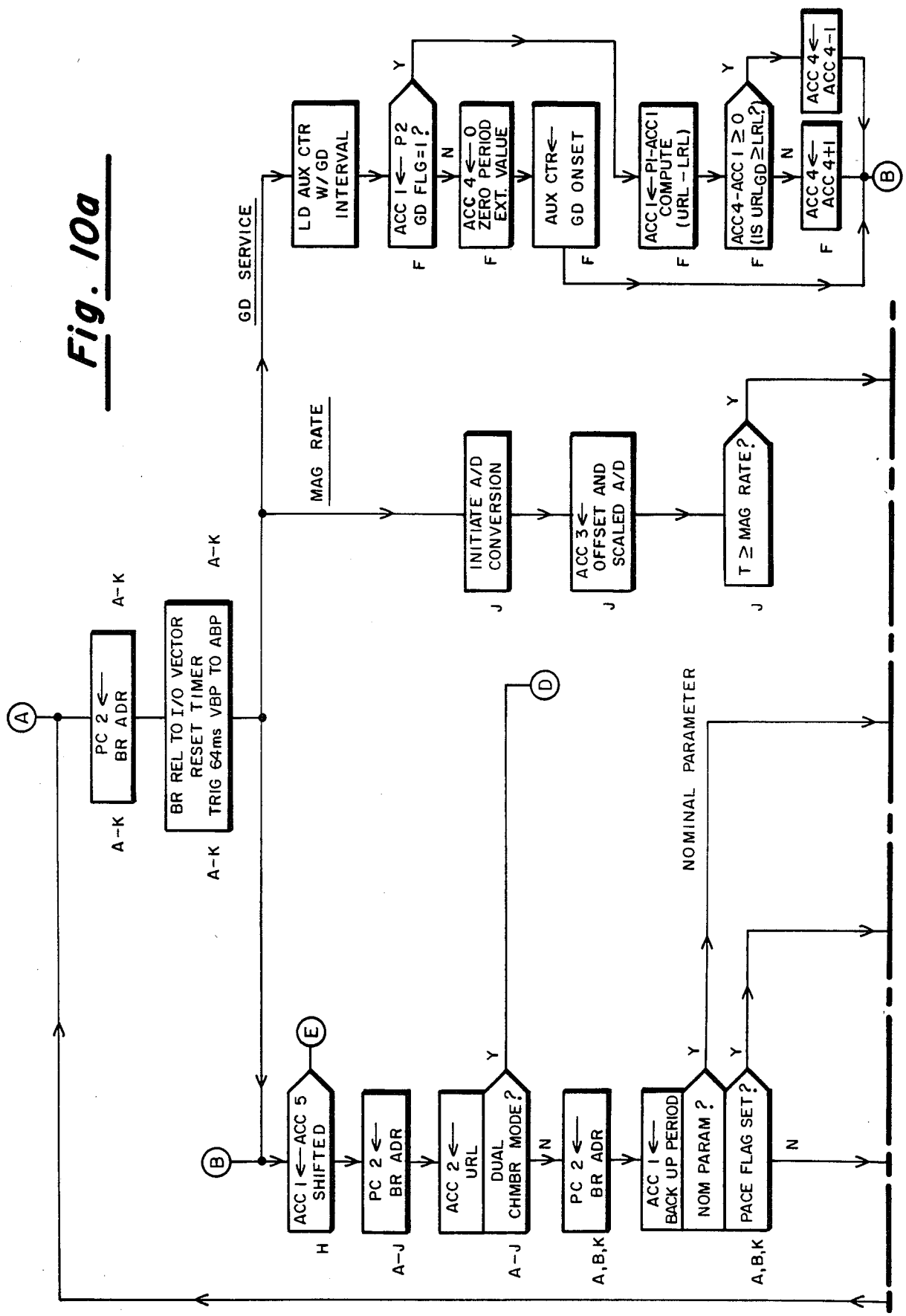
FIG. 10, comprised of FIGS. 10a to 10g, shows the flow chart of the operation of the I/O and PG controller circuitry during the various pacing modes.
Figure 10B:
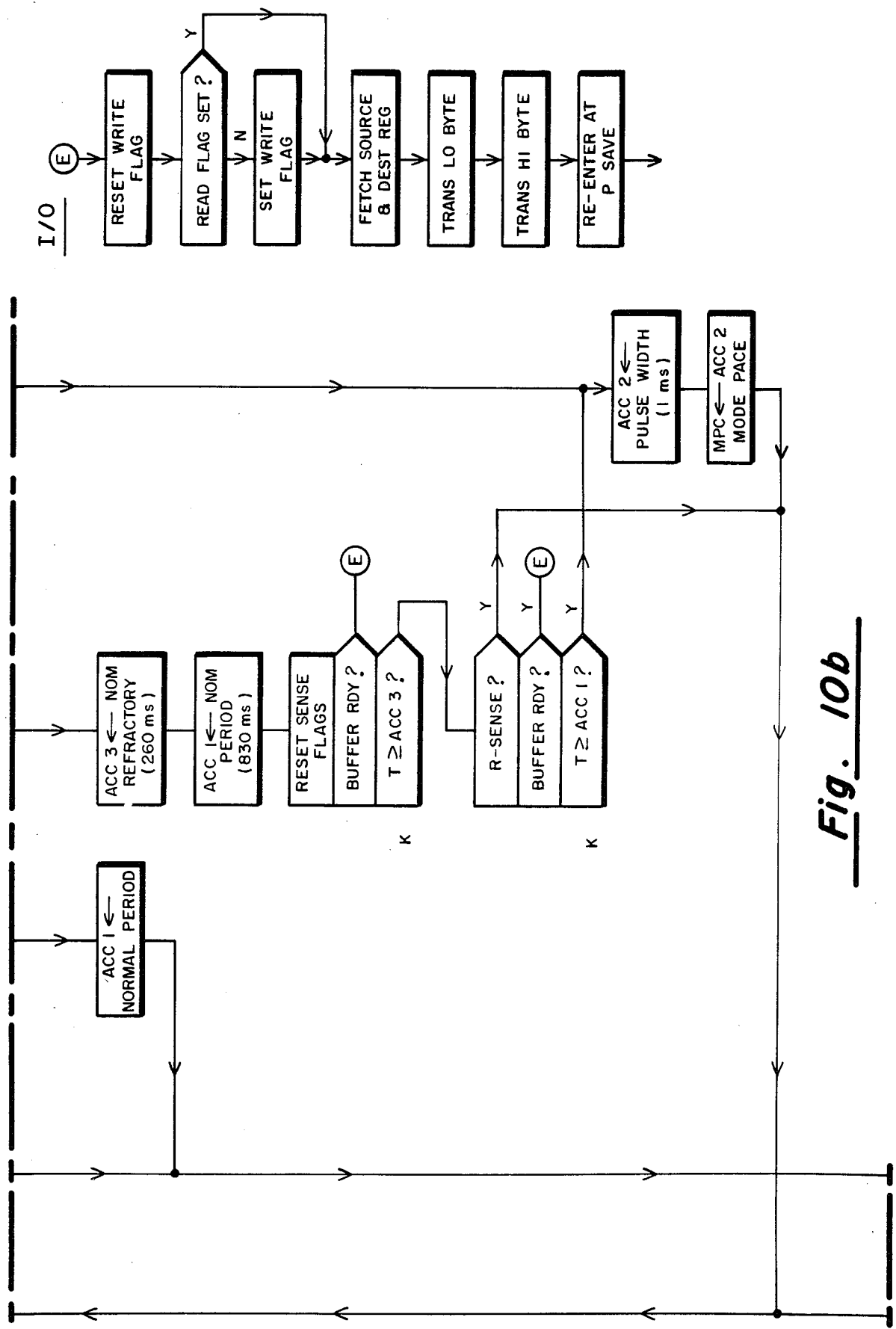
Figure 10C:
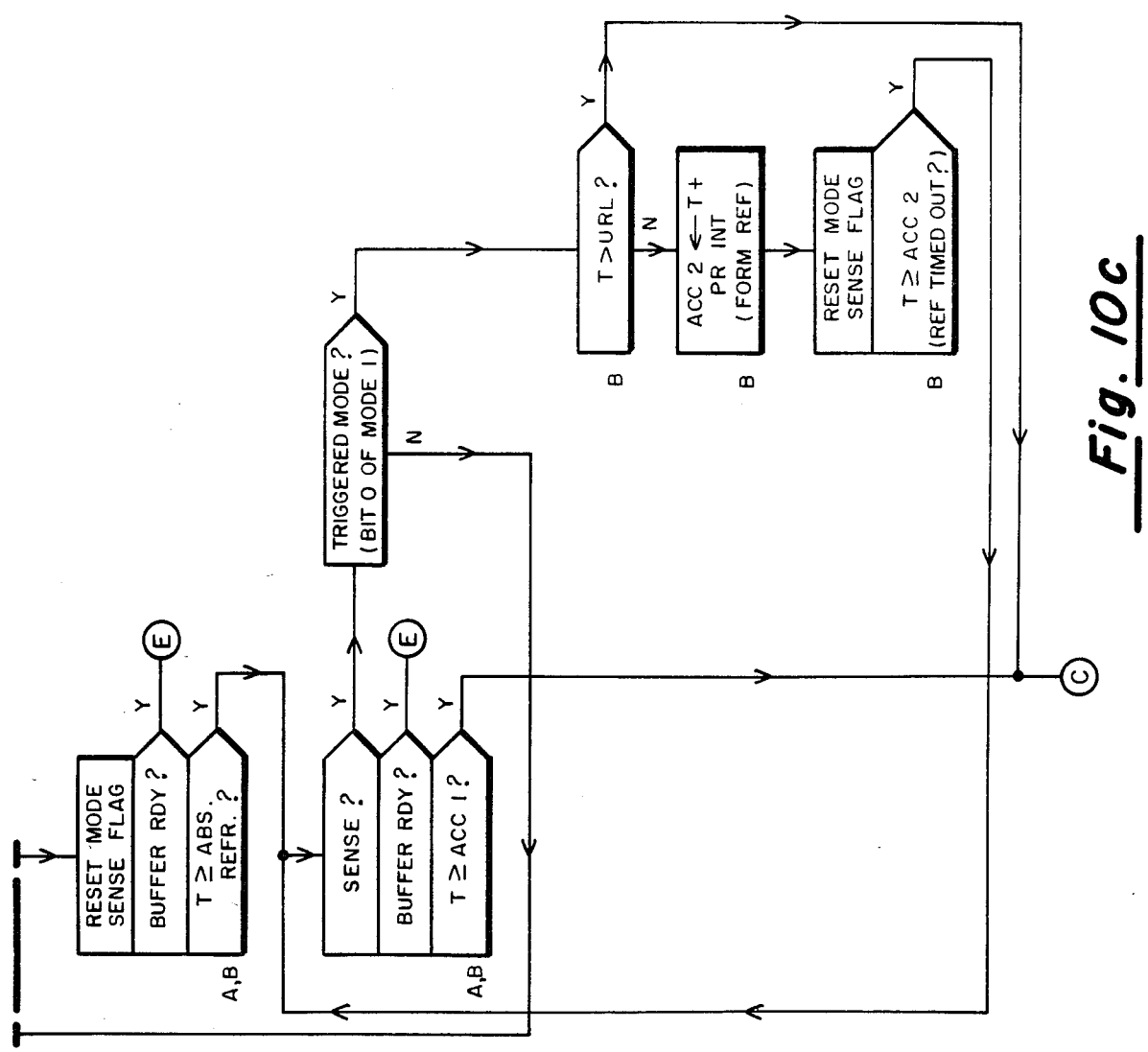
Figure 10D:
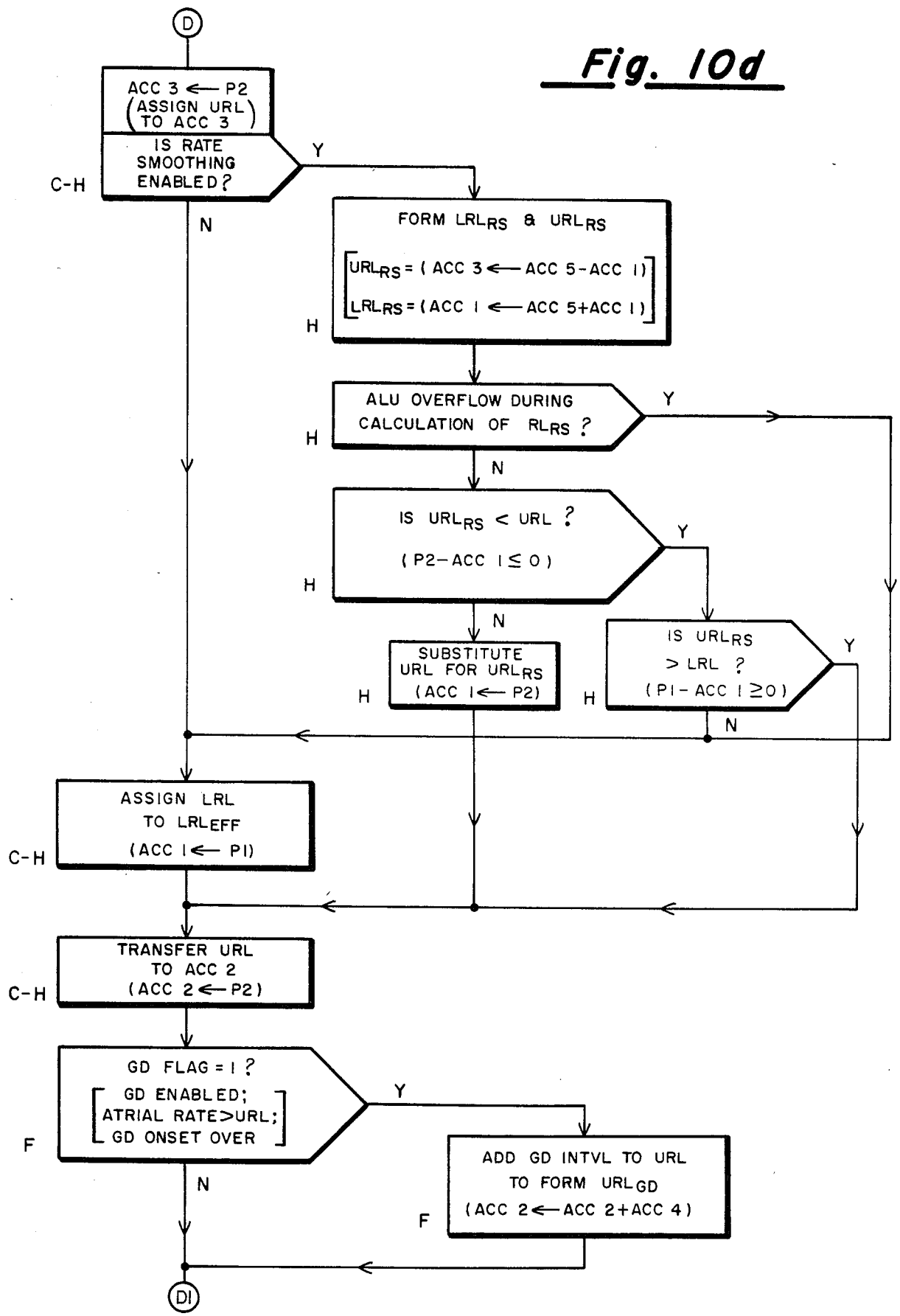
Figure 10E:
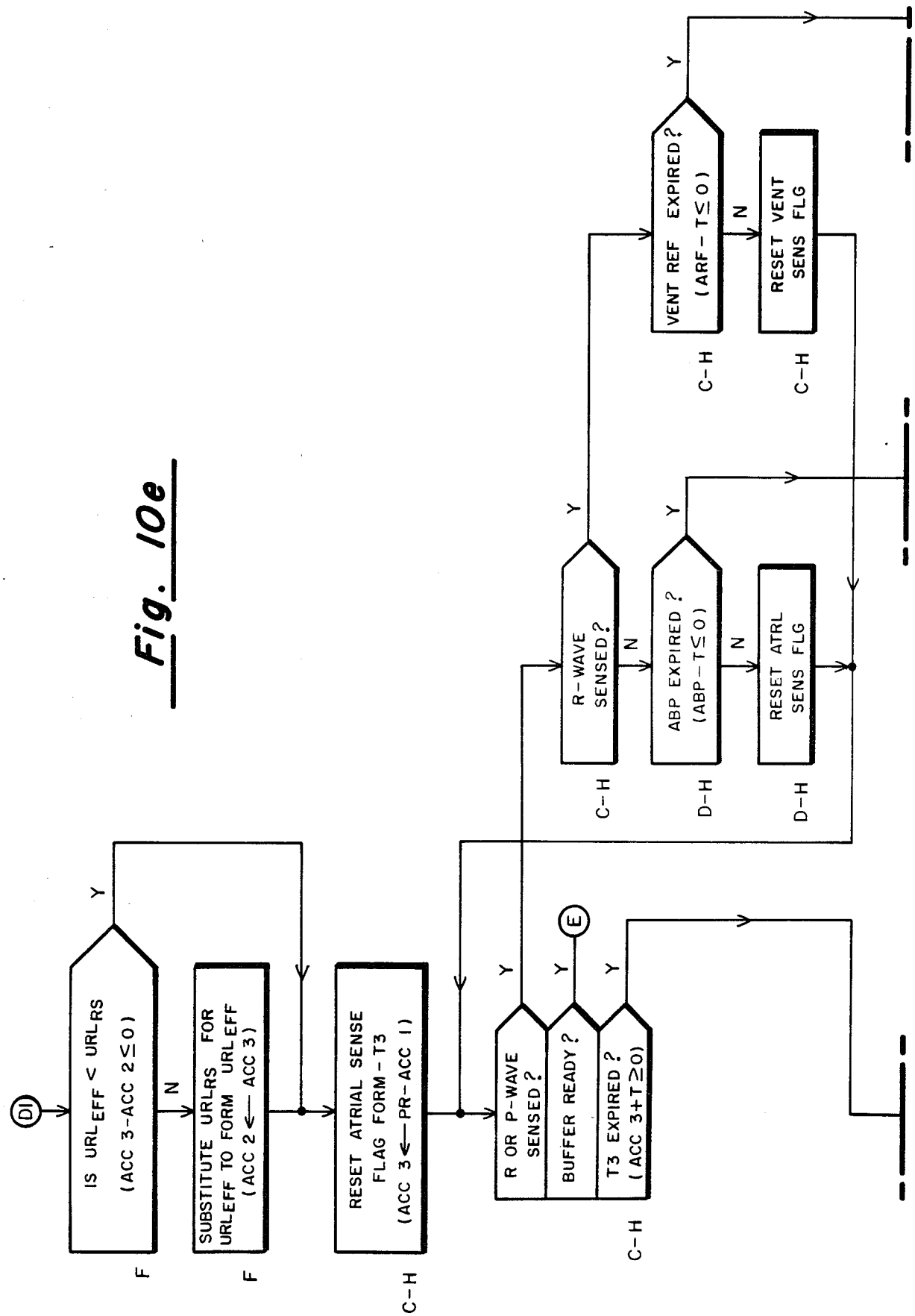
Figure 10F:
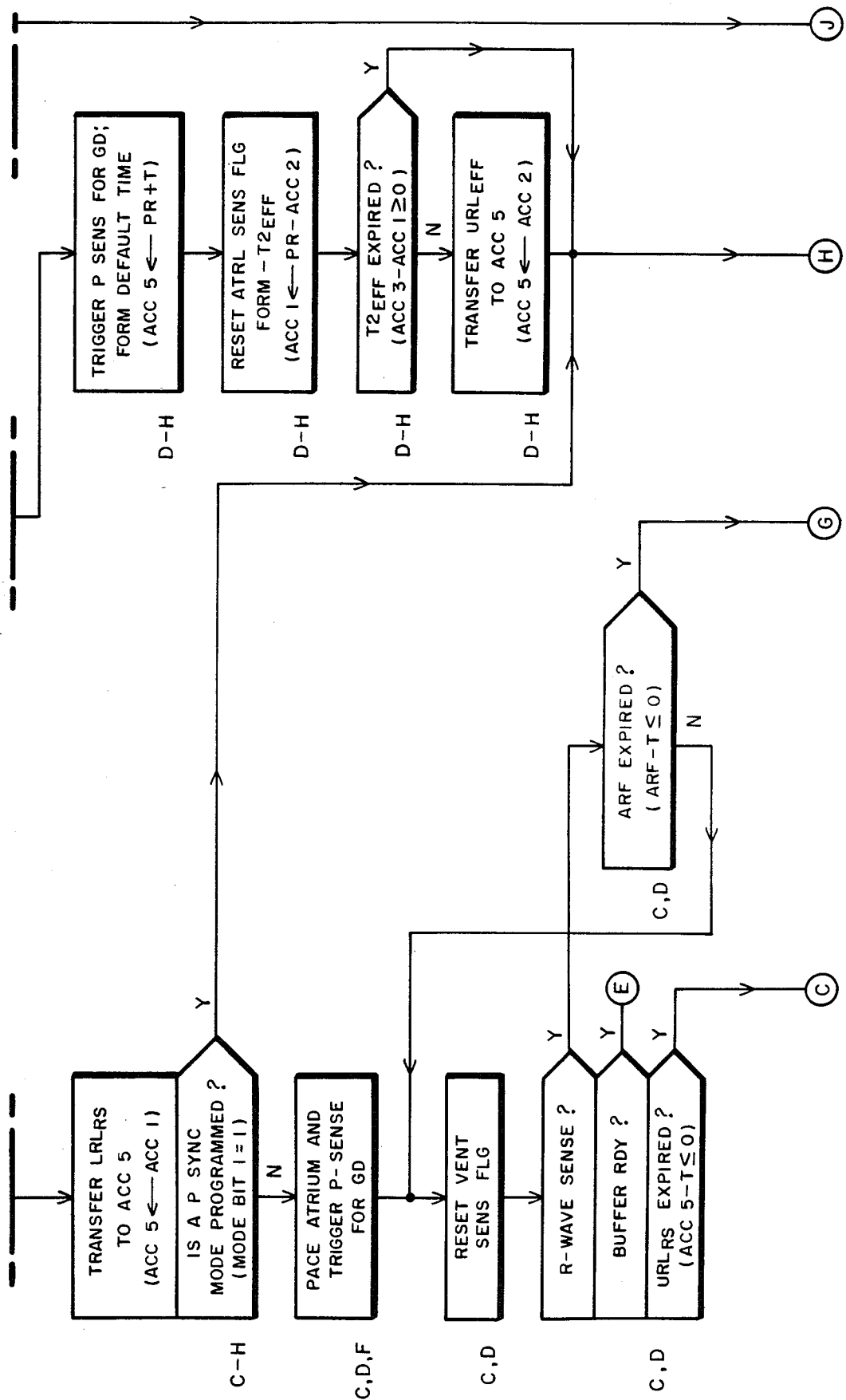
Figure 10G:
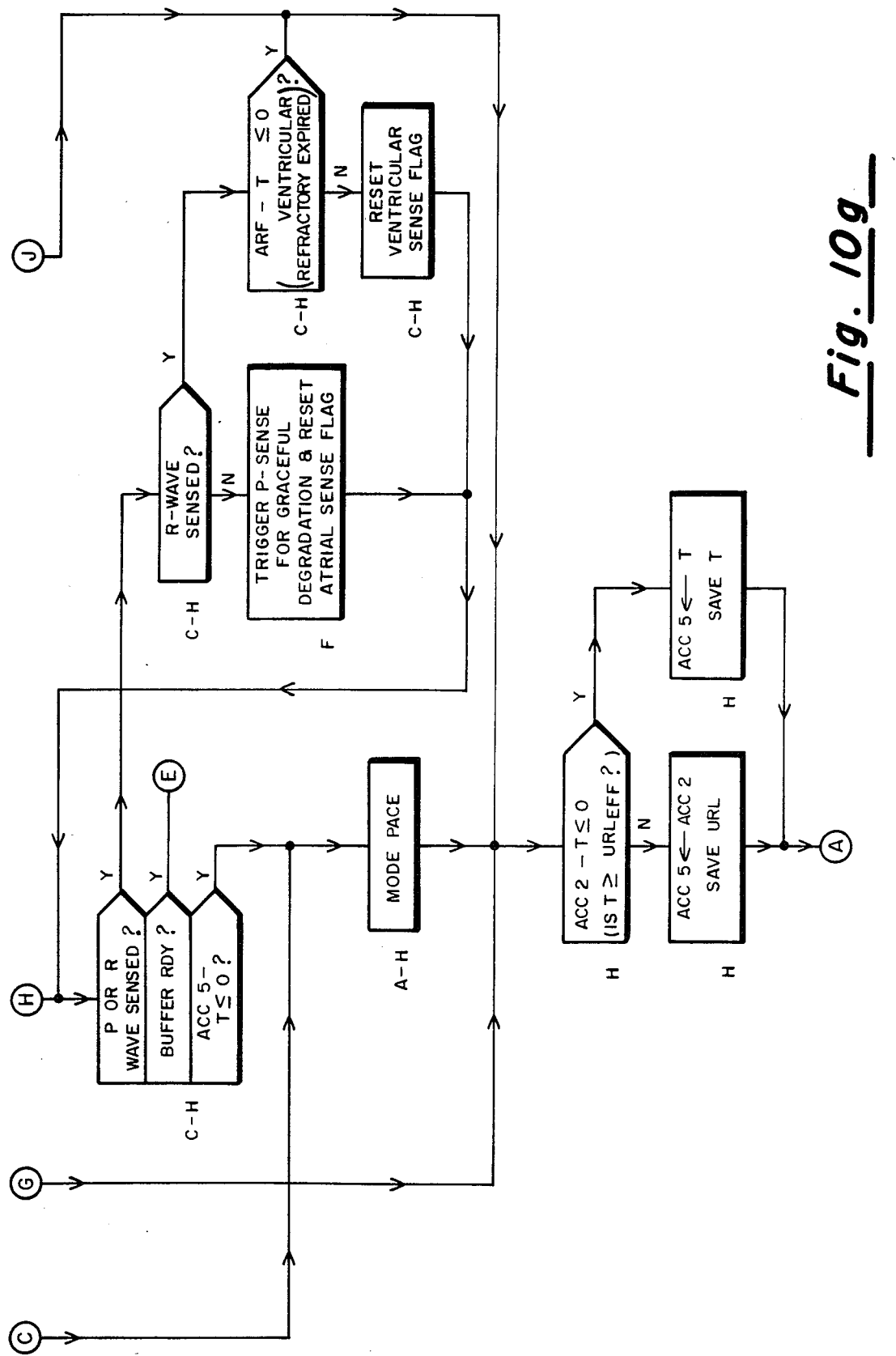

Rate smoothing, on the other hand, provides a measure of control over the rate of change of the ventricular pacing rate. Specifically, the rate of change of the ventricular pacing rate is controlled on a cycle-to-cycle basis so as to maintain the rate of change within a programmed percentage of the previous cycle's rate. This function is achieved via the comparison of the ventricular pacing rate for each cycle to a "rate window" or percentage of the period for the previous cardiac cycle so as to ensure that the period of the pacing pulses is constrained from cycle to cycle by the limits defined by the rate window. If the atrial rate changes by more than the limits of the rate window for each cardiac cycle, then the rate smoothing circuitry and routine stored in ROM 128 constrains the ventricular pacing rate change to the maximum allowed by the rate window. Attention is also directed to FIGS. 8a and 8b, where "before" and "after" examples are shown of a worst case atrial rate that "before" exhibits long and short intervals from cycle-to-cycle, whereas "after" selecting rate smoothing, the rate of change in the ventricular rate is diminished substantially so that a relatively sustained ventricular rate is established about the programmed rate and upper rate limit.

Referring now to the branch condition select circuitry 100 and FIG. 5.11, it is to be noted that its inputs are flag signals from the graceful degradation control circuitry 116, the auxiliary counter 98, the sequence control logic circuitry 32 (i.e. the interface control circuitry thereof, see FIG. 5.8) and the mode decode circuitry 152. Depending upon the instruction word resident in the instruction decode circuitry 102, see FIGS. 6.10 and 6.14, for any given cardiac cycle, the priority between the various flags is determined by the branch condition selects that are coupled thereto via the branch condition select bus 154.

For the moment and without discussing the priorities between the various potential flags, but which will be described in greater detail hereinafter with respect to FIG. 9, upon decoding the branch condition selects, three bits of binary information are impressed upon the select terminals of the branch condition select circuitry 100 and the priority 1,2 and 3 multiplexers 156, 158 and 160, see FIG. 6.3. There the branch select signals cause the selecting of one flag from amongst the various flags resident at the inputs to each of the multiplexers 156, 158 and the 160 and three priority detect signals from the branch condition select circuitry 100. The priority detect signals indicate if rate smoothing or graceful degradation or an I/O transaction have been requested and they are wire "OR'ed" with the priority detects from the priority multiplexers 156, 158, and 160 and transmitted via the three bit priority detect bus 162 to the priority arbitrator 164. There the prioritized flags are used to select the address of the next register via the memory address source register select circuitry 166 if it is enabled by the microinstruction, to be coupled to the MA BUS 122 and which register will contain the next instruction address in ROM 128, see FIG. 6.5. Possible next address registers include the P+1, P SAVE, PC 2 and I/O ADRS CONSTANT registers 120, 166, 168 and 170. Also, the contents of the C BUS 42 or the utility field may be selected.

Attention is also directed to the B/C BUS decode logic circuitry 172, see FIGS. 5.9 and 5.10 and which via the B/C SELECT BUS 174 selects which programmable register is read onto the B BUS 40 or is written from the C BUS 42, after decoding the five bit B/C SELECT field in the instruction word resident in the instruction decode circuitry 102 and produces the corresponding enable signals. In order to conserve I/O pins, the B/C SELECT BUS 174 is multiplexed within the B/C bus decoder circuitry 172. The B/C bus decode circuitry 172 is also operative in response to the T1 and T3 clock signals that are produced by the system clock, see FIG. 6.1.

The T1 and T3 clock signals are produced by dividing a 32 kilohertz clock signal down to a 2 kilohertz clock and which is used to produce the T1, T2 and T3 clock signals and which signals are delayed from one another by 500 microseconds. Also, it should be noted that the system clock provides for 8 kilohertz and 128 hertz clock signals.

Continuing the description of FIG. 4 and to the extent not already discussed, the PG or pacing control circuitry will now be discussed in detail. While the primary purpose of the I/O control circuitry is to enable communications between the external programmer 10 and the pulse generator 14, the purpose of the PG control circuitry is to control the acutal pacing of the heart per the programmed one of the various pacing modes and the associated parameters. Generally, the PG controller performs its function in a micro-controlled fashion by reading the necessary micro-instructions from ROM 128 and decoding the various fields of the instruction words, as with the I/O command words, so as to ensure the proper sequence of events during the selected mode of operation and its associated instruction set.

The ROM 128 is accordingly sized to accommodate the necessary instructions and which for the present embodiment accommodates 256 words that are each 30 bits wide. ROM 128 is also divided into two halves (i.e. paged) so that when accessing memory, it is necessary to check a ROM page bit to see which half of the ROM is to be accessed before powering up the selected half. Power is then only applied for a time sufficient to read the instruction and latch it into the memory data latch (MEM DATA LATCH) 176, see FIG. 6.9, again saving power. It is to be noted too that while 256 words can be accommodated, the present embodiment actually only employs approximately 80 words and which are equally divided between the halves or pages of ROM 128. Also, it is to be noted that ROM 128 is mask-programmable so that its contents can be changed, from time-to-time, to accommodate improvements etc.

While numerous methods of partitionment and operation can be employed to control ROM 128, the present method and architecture proves to be beneficial in that power is saved without a great deal of additional circuitry. Thus, due to the high parallel activity architecture, the instruction/cardiac cycle time is relatively small. In particular, because it is typically necessary to only perform on the order of 15 instructions during a cardiac cycle of, for example, 800 milliseconds and an instruction cycle of 4 milliseconds, the ROM 128 is sitting idle for approximately 740 milliseconds. While the actual idle time depends upon the number of instructions, it has been applicant's experience that the actual duty cycle of ROM 128 is only on the order of one to three percent and therefore the present accessing method and architecture is deemed adequate, but it is to be recognized that many other methods could be employed.

Upon reading an instruction from the ROM 128, it is decoded via the instruction decode circuitry 102. While each of functional fields of an instruction word will be described in greater detail hereinafter with respect to FIG. 9; generally, the instruction decode circuitry 102 acts to decode the various fields so as to determine the source and destination buses from amongst the A, B and C BUSES 44, 40 and 42, the priority amongst the various branch condition flags and the functional assignment of the utility field.

As mentioned, depending upon the instruction word and programmed mode, up to three branch condition selects are specified for each instruction. At the same time the priority between the selected branch conditions is determined by the priority enable bits that too are contained within each instruction word. In particular, the priority assigned by the priority arbitrator 164, see FIG. 6.4, depends upon the priority enable signals on the PRIORITY ENABLE BUS 178 and which cause the selection from amongst the wire "OR'ed" priority detect signals from the branch condition select circuitry 100 and the priority multiplexers 156, 158 and 160. The PG controller therefore selects the register coupled to the MA BUS 122 with the highest enabled, arbitrated priority when the MAR select circuitry 166 is clocked, and thereby ensures that the function with the highest priority is performed first.

For example, during one of the single chamber demand modes, a two-way branch condition could occur where the pulse generator 14 could either pace after a given time had elapsed or else reset the master timer 96 upon the detection of a sensed heart activity. These two conditions would then be monitored on a prioritized basis by multiplexers 156, 158 and 160. In particular, the priority multiplexer 156 would monitor the sense flag from the sense flag controller 180 at the priority 1 flag input terminals, while the priority three multiplexer 160 would monitor the flag input indicative of the time-out condition. Then as the branch conditions occurred and upon the clocking of the priority arbitrator 164, one of the flags would be selected. If, the sensed condition occurred first or concurrently with the time-out flag, the priority arbitrator 164 would decode the inputs, select the sense flag and cause the MAR select circuitry 166 to enable the appropriate register coupled to the MA BUS 122 so as to reset the master timer 96 and cause the PG controller to begin the next cardiac cycle. If on the other hand the time-out condition was the only flag present when the priority was arbitrated, then a different register and address would be selected and which would ultimately cause the PG controller to pace the heart.

Alternatively, an example of a three-way branch that might occur would be the case wherein an instruction would require that the circuitry to either pace, sense or perform an I/O transaction. In this example, the sense condition flag would again be coupled to the priority 1 multiplexer 156, a buffer request flag would be directly coupled to the priority arbitration circuitry 164 from the branch condition select circuitry 100 and the time-out condition flag would be coupled to the PRIORITY 3 multiplexer 160. If, while the pacing controller was waiting for the priority to be arbitrated, a buffer ready signal occured and the sense flag had not been set, then the MAR select circuitry 166 would cause the PG controller to branch to an I/O routine. Similarly, the circuitry would branch to either of the other flag conditions depending on which flag was present, but would always give first priority to the sense flag, second priority to the I/O transaction and third priority to the time-out flag.

Referring now to the Mode 1 register 94, it is to be recalled that the basic pacing activity of the PG controller is dictated via the contents thereof, see FIG. 6.17, with the specific activity depending primarily upon which of the numerical values from Table 4 is written into the various bit positions. Given this architecture, it is to be noted that asynchronous operation in either of the heart chambers is achieved via the disabling of the appropriate sense amplifier during the appropriate synchronous mode, such as by programming the sensitivity value of the sensed chamber to infinity, thereby effectively preventing any sensing in that chamber and forcing asynchronous operation.

Referring to FIG. 6.17, the MODE 1 register 94 essentially comprises an 8 bit register that is coupled between the C and A BUSES 42 and 44. The mode value is written into the register 94 via the C BUS 42 and read via the A BUS 44. While not all of the bit positions presently dictate the mode of operation, each of the bit positions or flags that do are separately coupled to the other control circuitry so that when they are set, they establish the desired mode. In particular, these bits are contained in the three least significant bit positions and are designated as dual chamber, atrial and trigger mode bits. Also, it is to be noted that the MODE 1 register 94 contains two condition code bits (i.e. bit positions 4 and 5) that can be interrogated by the programmer 10 to determine why a "power up" instruction cycle was performed (i.e. whether it was for a restart, a runaway detect or a low battery voltage condition).

Also contained within the PG controller circuitry are the scratch pad ACC 1 and 2 accumulator registers 88 and 90. These registers act to temporarily store data during each cardiac cycle as it is being manipulated by the ALU 106. Thus, data is written into the registers via the C BUS 42, and read from the registers via the A BUS 44.

Additionally, the PG controller circuitry contains compliment circuitry 124, see FIG. 6.16; master timer circuitry 96, see FIG. 6.18, and zero constant circuitry 182. Each of these elements, too, facilitate the mathematical operations of the ALU 106. In particular, the compliment circuitry 124, which is initiated via the OP CODE O bit from the three bit OP CODE field contained within each instruction word, permits the complimenting of data on the A BUS 44 so that a two's compliment subtract operation may be performed.

The master timer 96, in turn, acts to time each cardiac cycle via the counting of 128 hertz clock pulses as it counts up to the normal or escape period value programmed into the P1 register 72. If the timer 96 is not earlier reset, such as upon sensing naturally occurring ventricular heart activity, the PG controller responds to a less than or equal to zero result from the operation P1 and causes a pacing pulse to be produced. The timer 96 and P1 register 72, thereby establish the minimum or nominal pacing rate.

Referring next to the ALU 106 and the ALU shift decode circuitry 184, see FIG. 6.16, this circuitry provides the PG controller with its logical processing capabilities. In particular, the ALU 106 comprises two, four bit arithmetic logic units that are coupled in series and that permit the PG controller to selectively perform either an add, a subtract, an EXCLUSIVE OR, or a logical AND function. The ALU output may also be decoded and manipulated via the ALU shift decode circuitry 184 in response to control signals from the instruction decode circuitry 102, see FIG. 6.10, so as to complete a selected processing operation. The results of the manipulations are then written onto the C BUS 42 and transferred to the appropriately enabled destinations (e.g. the ACC 1 and 2 registers 88 and 90, the programmable parameter registers, the MODE 1 register 94 or the PC 2 register 168 etc.)

Attention is also directed to the fact that the ALU shift decode circuitry 184 may, depending upon the operation, produce a carry flag, an overflow flag, or various result flags (i.e. result greater than or equal to zero, result less than or equal to zero, result less than zero, result equal to zero). These flag conditions are then used during the various modes of operation to establish condition codes, but which will become more apparent hereinafter upon referring to Tables 5 and 6.

Referring now to the various registers that are coupled to the memory address bus 122 and in particular the PC 2 register 168, see FIG. 6.5, it is to be noted that it generally operates to enhance the branching capabilities of the PG controller. In doing so, it temporarily stores various address values it receives from the C BUS 42. Once needed, the address values are then coupled via the MA BUS 122 to the memory address register 126 and from there to ROM 128 where they are used to select the next instruction.

The memory address register 126, see FIG. 6.7, in turn, comprises an eight bit register that couples the selected addresses to the ROM 128 as well as to the auxiliary MA BUS 186 and one of its associated registers. The instruction address is always directed to the P+1 incrementer 120, but it may also be written into the P SAVE register 166 or onto the A BUS 44.

If an instruction address is written into the P SAVE register 120, it typically is done during a jump subroutine so as to save the address of the current instruction. When the jump subroutine is executed, the PG controller then recalls the address and returns to the primary instruction by merely reloading the memory address register 126 with the address stored in the P SAVE register 166. The P+1 incrementer 196, on the other hand, always increments the address of the instruction presently being performed so that the next instruction in the sequence is readily available, as a potential branch address.

The I/O address constant is a mask-programmable constant that is stored in the similarly named register 170 and is used as the initial address of the subroutine that services I/O transactions.

Also contained within the PG controller circuitry are a number of other circuit elements that interface with the analog circuitry during the control of the pacing pulses. In particular, these elements are the charge cycle/gain turn-down circuitry 188, the sense flag control circuitry 180 and the pulse width control circuitry 190. The charge cycle portion of the circuitry 188, see FIG. 6.21, generally acts to shorten the charging time of the coupling capacitor that couples the pacing amplifier of the analog chip to the heart leads 16A and 16B and thereby enhance the recovery time of the analog sense amplifiers. In operation, the charge cycle circuitry 188 is left "on" for approximately 24 milliseconds after a pace pulse has ended so as to provide a low impedance path and permit the quick recharge of the coupling capacitor.

The gain turn-down portion of the circuitry 188 acts to initiate a gain turn-down signal just prior to the leading edge of a pacing pulse. Thus, approximately 1.0 millisecond before a pacing pulse is generated, a gain turn-down signal is applied and which continues until approximately 36 milliseconds after the delivery of the pacing pulse so as to reduce the gain of the analog pacing amplifiers. This signal thus permits the analog amplifiers to recover quickly following a pacer pulse.

The sense flag control circuitry 180, on the other hand, upon receipt of an atrial or ventricular sense signal from the analog sense detector (not shown), sets the sense flag input to the priority select/detect circuitry 100 and which, in turn, is selected and responded to in a manner dependent upon the mode of operation. The contents of the ROM generated microinstructions and the time dependent behavior of the logic states of the atrial and ventricular sense inputs then cause the sense flag control circuitry 180 and associated logic circuitry to set and to begin timing for a period of approximately 64 milliseconds, see FIG. 6.12. If another sensed event occurs after the 64 millisecond period, an appropriate flag is set and which indicates that a natural pacing event has been sensed and filtered of noise. Noise is defined as any electromagnetic interference or extraneous heart signal or sense amplified artifacts that is of a sufficient amplitude and of a period less than 64 milliseconds. If, however, another sensed event occurs before the 64 milliseconds has expired, then the timer resets and begins timing for another 64 milliseconds. Thus, as long as the timer has not timed out, the sense flag is not set. Consequently the sense flag circuitry 180 acts to produce a 64 millisecond "refractory" and which is also referred to as an "automatic refractory" or "noise window".

Also contained within the sense flag control circuitry 180 is the runaway detect circuitry, see FIG. 6.12. This circuitry operates to detect the presence of a condition whereby the pacing controller is attempting to issue pacing pulses to either heart chamber at a rate that is faster than the rate specified by the period of the runaway one-shots in the analog circuitry. Upon detecting a runaway condition, as evidenced by the counter's detecting that three of five successive pacer pulses having periods less than that established by the runaway one-shots, a runaway detect signal is produced, see FIG. 6.2, and which causes the power-up logic 19 to perform a master clear of all the logic and begin a new cardiac cycle in the nominal parameter mode.

The pulse width and count control circuitry 190 completes the complement of circuitry that comprises the PG controller and operates as a presettable up-counter. In particular and depending upon the mode, the pulse width circuitry 190 operates in parallel with the atrial and ventricular D/A converters 132 and 134 to control the pulse width, while the latter controls pulse amplitude. Thus, the pulse width values stored in the programmable ATRL WIDTH and VENT WIDTH registers 78 and 80 are used to preset the pulse width counter after it is enabled via the C BUS 42 so that upon the counter's counting up to the preset value, an atrial pace or ventricular pace signal is coupled to the pacing amplifiers on the analog chip. The corresponding pacing pulse is then responsively produced and coupled by the analog circuitry to the appropriate heart chamber at the programmed amplitude and pulse width.

Prior to describing the sequence of events that occur during the various pacing modes, attention is now directed to FIG. 9 and Tables 5 and 6 below wherein the various functional fields of the 30 bit instruction words, stored in the ROM 128, are shown. It is to be recognized that while the various fields are grouped together and shown as being consecutive bits, this is not the case in actual practice, due to constraints of the present embodiment's particular integrated circuit layout. Therefore, while a bit location may change, it is to be understood that the fields still comprise the numbers of bits shown and the functions and binary codes still correspond to the binary conditions shown.

TABLE 5

FIELD ASSIGNMENTS

A-BUS SOURCE:

| CODE | ASSIGNMENT PAGE 0 | PAGE 1 |
|---|---|---|
| 0 0 0 | CONSTANT 0 | MODE REG 1 |
| 0 0 1 | CONSTANT 0 | SPARE |
| 0 1 0 | SPARE | SPARE |
| 0 1 1 | PROGRAM CONSTANT | SPARE |
| 1 0 0 | MEMORY ADDRESS REG. | SPARE |
| 1 0 1 | ACCUMULATOR 2 | SPARE |
| 1 1 0 | ACCUMULATOR 1 | SPARE |
| 1 1 1 | TIMER | SPARE |

B-BUS SOURCE:

| CODE | ASSIGNMENT |
|---|---|
| 0 0 0 0 0 | ZERO CONSTANT |
| 0 0 0 0 1 | ZERO CONSTANT |
| 0 0 0 1 0 | PR INTERVAL |
| 0 0 0 1 1 | PACE AMPLITUDE |
| 0 0 1 0 0 | DATA ACQUISITION PORT 0 |
| 0 0 1 0 1 | DATA ACQUISITION PORT 1 |
| 0 0 1 1 0 | ATRIAL WIDTH |
| 0 0 1 1 1 | ATRIAL SENSITIVITY |
| 0 1 0 0 0 | SERIAL PORT ADDRESS |
| 0 1 0 0 1 | INTERRUPT VECTOR |
| 0 1 0 1 0 | MODE REGISTER 2 |
| 0 1 0 1 1 | MODEL NUMBER |
| 0 1 1 0 0 | VENTRICULAR SENSITIVITY |
| 0 1 1 0 1 | MODE WIDTH |
| 0 1 1 1 0 | ACCUMULATOR 4 |
| 0 1 1 1 1 | ACCUMULATOR 3 |
| 1 0 0 0 0 | ABSOLUTE REFRACTORY |
| 1 0 0 0 1 | ATRIAL BLANKING INTERVAL |
| 1 0 0 1 0 | SPARE |
| 1 0 0 1 1 | COMPLEMENT TIMER |
| 1 0 1 0 0 | GD INTERVAL |
| 1 0 1 0 1 | GD ONSET |
| 1 0 1 1 0 | SPARE |
| 1 0 1 1 1 | ACCUMULATOR 5 |
| 1 1 0 0 0 | ACCUMULATOR 5 SHIFTED |
| 1 1 0 0 1 | SPARE |
| 1 1 0 1 0 | PERIOD 1 |
| 1 1 0 1 1 | PERIOD 2 |
| 1 1 1 0 0 | SPARE |
| 1 1 1 0 1 | SPARE |
| 1 1 1 1 0 | SERIAL PORT 0 |
| 1 1 1 1 1 | SERIAL PORT 1 |

C-BUS DESTINATION:

| CODE | ASSIGNMENT (IF OP CODE BIT 2 = 1) PAGE 0 | PAGE 1 |
|---|---|---|
| 0 0 0 0 | DATA ACQUISITION PORT 0 | PERIOD 1 |
| 0 0 0 1 | DATA ACQUISITION PORT 1 | PERIOD 2 |
| 0 0 1 0 | ATRIAL PULSE WIDTH | ABSOLUTE REFRACTORY |
| 0 0 1 1 | VENTRICULAR PULSE WIDTH | ATRIAL BLANK INTERVAL |
| 0 1 0 0 | ACCUMULATOR 2 | MODE REGISTER 2 |
| 0 1 0 1 | ACCUMULATOR 1 | MODE REGISTER 1 |
| 0 1 1 0 | PAGE REGISTER | PAGE REGISTER |
| 0 1 1 1 | ACCUMULATOR 3 | SPARE |
| 1 0 0 0 | PC 2 REGISTER | VENTRICULAR SENSITIVITY |
| 1 0 0 1 | AUXILIARY COUNTER | VENTRICULAR WIDTH |
| 1 0 1 0 | GD ONSET | ATRIAL SENSITIVITY |
| 1 0 1 1 | GD INTERVAL | ATRIAL WIDTH |
| 1 1 0 0 | MODEL NUMBER | PR INTERVAL |
| 1 1 0 1 | ACCUMULATOR 5 | PACER PULSE AMPLITUDE |
| 1 1 1 0 | ACCUMULATOR 4 | SERIAL PORT 0 |

TABLE 5-continued

| | | | | | |
|---|---|---|---|---|---|
| 1 | 1 | 1 | 1 | NO OP | SERIAL PORT 1 |

*(IF OP CODE BIT 2=0)

| | | | | |
|---|---|---|---|---|
| 0 | 0 | X | X | MODE SENSITIVITY |
| 0 | 1 | X | X | R WAVE SENSITIVITY |
| 1 | 0 | X | X | P WAVE SENSITIVITY |
| 1 | 1 | X | X | P or R WAVE SENSITIVITY |
| X | X | 0 | 0 | SELECT I/O SUBROUTINE ADRS TO MA BUS |
| X | X | 0 | 1 | SELECT P SAVE TO MA BUS |
| X | X | 1 | 0 | SELECT PC2 TO MA BUS |
| X | X | 1 | 1 | SELECT C BUS TO MA BUS |

*Page bit ignored and the 4 bits are simultaneously decoded as two groups of two bits each.
NOTE: X implies a "DON'T CARE" CONDITION UTILITY: This field may be assigned as a branch address, a constant or a trigger. When assigned as an address or a constant, an 8 bit value as designated, otherwise the trigger assignments are as follows and where the seventh bit is not used.

(TRIGGER ASSIGNMENTS)

| BIT POSITION | | | | | | BIT POSITION | | | | | |
|---|---|---|---|---|---|---|---|---|---|---|---|
| 6 | 5 | 4 | 3 | 2 | ASSIGNMENT | 6 | 5 | 4 | 3 | 2 | ASSIGNMENT |
| 0 | 0 | 0 | 0 | 0 | MODE RESET OF SENS FLG | 1 | 0 | 0 | 0 | 0 | TRIG. C PAGE 1 |
| 0 | 0 | 0 | 0 | 1 | TR. ATRIAL B.P. | 1 | 0 | 0 | 0 | 1 | SPARE |
| 0 | 0 | 0 | 1 | 0 | TR. SHORT VENT. B.P. | 1 | 0 | 0 | 1 | 0 | SPARE |
| 0 | 0 | 0 | 1 | 1 | RESET ATRIAL SENS FLGS | 1 | 0 | 0 | 1 | 1 | SPARE |
| 0 | 0 | 1 | 0 | 0 | RESET PAGE | 1 | 0 | 1 | 0 | 0 | A B-C BUS |
| 0 | 0 | 1 | 0 | 1 | SET WRITE FLAG | 1 | 0 | 1 | 0 | 1 | A + B-C BUS |
| 0 | 0 | 1 | 1 | 0 | RESET WRITE FLAG | 1 | 0 | 1 | 1 | 0 | SPARE |
| 0 | 0 | 1 | 1 | 1 | SET FLAG 1 | 1 | 0 | 1 | 1 | 1 | ROTATE LEFT |
| 0 | 1 | 0 | 0 | 0 | RESET FLAG 1 | 1 | 1 | 0 | 0 | 0 | ROTATE RIGHT |
| 0 | 1 | 0 | 0 | 1 | TRIGGER URL | 1 | 1 | 0 | 0 | 1 | ARITHMETIC |
| 0 | 1 | 0 | 1 | 0 | ENBL LD BR COND FF | 1 | 1 | 0 | 1 | 0 | SPARE |
| 0 | 1 | 0 | 1 | 1 | DISABL LD BR COND FF | 1 | 1 | 0 | 1 | 1 | SPARE |
| 0 | 1 | 1 | 0 | 0 | SET FLAG 2 | 1 | 1 | 1 | 0 | 0 | SPARE |
| 0 | 1 | 1 | 0 | 1 | RESET FLAG 2 | 1 | 1 | 1 | 0 | 1 | SPARE |
| 0 | 1 | 1 | 1 | 0 | RESET TIMER | 1 | 1 | 1 | 1 | 0 | SPARE |
| 0 | 1 | 1 | 1 | 1 | TRIG C PAGE 0 | 1 | 1 | 1 | 1 | 1 | SPARE |

(IF OP CODE BIT 2=1)

| | | |
|---|---|---|
| 1 | 0 | |
| 0 | 0 | SELECT I/O SUBROUTINE ADRS TO MA BUS |
| 0 | 1 | SELECT P SAVE TO MA BUS |
| 1 | 0 | SELECT PC2 TO MA BUS |
| 1 | 1 | SELECT C BUS TO MA BUS |

NOTE: THE UTILITY FIELD ASSIGNMENT IS DETERMINED VIA THE FOLLOWING LOGIC CONDITIONS:

Address: $(\overline{BASA}) \cdot (PRI\ BIT\ 0) + (BASA) \cdot (PRI\ BIT\ 2) = 1$ Constant: A−BUS source field = 0011
Trigger: none of the above conditions are true

OP CODE:

| BIT POSITION | | | ASSIGNMENT | | | | |
|---|---|---|---|---|---|---|---|
| 2 | 1 | 0 | CURRENT ADRS IN P | A BUS | CARRY IN = | BRANCH ON 1ST CYCLE | MNEMONIC |
| 0 | 0 | 0 | YES | YES | 1 | NO | JSC |
| 0 | 0 | 1 | YES | NO | 0 | NO | JSR |
| 0 | 1 | 0 | NO | YES | 1 | NO | JMC |
| 0 | 1 | 1 | NO | NO | 0 | NO | JMP |
| 1 | 0 | 0 | NO | YES | $C_{FF}$ | YES | COM |
| 1 | 1 | 0 | NO | YES | 1 | YES | CMC |
| 1 | 0 | 1 | NO | NO | $C_{FF}$ | YES | CFF |
| 1 | 1 | 1 | NO | NO | 0 | YES | CLC |

PRIORITY SELECT:

| BIT POSITION | | | |
|---|---|---|---|
| 3 | | | ASSIGNMENT |
| 0 | | | PRI 1 - UTILITY FIELD |
| | | | PRI 3 - PC1(NXT) |
| 1 | | | PRI 1 - (PC1(NXT) |
| | | | PRI 3 - UTILITY FIELD |
| 2 | 1 | 0 | |
| 0 | 0 | 0 | SEL LEVEL 0 |
| 0 | 0 | 1 | SEL LEVEL 1 |
| 0 | 1 | 0 | SEL LEVEL 2 |
| 0 | 1 | 1 | SEL LEVEL 3 |
| 1 | 0 | 0 | SEL LEVEL 4 |
| 1 | 0 | 1 | SEL LEVEL 5 |
| 1 | 1 | 0 | SEL LEVEL 6 |
| 1 | 1 | 1 | SEL LEVEL 7 |

PRIORITY ENABLE:
BIT POSITION

TABLE 5-continued

| 2 | 1 | 0 | |
|---|---|---|---|
| 1 | X | X | ENABLE PRIORITY 1 |
| X | 1 | X | ENABLE PRIORITY 2 |
| X | X | 1 | ENABLE PRIORITY 3 |

NOTE: X implies a "DON'T CARE" condition

TABLE 6
BRANCH CONDITION SEL MUX ASSIGNMENTS

| | PRIORITY LEVEL | | |
|---|---|---|---|
| | 1 | 2 | 3 |
| SELECT LEVEL | | | |
| 0 | FLAG 1 | FLAG 2 | OVFL FLAG |
| 1 | SMOOTH FLAG | MODE BIT 6 | CARRY FLAG |
| 2 | AUX TIMEOUT | MODE SENSE | ALU $\geq 0$ |
| 3 | NOM PAR FLAG | MODE PACE FLAG | N FLAG |
| 4 | TRIG MODE BIT 0 | DUAL CHAM MODE BIT | ATR MODE BIT |
| 5 | GD MODE | RESULT = 0 | GD FLAG |
| 6 | SENSE FLAG | BUFFER READY | ALU RESULT $\leq 0$ |
| 7 | SENSE FLAG | BUFFER READY | ALU RESULT $\geq 0$ |

Beginning with the A-BUS SOURCE Field, it is comprised of three bits. The three bits are generated by ROM and determine the code, while a fourth bit (not shown) determines which one of two pages of code assignments is to be selected, selection being determined by the page and jam circuitry. Thus, the A BUS SOURCE field is able to accommodate 16 different operands. Depending upon the page, the source field determines which register or timer's contents are written onto the A BUS 44. For example, the selection of page 0 and the A BUS SOURCE field condition code of 101 causes the selection and transfer of the memory address register 126's contents to the A BUS 44, and which condition typically implies that the utility field is being designated as an address. If, however, page 1 and the same code is selected, then a spare condition is implied and the condition goes unnoticed by the PG controller.

The next field is the five bit B-BUS SOURCE field and which operands enable the coupling of 32 different registers onto the B BUS 40. In particular, the B BUS SOURCE field is used to transfer the contents of the programmed parameter registers onto the B BUS 40 such as during programmer interrogations or as the PG controller sequences through the various instructions of the algorithm in process.

The next field is the four bit C-BUS DESTINATION field, and which again is a paged field. While four bits from ROM define the bus destination, the fifth bit (not shown) pages the bus and thereby expands the number of destinations to 32 or 16 per page. The C BUS DESTINATION field therefore defines the register to which data from the ALU 106 is to be transferred. The data is selected via the A and B BUS SOURCE fields and is transmitted via the ALU 106 to the register defined by the C BUS DESTINATION field.

It is also to be noted that the interpretation of the C BUS DESTINATION field is dependent upon the binary value of the second bit of the OP CODE field of each instruction word and which will be described hereinafter. Thus, not only is the C BUS DESTINATION field paged, but so too is its functional interpretation, depending upon whether a wait instruction or an immediate execution instruction is to take place. In particular, if the most significant OP CODE bit is designated by a binary "1" a normal paged transfer occurs. Otherwise, if the most significant OP CODE bit is a binary "0", then a jump instruction occurs, and which produces a "wait" condition, such as when a branch condition requires that the PG controller wait until a timer times out or a sense condition to occur.

The next field of the instruction word comprises the 8 bit UTILITY field and which can either be used as an address, a constant or a trigger. In particular, the UTILITY field is used as a constant when the A BUS SOURCE field code is a binary 1011; and as an address field when the logic condition of (BASA)·(priority bit 0)+(BASA)·(priority bit 2)=1 where BASA is the branch address source assignment defined by the ROM instruction. Otherwise, the eight bit utility field is used as a trigger in all other instances.

When the UTILITY field is used as a trigger, the least significant two bits of the field are used to determine which of the PRIORITY 2 source addresses are to be coupled to the MA BUS 122 (i.e. P SAVE, PC2, C BUS or I/O ADRS CONSTANT). While for all other OP CODES, the next five bits (i.e. bit positions 2 through 6) determine which of 32 possible operations is to be performed. It is also to be noted that the seventh bit of the utility field is not used during trigger conditions.

The logic operation of the ALU 106 is next determined by the OP (i.e. operation) CODE field of the instruction word. Depending upon which OP CODE bits are set, several different operations may be performed and which are performed either immediately as an unconditional branch or after suitable wait periods. For example, the JSC condition results in a wait and a two's compliment subtraction of the A BUS 44's contents from the B BUS 42's contents, while the JSR condition results in a wait and the addition of the B BUS 40's contents to the A BUS 44's contents. On the other hand, the COM, CMC, CFF and CLC functions result in unconditional branches.

The next seven bits or PRIORITY SELECT and ENABLE fields establish the possible sources of the next address to be written into the MAR register 126. In particular, the most significant bit of the four bit PRIORITY SELECT field establishes the BASA by determining if the P+1 incrementer 120 is enabled as a PRI- ORITY 1 source address or as a PRIORITY 3 source address. Thus, the priorities amongst two of the three priority levels are variable, while the second priority level remains fixed. For example if the P+1 incrementer 120 is assigned PRIORITY 1, then the utility field is assigned PRIORITY 3 and vice versa while the second priority level remains constant. The next three priority select bits, in turn, establish which one of the eight groups of three branch conditions is selected to control the jump address or, in other words, which of the branch conditions within a given group is enabled and allowed to affect program flow.

The three bit PRIORITY ENABLE field completes the instruction work and establishes which priority level within the selected level of three branch conditions relative to the instruction is enabled. This selection, in turn, establishes which branch condition, assigned to the various priority selects, is selected. The specific selection that occurs via the PRIORITY SELECT and ENABLE fields, however, can be more clearly understood upon referring to Table 6.

Referring to Table 6, the predetermined priority arbitration matrix for the present embodiment is shown and which is representative of the hardwired selection process that is enabled via the branch condition select circuitry 100, the priority multiplexers, 156, 158 and 160, the priority arbitrator 164 and the PRIORITY ENABLE and SELECT fields. As should be apparent from the matrix, only one specific pre-assigned branch condition is selected upon the determination of a branch condition select level and a priority level. And, while the priority levels may vary, it is to be noted that if a branch condition flag is not present for a selected first priority level, then the PG controller will select from amongst the other of the two possible flags that are set for the other selected select level. For example, the selection of the zero branch condition select level, corresponds to flag 1 at priority level 1; flag 2 at priority level 2 and the overflow flag to priority level 3. Therefore, if flag 1 occurs and priority level 1 has first priority, then the pacing algorithm will branch to flag 1, irrespective of the other branch conditions that were flagged at that selected level. Similarly, the algorithm will branch to the flag 2 branch condition, even though the priority level 1 was enabled, if the flag 1 and overflow flag branch conditions weren't flagged but the flag 2 branch condition was flagged. Thus, during conditional branches any one of three enabled prioritized branch conditions for a given select level can be selected, depending upon which flags are set as the priority arbitrator 164 is clocked.

Referring now to FIG. 10, a flow chart is shown of the pacing algorithm that is programmed in ROM 128 and by which the circuitry of FIGS. 4, 5 and 6, is controlled during the various modes. While the pacing algorithm will be described first with respect to the single chamber modes of operation and then with respect to the dual chamber modes of operation, it is to be noted that the term algorithm is used all inclusively to include all instructions, micro or otherwise, to perform a specific function. Attention is also directed to Table 7 below wherein a brief description is given of the letter designations of FIG. 10 as they relate to the individual pacing modes. It is to be noted that a particular instruction is labeled as being within the instruction sequence for a particular mode, if its execution is necessary for the proper operation of that mode. In some cases though the execution of some instructions is redundant to a particular mode and therefore those instructions are not included in those modes' instruction sequences.

TABLE 7

| | |
|---|---|
| A | SINGLE CHAMBER DEMAND (VVI OR AAI) |
| B | SINGLE CHAMBER TRIGGERED (VVT OR AAI) |
| C | A-V SEQUENTIAL (DVI) |
| D | DOUBLE DEMAND (DDD) |
| E | P-WAVE SYNCHRONOUS DEMAND (VDD) |
| F | GRACEFUL DEGRADATION |
| H | RATE SMOOTHING |
| J | MAG RATE |
| K | NOMINAL PARAMETER |

Upon completing a power up master clear (PU MCLR) operation or at the beginning of each cardiac cycle, the address of the interrupt routine "return" is loaded into the PC 2 register 168. The algorithm next interrogates the interrupt vector logic 114, see FIG. 5.11, to determine if an interrupt request is present. If an interrupt request is present, the algorithm branches to the first address thereof, otherwise it begins with the branch address specified in the PC 2 register 168. At the same time it resets the master timer 96 which triggers the start of an absolute refractory (ARF) and an atrial blanking (ABP) period, if appropriate.

The algorithm's next branch depends upon the contents of the interrupt vector logic and which is dependent upon the presence or absence of pertinent interrupt requests. Depending upon the contents of the register the algorithm next causes either the MAG RATE routine to be initiated, the graceful degradation interrupt service routine to be executed or a normal sequence of commands to be executed. It is to be noted too that upon executing either the graceful degradation service routine or the MAG RATE routine, the algorithm in all cases returns to entry point (B) and continues with a normal cardiac cycle. However, if the algorithm branches to the MAG RATE routine, it will operate in that mode until the magnet is removed and at which time it will return to the normal routine. Therefore, assuming that MAG RATE is not selected and/or that the other branches are complete, the algorithm next transfers the shifted or scaled value in the ACC 5 register 86 into the ACC 1 register 88. This scaled value is a percentage of the previous cycle's period and is used only if rate smoothing is selected.

The algorithm next transfers the programmed upper rate limit into the ACC 2 register 90 before it encounters a branch condition wherein it branches depending on whether a dual or single chamber mode is programmed. Assuming that a single chamber mode is programmed, the algorithm transfers the "back-up" period (used for hysterisis and which can either be positive or negative) into the ACC 1 register 88 before it encounters a three-way branch condition wherein it either (1) branches to the nominal parameter routine, if the nominal parameter flag is set, (2) branches to an instruction that transfers the normal period into the ACC 1 register 88, if the previous ventricular event was a paced event (i.e. the pace flag is set), or (3) maintains the backup period of the escape interval if the previous cycle's activity was a sensed event and in which case the algorithm continues, uninterrupted. Before continuing, it is also to be noted that the normal period or escape interval is the programmed period of the normal or nominal rate (as distinguished from the nominal parameter pacing mode) and is programmed into the P1 register 72. Thus, depending upon the mode and functions enabled, if a naturally occurring ventricular event is not sensed, the circuitry will produce a pacing pulse at the end of the normal period prior to beginning the next cardiac cycle. Similarly, the back up period (assuming rate hysterisis is enabled) establishes the period of the cycle, depending on whether the previous event was paced or sensed.

Ignoring the nominal parameter mode for the moment though and assuming that the pace flag was set and that the normal period has been transferred, the algorithm next resets the mode sense flag. Depending upon the programmed mode, this instruction causes either the ventricular or atrial sense flip flop of the sense flag control circuitry 180 to be reset, see FIG. 6.13, thereby enabling the sensing of either of the respective chambers. Afterwards, the algorithm encounters another two-way branch condition and checks for a buffer ready flag or the relative value T of the master timer 96 with respect to the value in the absolute refractory register 74. Specifically, the algorithm computes the difference between the value T of the master timer 96 and the value in the absolute refractory register 74 and checks the result. It does not proceed with this branch, however, until the result is less than or equal to zero, and which indicates that the current time is greater than or equal to the absolute refractory period (i.e. at the end thereof).

If, while waiting, for the aforementioned conditions to occur, the buffer ready flag is set and which is indicative of an I/O request, the controller performs a jump to entry point (E) and re-enters the algorithm at a point where it executes the I/O transaction. During an I/O transaction, the controller resets the WRITE flag and then checks to see if the READ flag is set. If the READ flag is set it obtains the source and destination register addresses from the serial port address register 38 and sequentially transfers the high and low 8 bit bytes from the source registers to the destination registers (i.e. from the S/P O and I data registers 46 and 48, during a WRITE, and to these same registers, during a READ). Otherwise, the controller sets the WRITE flag before performing the appropriate WRITE transfers. Upon completing an I/O transaction, the controller returns to the instruction pointed to by the P SAVE register 166, and from which it had just branched, before re-continuing with the algorithm.

When the controller returns from the I/O subroutine, it again checks to see if either of the branch conditions was fulfilled in the interim. If another buffer ready flag is present, the controller branches and performs this. If not, the controller continues to wait until the value T of the master timer 96 is greater than the value contained within the absolute refractory register 74. Upon the occurence of this event, the controller jumps to the next instruction.

The next instruction is a three-way branch condition and which requires that the controller wait until either the mode sense flag is set, a buffer ready flag is detected, or the master timer 96's value T is greater than the value stored in the ACC 1 register 88. Before continuing, it is to be recalled that the ACC 1 register 88 contains a value corresponding to the normal or backup period, depending upon whether or not the previous ventricular event was paced or sensed. If upon checking the branch conditions, it is found that T is greater than the value in the ACC 1 register 88, the controller jumps to the mode pace instruction and reenters the algorithm at entry point (C). The mode pace instruction then causes the appropriate chamber of the heart, as specified by the programmed mode, to be paced (i.e. the ventricle for a single chamber or dual chamber ventricular mode or the atrium for a single chambered atrial mode).

Assuming that the ventricle is to be paced, then during the mode pace instruction the contents of the ventricular width register 60 are loaded into the pulse width counter 202. At the same time, the contents of the pace amplitude register 56 are converted via the D/A converters 132 and 134 and transmitted to the analog circuitry and used to control the pacer pulse amplifier and produce a pacing pulse of the appropriate amplitude so as to properly pace the ventricle. The pacing pulse is thus delivered at the programmed amplitude, until the pulse width counter 190 times out and terminates the pacing pulse. Upon terminating the pacing pulse, the controller executes the remaining two instructions (but only because the single chamber and dual chamber modes share a common mode pace instruction) and begins the next cardiac cycle. Thus, it is also to be recognized that the above sequence of events correspond to the ventricular demand (VVI) mode. Similarly, it should be apparant that this sequence of events will also accommodate the atrial demand (AAI) mode, if that mode is programmed and the atrium is paced/sensed in lieu of the ventricle.

Instead, if during the three-way branch condition and prior to the condition of T being greater than the value in the ACC 1 register 88, an atrial or ventricular sensed event occurred, then the controller will interrogate the MODE 1 register 94 to determine if a triggered mode (e.g. R-wave synchronous or P-wave synchronous) had been programmed. Depending upon the binary state of the least significant bit of the Mode 1 register 94, the controller will then either perform a sequence of instructions relevant to the triggered modes or proceed to the next cardiac cycle.

If a triggered mode was programmed, then the controller checks to determine whether or not the time at which the sensed event occurred was greater than that specified by the upper rate limit register (i.e. the value stored in the P2 register 70). If the rate at which the sensed event occurred is less than the URL, then the controller causes the ventricle to be paced per the previously described ventricular mode of operation. Otherwise, if the sensed event occurred at a rate which is greater than that specified by the upper rate limit, the controller clears or resets the mode sense flag, adds the value of the PR interval stored in the PR interval register 64 to the current time T and transfers the sum to the ACC 2 register 90. The controller then waits until the cardiac cycle progresses beyond the refractory value in the ACC 2 register 90 before returning to the three-way branch condition and again checking for a sensed event, a buffer ready or a time-out condition. Assuming that the time of the delayed sensed event is greater than the URL, the controller re-enters the algorithm at entry point (C) and paces the ventricle or atrium as previously described. Thus, during the triggered modes, the atrium and ventricle are paced synchronously at a rate below the URL, after sensing a P or R wave in the desired chamber of the heart.

Returning now to the controller's interrogation of the third bit of the mode 1 register 94, if a mode type 2 or dual chamber mode is programmed via the presence of a binary "1", the controller branches to the various subroutines and instructions representative of the various dual chamber modes. In particular and with reference to FIG. 10d, the controller confirms whether or not rate smoothing is enabled and, if it is, it assigns the programmed URL value in the P2 register 50 to the ACC 3 register 82 and then forms an upper rate and lower rate limit for rate smoothing (i.e. $URL_{RS}$ and $LRL_{RS}$). In forming the $LRL_{RS}$ and $URL_{RS}$ limits of rate variation, the controller utilizes the programmed percentage of smoothing desired (i.e. 3.25%; 6.25%; 12.5%; or 25%) and the period of the last cardiac cycle via the selection of the scaled value in the ACC 1 register 88. It is to be noted that like the rate smoothing flag, the percentage of rate smoothing is programmed into the MODE 2 register 62 and decoded via the mode decode circuitry 152 so as to cause the appropriate shifting or division via the shift multiplexer 92. Similarly, the MODE 2 register contains the graceful degradation enable bit and MAG RATE flag, discussed earlier.

The $LRL_{RS}$ and $URL_{RS}$ values as discussed are values relative to the period of the last cardiac cycle and, which period at the end of each cardiac cycle the controller transfers to the ACC 5 register 86. This value is then scaled at the start of each cardiac cycle via the shift multiplexer 92 which, depending upon the programmed percentage of smoothing desired, shifts and zero fills the value of the previous period so as to form a scaled value. This scaled value is then transferred to the ACC 1 register 88. The controller then respectively forms the periods of the $LRL_{RS}$ and $URL_{RS}$ by subtracting and adding the scaled value from and to the previous period and storing these limits in the ACC 3 and ACC 1 registers 82 and 88. After verifying that these rate smoothing limits are inside the range defined by the programmed upper and lower rate limits (i.e. the values in the P1 and P2 registers 72 and 70), these new limits, $URL_{RS}$ and $LRL_{RS}$, are used by the algorithm in the same fashion as it uses the aforementioned programmed URL and LRL parameters when rate smoothing is not enabled. Therefore the present heart prosthesis utilizes a past history of cardiac activity in addition to its inherent arithmetic capabilities to affect the manner in which it regulates cardiac activity.

Upon confirming whether or not rate smoothing is programmed and establishing $URL_{RS}$ and $LRL_{RS}$, the controller transfers the programmed URL value to the ACC 2 register 90 and checks to see if the graceful degradation flag is set. In order for the the graceful flag to be set GD degradation function must be enabled, the atrial rate must, on the average, exceed the programmed upper rate limit and the onset interval must be completed, see FIG. 5.20. If the GD flag is set, the controller will add a preprogrammed graceful degradation offset value in the ACC 4 register 84 to the programmed URL and form a new effective URL in the ACC 2 register 90.

This sum forms $URL_{GD}$ or the shortest period at which the ventricle may be paced during the current cardiac cycle. When the auxiliary counter times out, after a programmed number of cycles, the ACC 4 register 84 is then incremented via the GD service routine, thereby increasing the GD offset and forcing the $URL_{GD}$ lower at regular intervals, thus, causing the pacing rate to be decreased from the programmed URL to the programmed normal rate in a predictable manner. It is also to be noted that the slope or rate at which the pacing rate is decreased is dependent upon the size of the programmed step value or GD interval and which it is to be recalled may be programmed at any of 250 values. Thus, depending upon whether or not graceful degradation is selected, either the programmed URL or $URL_{GD}$ value is stored in the ACC 2 register 90.

Upon confirming that the graceful degradation function is enabled and establishing $URL_{GD}$, the controller reenters the algorithm at entry point (D1) and checks to see if $URL_{RS}$ (assuming rate smoothing is enabled) is higher than $URL_{GD}$. If it is, it continues with the algorithm, otherwise it substitutes $URL_{RS}$ for $URL_{GD}$, or $URL_{eff}$. Before continuing, it is to be noted too that because this description is with respect to a single cardiac cycle, the heart's condition may vary from cycle to cycle and thus the bounds for rate smoothing and graceful degradation will vary with time.

The controller next resets the atrial sense flag and forms the negative of the T3 period (i.e. the escape period minus a PR interval or the end of the atrial sensing period and beyond which atrial activity can not trigger a ventricular event or, in the case of the double demand mode, the time at which the atrium is paced if an atrial event has not been sensed.) The controller then encounters a three-way branch condition wherein it checks for an R or P-wave sense flag, a buffer ready flag or to see if T3 has expired. The buffer ready condition has already been described, but the other two have not and will therefore be described now. If an R or P-wave sense flag is detected and assuming a P-wave is sensed, the controller branches and checks to see which chamber was sensed. Because a P-wave is assumed, the controller then checks to see if the atrial blanking interval (i.e. the ABP value stored in register 80) has expired.

If the atrial blanking interval has not expired, and which might occur due to false sensing before the sense circuitry 180 has settled down, the controller resets the atrial sense flag and returns to the three-way branch condition where it again looks for a sense flag. Assuming, however, that a valid P-wave is sensed after the start of the cardiac cycle, and that the controller is programmed in either the P-wave synchronous or double demand mode and that the atrial blanking interval has expired, the controller branches and triggers a P-sense condition for the purpose of effecting proper operation of graceful degradation and forms a "default time" at which the ventricle will be paced. The default time corresponds to the value of T at the time of the sensed event plus a PR interval. The controller also resets the atrial sense flag, forms the negative of the time T2 and checks to see if T2 (i.e. 1/URL minus a PR interval) has expired. If T2 has expired, and which assures that the atrial rate is less than URL EFF, the controller branches and reenters the algorithm at entry point (H); otherwise it transfers the $URL_{eff}$ value for that cycle to the ACC 5 register 86, thereby cancelling the default time and assuring that the ventrical will not be paced at a rate faster than $URL_{eff}$.

Upon reentering the algorithm at entry point (H), the controller encounters another three-way branch condition wherein it looks for a P or R-wave sense flag, a buffer ready flag or the timing out of the time in the ACC 5 register 86. If an R-wave is not sensed in the time before the master timer 96 reaches the one or the other of the possible values stored in the ACC 5 register 86, the controller branches to the mode pace routine and paces the ventricle. If rate smoothing is enabled, the controller then checks to see if the time T of the ventricular event is greater than or equal to the $URL_{eff}$ value. If the rate is greater than $URL_{eff}$, the controller assigns the $URL_{eff}$ value to the ACC 5 register 86 for the next cycle and from which the next $LRL_{RS}$ and $URL_{RS}$ values are calculated; otherwise it assigns the actual value T to the ACC 5 register 86 before beginning the next cardiac cycle.

Alternatively, if a sense flag is detected before the ventricle is paced, the controller branches and confirms the type of sense flag. If a P-wave sense flag is detected, the controller again triggers a P sense for graceful degradation and resets the atrial sense flag. If, on the other hand, an R-wave sense flag is detected, the controller confirms its authenticity by checking to see if the absolute ventricular refractory period has expired. If the ventricular refractory interval has not timed-out, the controller resets the R-wave sense flag and returns to the first three-way branch; otherwise it stores the time T or the $URL_{eff}$ value before beginning the next cardiac cycle.

If, however, at the first three-way branch no R or P-wave sense flags are detected before the escape interval expires, the controller branches and transfers the $LRL_{eff}$ value in the ACC 1 register 88 to the ACC 5 register 86 so as to establish a maximum time by which the ventricle will be paced. The controller then checks to see if the P-sync mode is programmed (i.e. VDD,) and, if it is, it re-enters the algorithm at entry point (H) and proceeds to wait for a natural R-wave or pace the ventricle at $LRL_{eff}$.

If the P-sync mode is not programmed, the controller paces the atrium and triggers a P-wave sense for graceful degradation before resetting the ventricular sense flag. Next, the controller encounters a third three-way branch condition wherein it checks for an R-wave sense flag, a buffer ready flag or the timing-out of $LRL_{eff}$. If the R-wave sense flag is set, indicating the occurrence of a natural R-wave, the controller confirms its authenticity by checking to see that the ventricular refractory has expired. If it has expired, the controller re-enters the algorithm at entry point (G) and transfers the appropriate time T to the ACC 5 register 86. If the R-wave sense flag was not authentic, the controller returns to the third three-way branch condition. On the other hand, if $LRL_{eff}$ expires and an R-wave is not sensed, the controller re-enters the algorithm at entry point (C), paces the ventricle and stores the time T.

Thus, during the dual chamber modes and depending upon whether rate smoothing or graceful degradation is selected, the controller essentially follows one or the other of two primary branches. It is also to be noted that the A-V sequential mode, like the previously mentioned single chamber made of asynchronous operation, is essentially achieved via the programming of the double demand mode, while setting the atrial sense value to the maximum possible value, so as to essentially negate the sensing of that chamber and achieve the additional mode without a great deal of extraneous circuitry and-/or instructions.

Returning now to FIG. 10a, it is to be recalled that the controller at the first two-way branch condition at the start of each cardiac cycle checks to see if the nominal parameter flag is set. While it has been assumed that it is not, if it is, the controller branches and transfers the nominal pre-programmed absolute refractory and normal period values to the ACC 2 and ACC 1 registers 90 and 88. The controller then resets the sense flags and enters a two-way branch condition wherein it checks for a buffer ready or waits until the absolute refractory times out. Upon the refractory's timing out, the controller next encounters a three-way branch condition wherein it waits for an R-wave sense flag, a buffer ready flag or the normal period time-out. If an R-wave sense occurs, the controller begins the next cardiac cycle; otherwise if the period times-out, the controller paces the ventricle via the MODE pace subroutine at a nominal pulse width of 1 millisecond, before beginning the next cardiac cycle. Thus, during the nominal parameter mode, the controller essentially paces the heart in the ventricular demand mode at the pre-programmed nominal pacing parameters.

Recalling too that at the start of each cycle the controller checks to see if the MAG RATE or graceful degradation service routine flags are set, the controller may also branch to one or the other of these subroutines. In particular, if the MAG RATE flag is set, the controller initiates or powers up the A/D converter circuitry 118 and transfers the scaled output of the A/D converter to the ACC 3 register 82. Next, the controller waits for the time T corresponding to the calculated period of the MAG RATE to expire, before pacing the ventricle at a pulse width of 1 millisecond and beginning the next cardiac cycle.

Alternatively, if the graceful degradation service routine flag is set, the controller loads the auxiliary counter 98 with the graceful degradation interval before transferring the programmed upper rate limit to the ACC 1 register 88 and checking to see if the graceful degradation flag is set. If the flag is set, the controller confirms that the upper rate limit imposed by graceful degradation ($URL_{GD}$) is not less than the programmed lower rate limit and transfers the value of the $URL_{GD}$ in the ACC 4 register 84 and returns to the program at entry point (B).

If, however, the graceful degradation onset interval has not been completed, the graceful degradation flag is not set and the controller branches and loads the ACC 4 register 84 with a zero and the auxiliary counter 98 with the onset interval value and re-enters the algorithm at entry point (B). Once enough cardiac cycles have passed so that the auxiliary counter 96 has counted down to zero, indicating the end of the onset interval, another GD interrupt is generated except that on this interrupt the GD flag will be set. It should be recalled too that before the graceful degradation flag can be reset, it is necessary that two consecutive intervals be encountered where the atrial rate is less than the programmed URL. Once reset, any onset interval must also again be repeated the next time the atrial rate exceeds the URL.

While the present invention has been described in detail with respect to its presently preferred embodiment and its associated pacing modes, it is to be recognized that various other alternative embodiments and modes of operation may suggest themselves to those of skill in the art, upon a reading hereof. Furthermore, it is to be recognized that the various pacing instructions and control circuitry may be varied by one of skill in the art without departing from the spirit of the present invention. Therefore the invention should be interpreted broadly to encompass all equivalent embodiments within the spirit and scope of the following claims.

What is claimed is:

1. An implantable, programmable cardiac pacemaker system comprising:
    (a) external programmer means for transmitting and receiving radio frequency encoded signals, said encoded signals defining at least one of a plurality of selectable pacing modes and a plurality of selectable pacing parameters associated with the selected pacing mode;
(b) implantable pulse generator means responsive to ones of said encoded signals for cyclically producing pacing pulses for at least one chamber of the heart, said pulse generator means including:
  (1) pulse controller means for performing a plurality of inter-cycle operations associated with the selected pacing mode during the production of pacing pulses for each cardiac cycle and further including:
    (i) means for storing ones of said encoded signals,
    (ii) means for storing a plurality of inter-cycle instructions, each instruction designating at least one of a plurality of the inter-cycle operations,
    (iii) means for sensing a plurality of analog conditions including electrical activity of the heart,
    (iiii) means responsive to said stored encoded signals and said inter-cycle instructions for prioritizing the inter-cycle operations of the selected pacing made, and
  (2) input/output controller means responsive to received ones of said encoded signals for selectively writing the selected pacing mode and its associated pacing parameters into said encoded signal storage means during a write mode and including means for selectively reading ones of said encoded signal storage means and ones of said analog conditions and further including means for transmitting encoded radio frequency signals corresponding thereto to said external programmer means during a read mode; and
(c) means for coupling said pacing pulses to the appropriate chambers of the heart and said sensed analog conditions to said pulse generator means.

2. A cardiac pacemaker system as set forth in claim 1 wherein said pulse generator means includes rate smoothing means for controlling the rate at which pacing pulses are produced and further including means for preventing the pacing rate from changing by more than a predetermined percentage from one cycle to the next.

3. A cardiac pacemaker system as set forth in claim 2 wherein said pulse generator means includes means responsive to a pacing parameter defining an upper pacing rate limit for enabling said rate smoothing means when sensed naturally occurring heart complexes in one chamber of the heart occur at a rate in excess of the upper pacing rate limit.

4. A cardiac pacemaker system as set forth in claim 3 wherein one of said pacing parameters defines a lower pacing rate limit and includes means for enabling said rate smoothing means when sensed naturally occurring heart complexes in the predetermined one chamber of the heart occur at a rate below the lower pacing rate limit.

5. A cardiac pacemaker system as set forth in claim 1 wherein said pulse generator means includes means responsive to a pacing parameter defining an upper pacing rate limit for reducing the rate at which pacing pulses are produced from one cycle to the next over a number of cardiac cycles from a first pacing rate defined by one of said pacing parameters, upon sensing naturally occurring complexes in one chamber of the heart in excess of the upper pacing rate limit, down to a second lower pacing rate defined by another of said pacing parameters.

6. A cardiac pacemaker system as set forth in claim 5 wherein said rate reducing means includes means responsive to a pacing parameter defining an onset interval for delaying the operation of said rate reducing means, even after sensing heart complexes occurring at a rate in excess of said upper pacing rate limit, until said onset interval times-out.

7. A cardiac pacemaker system as set forth in claim 5 wherein said analog sensing means also senses P-wave complexes and said rate reducing means includes means for periodically recording the occurrence of each P-wave complex over a predetermined amount of time and means for comparing the recorded number of occurrences at the end of each period to said upper pacing rate limit.

8. A cardiac pacemaker system as set forth in claim 7 wherein said periodic recording means includes counter means for positively counting each P-wave complex in excess of said upper rate limit and negatively counting each P wave complex less than said upper rate limit.

9. A cardiac pacemaker system as set forth in claim 5 wherein said rate reducing means includes means for reducing the rate from one cycle to the next in equal incremental steps.

10. A cardiac pacemaker system as set forth in claim 1 wherein said external programmer means includes means for transmitting sync signals and said pulse generator means includes means for monitoring said sync signals for a predetermined sequence thereof, said pulse generator means further including means for transmitting a pulse generator response signal to said external programmer means once said predetermined sequence is detected, thereby synchronizing said external programmer means to said pulse generator means.

11. A cardiac pacemaker system as set forth in claim 1 wherein said pulse generator means includes means for transmitting error identifying signals to said external programmer means, upon detecting errors in said received signals.

12. A cardiac pacemaker system as set forth in claim 1 wherein said pulse generator means and said external programmer means each include means for trasmitting with each transmission an error check word having a mathematical association to each encoded transmission and each also includes means for decoding each received error check word so as to determine whether or not an error occurred during the transmission.

13. A cardiac pacemaker system as set forth in claim 12 wherein said decoding means includes means for producing a cyclic redundancy check generator polynomial and means for dividing portions of each transmission, including the error check word transmitted therewith, by said cyclic redundancy check generator polynomial.

14. A cardiac pacemaker as set forth in claim 13 wherein said cyclic redundancy check generator polynomial comprises a summation including a predetermined portion of each cyclic redundancy check word.

15. A cardiac pacemaker system as set forth in claim 1 wherein said analog sensing means includes:
  (a) a plurality of transducer means, each coupled to an analog parameter of interest, for producing an analog signal corresponding thereto;
  (b) means for selectively interrogating one of said plurality of transducers; and
  (c) means for converting the analog signal of an interrogated transducer to a digital signal, said conversion means comprising:

(i) first counter means coupled to the interrogated analog signal and operable at a first frequency for producing a first count proportional to the magnitude thereof, (ii) an analog signal of known magnitude, (iii) second counter means coupled to said analog signal of known magnitude and operable at said first frequency simultaneously with said first counter for producing a second count proportional to the analog signal of known magnitude, and (iiii) means for producing a digital signal representative of the ratio of said first count to said second count for each analog signal.

16. A cardiac pacemaker system as set forth in claim 1 including a pulse generator power supply and means coupled thereto for interrogating the state of said power supply, said power supply interrogation means comprising:

(a) means for producing a first signal proportional to a selected analog parameter of said power supply means of unknown magnitude;

(b) means operative simultaneously with said first signal producing means for producing a second signal proportional to an analog parameter of known magnitude;

(c) means responsive to said first and second signals for determining a scaled relative value therebetween; and (d) means for adding said scaled value to one of the pacing parameters of the selected pacing mode so as to reflect the state of said power supply in a changed condition of said pacing pulses.

17. A cardiac pacemaker system as set forth in claim 1 wherein said pulse generator includes:

(a) a pulse generator power supply;

(b) means responsive to the presence of a magnetic field for producing an interrupt request;

(c) means responsive to said interrupt request for sensing the condition of said power supply;

(d) means for scaling the sensed condition of said power supply relative to a known condition; and (e) means for causing pacing pulses to be produced at a rate related to the scaled condition.

18. A cardiac pacemaker system as set forth in claim 17 including means responsive to at least one of said encoded signals for preventing said pulse generator from producing said interrupt request.

19. A cardiac pacemaker system as set forth in claim 1 wherein said pulse generator means includes an electrically conductive container mounted in surrounding relation thereto and said coupling means includes at least two electrical conductors affixed between said pulse generator means and the heart and wherein said pulse generator means further includes means responsively coupled to ones of said encoded signals for operating said pulse generator means in either a unipolar or a bipolar configuration, a selected one of said conductors being grounded to said container during a unipolar configuration and being ungrounded during a bipolar configuration.

20. A cardiac pacemaker system as set forth in claim 1 wherein said pulse generator means includes means monitoring the occurrence of a pacing event relative to the beginning of each cardiac cycle for controllably varying the rate of delivery of a pacing pulse during the next successive cardiac cycle to a predetermined percentage of the previous cycle's rate.

21. A cardiac pacemaker system as set forth in claim 20 including means for varying the amount of permitted variation in pacing rate from one cardiac cycle to the next.

22. A cardiac pacemaker system as set forth in claim 21 wherein one of said pacing parameters defines the amount of cycle to cycle rate variation in a range from zero to fifty percent of the previous cycle's rate.

23. A cardiac pacemaker system as set forth in claim 1 wherein said pulse generator means includes means for storing an alternative plurality of pacing parameters for at least one of said plurality of pacing modes and further includes means for reverting from the selected pacing mode to that one of said plurality of pacing modes having said alternative pacing parameters and operating in that other mode relative to the alternative pacing parameters.

24. Improved implantable pulse generator apparatus operable to cyclically produce and couple pacing pulses to at least one chamber of the heart in relation to a selected one of a plurality of pacing modes, a plurality of pacing parameters associated with the selected mode and sensed electrical activity of the heart, the improvement comprising:

(1) means for storing a plurality of operating instructions defining a plurality of operations to be performed between each cycle of the selected pacing mode and wherein ones of said instructions define a plurality of operations; and (2) means for prioritizing the inter-cycle operations of said pulse generator during the production of pacing pulses for the selected pacing mode.

25. Pulse generator apparatus as set forth in claim 24 including means for storing an alternative plurality of pacing parameters for at least one of said plurality of pacing modes and means for automatically reverting to said one mode and its associated alternative pacing parameters and producing pacing pulses relative thereto and to said one mode's operating instructions.

26. Pulse generator apparatus as set forth in claim 24 wherein ones of the selected mode's associated pacing parameters define a first pacing rate, a second lower pacing rate and a rate limit, and including means responsive to said sensed electrical activity for comparing the rate of occurrence of the sensed electrical activity to said rate limit and further including means responsive to said comparision means for incrementally reducing the rate at which pacing pulses are produced, if the rate of said sensed activity exceeds said rate limit, from said first pacing rate down to said second pacing rate and thereafter maintaining said second reduced pacing rate so long as the rate of sensed activity exceeds said rate limit.

27. Pulse generator apparatus as set forth in claim 24 including means monitoring the occurrence of a pacing event relative to the beginning of each cardiac cycle for controlling the pacing rate of the next successive cardiac cycle so that the rate of each cardiac cycle does not change by more than a predetermined percentage of the rate of the previous cardiac cycle.

* * * * *

UNITED STATES PATENT AND TRADEMARK OFFICE
CERTIFICATE OF CORRECTION

PATENT NO. : 4,562,841
DATED : January 7, 1986
INVENTOR(S) : Brian P. Brockway et al It is certified that error appears in the above-identified patent and that said Letters Patent are hereby corrected as shown below:

Column 41, Line 23, "made" should read -- mode --.

Column 42, Line 42, "trasmitting" should read -- transmitting --.

Signed and Sealed this

Fifteenth Day of April 1986

[SEAL]

Attest:

DONALD J. QUIGG

Attesting Officer     Commissioner of Patents and Trademarks